US007041795B2

(12) United States Patent
Rhodes et al.

(10) Patent No.: US 7,041,795 B2
(45) Date of Patent: May 9, 2006

(54) POTASSIUM CHANNEL INTERACTING POLYPEPTIDES AND USES THEREOF

(75) Inventors: Kenneth Rhodes, Neshanic Station, NJ (US); Maria Betty, Moorestown, NJ (US); Huai-Ping Ling, Princeton Junction, NJ (US); Wengian An, Framingham, MA (US)

(73) Assignees: Millennium Pharmaceuticals, Inc, Cambridge, MA (US); Wyeth, Madison, NJ (US)

( * ) Notice: Subject to any disclaimer, the term of this patent is extended or adjusted under 35 U.S.C. 154(b) by 507 days.

(21) Appl. No.: 10/118,590

(22) Filed: Apr. 8, 2002

(65) Prior Publication Data

US 2005/0277761 A1    Dec. 15, 2005

Related U.S. Application Data

(63) Continuation of application No. 09/298,731, filed on Apr. 23, 1999, now Pat. No. 6,369,197.

(60) Provisional application No. 60/110,033, filed on Nov. 25, 1998, provisional application No. 60/109,333, filed on Nov. 20, 1998, provisional application No. 60/110,277, filed on Nov. 30, 1998.

(51) Int. Cl.
| | |
|---|---|
| C07K 14/00 | (2006.01) |
| C12N 15/00 | (2006.01) |
| C12N 15/12 | (2006.01) |
| C12N 15/63 | (2006.01) |
| C12Q 1/68 | (2006.01) |

(52) U.S. Cl. .................... 530/350; 435/69.1; 435/325; 435/320.1; 435/6

(58) Field of Classification Search ................ 530/350; 435/69.1, 325, 320.1, 6
See application file for complete search history.

(56) References Cited

FOREIGN PATENT DOCUMENTS

| WO | WO 97/31112 | 8/1997 |
|---|---|---|
| WO | WO 98/16185 | 4/1998 |
| WO | WO 99/49038 | 9/1999 |
| WO | WO 00/31133 A2 | 6/2000 |
| WO | WO 00/70049 A2 | 11/2000 |
| WO | WO 00/70049 A3 | 11/2000 |
| WO | WO 01/53312 A1 | 7/2001 |

OTHER PUBLICATIONS

Buxbaum JD,et al.Calsenilin: a calcium-binding protein that interacts with the presenilins and regulates the levels of a presenilin fragment. Nat Med. Oct. 1998;4(10):1177-81.*
Bradshaw, H.; Stellyes, L. The sequence of C. elegans cosmid C44C1.A;Reference No.: Z20642 A;Accession: T29566 Oct. 15, 1999.*

Mickle JE et al. Genotype-phenotype relationships in cystic fibrosis. Med Clin North Am. May 2000;84(3):597-607.*
Voet et al. Biochemistry. 1990. John Wiley & Sons, Inc. pp. 126-128 and 228-234.*
Yan et al., Two-amino acid molecular switch in an epithelial morphogen that regulates binding to two distinct receptors. Science 290: 523-527, 2000.*
Adachi, Y. et al., "Identification and characterization of SET, a nuclear phosphoprotein encoded by the translocation break point in acute undifferentiated leukemia," *J. Biol. Chem.*, 269:2258-2262 (1994).
Bilbe,G., et al., "Restin: a novel intermediate filament-associated protein highly expressed in the Reed-Sternberg cells of Hodgkin's disease," *EMBO J.* 11(6):2103-2113 (1992).
Bonaldo et al., GenBank Accession No. AA859724 [online], "Calcium-binding protein NCS-1" (Mar. 14, 1998).
Buxbaum, Joseph D. , et al., "Calsenilin: A calcium-binding protein that interacts with the presenilins and regulates the levels of a presenilin fragment", *Nature Medicine*, vol. 4, No. 10, pp. 1177-1181 (1998).
Carrion, Angel M., et al., "DREAM is a $CA^{2+}$-regulated transcriptional repressor", *Nature*, vol. 398, pp. 80-84 (1999).
Castagna, Michela et al. "Molecular Characteristics of Mammalian and Insect Amino Acid Transporters: Implications for Amino Acid Homeostatis" *The Journal of Experimental Biology* 200:269-286 (1997).
Cunningham, E. et al., "Phosphatidylinositol transfer protein dictates the rate of inositol trisphosphate production by promoting the synthesis of PIP2," *Curr Biol.* 5(7):775-83 (1995).
DeCastro, E. et al., "Regulation of rhodopsin phosphorylation by a family of neuronal calcium sensors" *Biochem Biophys Res Commun.*;216(1):133-40 1995).
Dickeson,S.K., et al., "Isolation and sequence of cDNA clones encoding rat phosphatidylinositol transfer protein," *J. Biol. Chem.* 264 (28):16557-16564 (1989).

(Continued)

*Primary Examiner*—Joseph Murphy
(74) *Attorney, Agent, or Firm*—Woodcock Washburn LLP

(57) ABSTRACT

The invention provides isolated nucleic acids molecules, designated PCIP nucleic acid molecules, which encode proteins that bind potassium channels and modulate potassium channel mediated activities. The invention also provides antisense nucleic acid molecules, recombinant expression vectors containing PCIP nucleic acid molecules, host cells into which the expression vectors have been introduced, and nonhuman transgenic animals in which a PCIP gene has been introduced or disrupted. The invention still further provides isolated PCIP proteins, fusion proteins, antigenic peptides and anti-PCIP antibodies. Diagnostic methods utilizing compositions of the invention are also provided.

13 Claims, 26 Drawing Sheets

OTHER PUBLICATIONS

Dixon, J., "Role of the Kv4.3 K+ channel in ventricular muscle. A molecular correlate for the transient outward current" *Circ Res.*;79(4):659-68. (1996).

Endo, T.A. et al., "A new protein containing an SH2 domain that inhibits JAK kinase," *Nature.* 387(6636):921-4 (1997).

Fukuda, J. et al., "Breakdown of cytoskeletal filaments selectively reduces Na and Ca spikes in cultured mammal neurones," *Nature.* 294(5836):82-5 (1981).

Funkhouser, J.D.; "Amino-terminal sequence of a phospholipid transfer protein from rat,lung," Biochem. Biophys. Res. Commun. 145:1310-1314 (1987).

Hoffman, D.A. et al., "K+ channel regulation of signal propagation in dendrites of hippocampal pyramidal neurons," *Nature.* 387(6636):869-75 (1997).

Hoffman, D.A. et al., "Downregulation of transient K+ channels in dendrites of hippocampal CA1 pyramidal neurons by activation of PKA and PKC," *J Neurosci.* 18(10):3521-8 (1998).

Honore, E. et al., "Different types of K+ channel current are generated by different levels of a single mRNA," *EMBO J.* 11(7):2465-71 (1992).

Hoppe-Seyler, "Purification and characterization of two putative HLA class II associated proteins: PHAPI and PHAPII," *Biol. Chem.*, 375:113-126 (1994).

Jan, L.Y. et al., "How might the diversity of potassium channels be generated?" *Trends Neurosci.* 13(10):415-9 (1990).

Johnson, B.D. et al., "A cytoskeletal machanism for Ca2+ channel metabolic dependence and inactivation by intracellular Ca2+," *Neuron.* 10(5):797-804 (1993).

Kaab, S. et al., "Molecular basis of transient outward potassium current downregulation in human heart failure: a decrease in Kv4.3 mRNA correlates with a reduction in current density" *Circulation.* 98(14):1383-93 (1998).

Kim, E. et al. "Clustering of Shaker-type K+ channels by interaction with a family of membrane-associated guanylate kinases" Nature 378:85-88 (Nov. 2, 1995).

Levin, G. et al., "Phosphorylation of a K+ channel alpha subunit modulates the inactivation conferred by a beta subunit. Involvement of cytoskeleton," *J Biol Chem.* 271(46):29321-8 (1996).

Li, M., et al., "The myeloid leukemia-associated protein SET is a potent inhibitor of protein phosphatase 2A," *J. Biol. Chem.* 271 (19):11059-11062 (1996).

Lombardi, Stephen J. et al. "Structure-Activity Relationships of the $K_v\beta1$ Inactivation Domain and Its Putative Receptor Probed Using Peptide Analogs of Voltage-gated Potassium Channel α- and β-Supunits" *The Journal of Biological Chemistry* 273(46):30092-30096 (Nov. 13, 1998).

Masiakowski, P. et al., "Nerve growth factor induces the genes for two proteins related to a family of calcium-binding proteins in PC12 cells," *Proc Natl Acad Sci U S A.* 85(4):1277-81 (1988).

Nagase,T. et al., "Prediction of the coding sequences of unidentified human genes. XI. The complete sequences of 100 new cDNA clones from brain which code for large proteins in vitro," *DNA Res.* 5 (5):277-286 (1998).

Nagata, K. et al., "Replication factor encoded by a putative oncogene, set, associated with myeloid leukemogenesis," *Proc. Natl. Acad. Sci. U.S.A.*, 92:4279-4283 (1995).

Naka, T. et al., "Structure and function of a new STAT-induced STAT Inhibitor," *Nature.* 387(6636):924-9 (1997).

Nakamura, T.Y. et al., "Modulation of Kv4 channels, key components of rat ventricular transient outward K+ current, by PKC," *Am J Physiol.* 273(4 Pt 2):H1775-86 (1997).

National Cancer Intsitute-Cancer Genome Aanatomy Project, GenBank Accession No. AI038858 [online],". . . *Homo sapiens* cDNA clone IMAGE:1659605 3' similar to SW:VIS3_Rat P35333 Visinin-like Protein" (Jul. 1, 1998).

Nerbonne, J., "Regulation of voltage-gated K+ channel expression in the developing mammalian myocardium", *J Neurobiol.*;37(1):37-59. (1998)Review.

Panaretou, C. et al., "Characterization of p150, an adaptor protein for the human phosphatidylinositol (Ptdlns) 3-kinase. Substrate presentation by phosphatidylinositol transfer protein to the p150.Ptdins 3-kinase complex," *J Biol Chem.* 272(4):2477-85 (1997).

Pierre,P., et al., "CLIP-170 links endocytic vesicles to microtubules," *Cell* 70 (6):887-900 (1992).

Pongs, O. et al., "Regulation of the activity of voltage-gated potassium channels by beta subunits" *Sem. Neurosci.* 7:137-146 (1995).

Prevarskaya, N.B. et al., "Role of tyrosine phosphorylation in potassium channel activation. Functional association with prolactin receptor and JAK2 tyrosine kinase," *J Biol Chem.* 270(41):24292-9 (1995).

Scannevin, R.H. and Trimmer, J.S. "Cytoplasmic Domains of Voltage-Sensitive K+ Channels Involved in Mediating Protein-Protein Interactions" Biochemical and Biophysical Research Communications 232:585-589 (1997).

Serodio, P. et al., "Cloning of a Novel Component of A-type $K^+$ Channels Operating at Subthreshold Potential with Unique Expression in Heart and Brian" *Journal of Neurophysiology,* vol. 75, No. 5, pp. 2174-2179 (1996).

Sheng, M. et al., "Subcellular segregation of two A-type K+ channel proteins in rat central neurons," *Neuron.* 9(2):271-84 (1992).

Sheng, M. and Kim, E. "Ion channel associated proteins" Current Opinion in Neurobiology 6:602-608 (1996).

Simon, H.U. et al., "Molecular characterization of hNRP, a cDNA encoding a human nucleosome-assembly-protein-I-related gene product involved in the induction of cell proliferation," *Biochem. J.,* 297:389-397 (1994).

Starr, R. et al., "A family of cytokine-inducible inhibitors of signalling," *Nature.* 387(6636):917-21 (1997).

Touchot, N. et al., "Four additional members of the ras gene superfamily isolated by an oligonucleotide strategy: molecular cloning of YPT-related cDNAs from a rat brain library," *Proc Natl Acad Sci U S A.* 84(23):8210-4 (1987).

Van Hille, B. et al., "Identification of two subunit A isoforms of the vacuolar H(+)-ATPase in human osteoclastoma," *J Biol Chem.* 268(10):7075-80 (1993).

Voet et al. *Biochemistry.* John Wiley & Sons, Inc., pp. 126-128 and 228-234 (1990).

Von Lindern, M. et al., "Can, a putative oncogene associated with myeloid leukemogenesis, may be activated by fusion of its 3' half to different genes: characterization of the set gene," *Mol. Cell Biol.,* 12:3346-3355 (1992).

Rhodes et al. BLASTN Search in EST Database using the mouse p19 nucleic acid Sequence (1998).

Rhodes et al. BLASTN Search in Nucleic Acid Database using the mouse p19 nucleic acid Sequence (1998).

Rhodes et al. BLASTN Search using the human 1v protein sequence (1998).

Rhodes et al. BLASTN Search in EST Database using the rat 1vl nucleic acid sequence (1998).
Rhodes et al. BLASTN Search in Nucleic Acid Database using the rat 1vl nucleic acid sequence (1998).
Rhodes et al. BLASTN Search in EST Database using the human 9ql nucleic acid sequence (1998).
Rhodes et al. BLASTN Search in Nucleic Acid Database using the human 9ql nucleic acid sequence (1998).
Nagase,T. et al., GenBank accession No.: AB018264 for "*Homo sapiens* mRNA for KIAA0721 protein, partial cds", NCBI (1998).
Li, M. et al. GenBank accession No.: U51924 for "Human phosphatase 2A inhibitor I2PP2A mRNA, complete cds", NCBI (1998).
Bilbe, G. et al. GenBank accession No.: P30622 for "Restin (cytoplasmic limker protein-170 alpha-2) (clip-170) (reed-Sternberg intermediate filament associatedprotein)", NCBI (1998).
Van Hille, B. et al. GenBank accession No.: P38606 for "Vacuolar ATP synthase catalytic subunit A, ubiquitous isoform (V-atpase 69 KD subunit) (isoform VA68)", NCBI (1998).
Van Hille, B. et al. GenBank accession No.: B46091 for "H+-transporting ATPase (EC 3.6.1.35), vacuolar, A chain, VA68 type—human.", NCBI (1997).
Touchot,N. et al. GenBank accession No.: P05712 for "Ras-related protein RAB-2", NCBI (1998).
Dickenson, S.K. et al. GenBank accession No.: P16446 for "Phosphatidylinositol transfer protein alpha isoform (PTDINS transfer protein alpha) (PTDINSTP) (PI-TP-alpha)", NCBI (1998).
Dickeson,S.K., et al. GenBank accession No.: M25758 for "Rat phosphatidylinositol transfer protein mRNA, complete cds", NCBI (1994).
Lee, N.H. et al. GenBank accession No.: AA849706 for "EST192473 Normalized rat muscle, Bento Soares *Rattus* sp. cDNA clone RMUAH89 3' end, mRNA sequence", NCBI (1995).
NCI-CGAP, GenBank accession No.: AA757119 for "Ah53h07.s1 Soares_testis_NHT *Homo sapiens* cDNA clone 1309405 3', mRNA sequence", NCBI (1998).
Sasaki, Z. et al. GenBank accession No.: AU035979 for "Sugano mouse brain mncb Mus musculus cDNA clone MNCb-7005, mRNA sequence", NCBI (1998).
An, W.F. et al. "Modulation of A-type potassium channels by a family of calcium sensors." *Nature* 403:553-556 (Feb. 3, 2000).
Eck & Wilson in Goodman & Gilman's The Pharmacological Basis of Therapeutics. 9th ed. McGraw Hill, NY, pp. 77-101.
Stratagene Catalog, "Gene characterization kits." 1998, p. 39.

* cited by examiner

HUMAN 1V DNA (CD:225-875)
GAATAGCCCCCTTTCACTTCTGAGTCCCTGCATGTGCGGGGCTGAAGAAGGAAGCCAGAAGCCTCCTAGCCTCGCCTCCA
CGTTTGCTGAATACCAAGCTGCAGGCGAGCTGCCGGGCGCTTTTCTCTCCTCCAATTCAGAGTAGACAAACCACGGGGAT
TTCTTTCCAGGGTAGGGGAGGGGCCGGGCCCGGGGTCCCAACTCGCACTCAAGTCTTCGCTGCCATGGGGGCCGTCATGG
GCACCTTCTCATCTCTGCAAACCAAACAAAGGCGACCCTCGAAAGATAAGATTGAAGATGAGCTGGAGATGACCATGGTT
TGCCATCGGCCCGAGGGACTGGAGCAGCTCGAGGCCCAGACCAACTTCACCAAGAGGGAGCTGCAGGTCCTTTATCGAGG
CTTCAAAAATGAGTGCCCCAGTGGTGTGGTCAACGAAGACACATTCAAGCAGATCTATGCTCAGTTTTTCCCTCATGGAG
ATGCCAGCACGTATGCCCATTACCTCTTCAATGCCTTCGACACCACTCAGACAGGCTCCGTGAAGTTCGAGGACTTTGTA
ACCGCTCTGTCGATTTTATTGAGAGGAACTGTCCACGAGAAACTAAGGTGGACATTTAATTTGTATGACATCAACAAGGA
CGGATACATAAACAAAGAGGAGATGATGGACATTGTCAAAGCCATCTATGACATGATGGGGAAATACACATATCCTGTGC
TCAAAGAGGACACTCCAAGGCAGCATGTGGACGTCTTCTTCCAGAAAATGGACAAAAATAAAGATGGCATCGTAACTTTA
GATGAATTTCTTGAATCATGTCAGGAGGACGACAACATCATGAGGTCTCTCCAGCTGTTTCAAAATGTCATGTAACTGGT
GACACTCAGCCATTCAGCTCTCAGAGACATTGTACTAAACAACCACCTTAACACCCTGATCTGCCCTTGTTCTGATTTTA
CACACCAACTCTTGGGACAGAAACACCTTTTACACTTTGGAAGAATTCTCTGCTGAAGACTTTCTTATGGAACCCAGCAT
CATGTGGCTCAGTCTCTGATTGCCAACTCTTCCTCTTTCTTCTTCTTGAGAGAGACAAGATGAAATTTGAGTTTGTTTTG
GAAGCATGCTCATCTCCTCACACTGCTGCCCTATGGAAGGTCCCTCTGCTTAAGCTTAAACAGTAGTGCACAAAATATGC
TGCTTACGTGCCCCCAGCCCACTGCCTCCAAGTCAGGCAGACCTTGGTGAATCTGGAAGCAAGAGGACCTGAGCCAGATG
CACACCATCTCTGATGGCCTCCCAAACCAATGTGCCTGTTTCTCTTCCTTTGGTGGGAAGAATGAGAGTTATCCAGAACA
ATTAGGATCTGTCATGACCAGATTGGGAGAGCCAGCACCTAACATATGTGGGATAGGACTGAATTATTAAGCATGACATT
GTCTGATGACCCAAACTGCCCCG

HUMAN 1V PROTEIN
MGAVMGTFSSLQTKQRRPSKDKIEDELEMTMVCHRPEGLEQLEAQTNFTKRELQVLYRGFKNECPSGVVNEDTFKQIYAQ

FFPHGDASTYAHYLFNAFDTTQTGSVKFEDFVTALSILLRGTVHEKLRWTFNLYDINKDGYINKEEMMDIVKAIYDMMGK

YTYPVLKEDTPRQHVDVFFQKMDKNKDGIVTLDEFLESCQEDDNIMRSLQLFQNVM

Fig. 1

RAT 1vN (r1vN) DNA (CD: 339-1037)

```
GGCACACAACCCCTGGATTCTTCGGAGAATATGCCGTGAGGTGTTGCCAATTATTAGTTCTCTTGGCTAGCAGATGTTTA
GGGACTGGTtaaGCCTTTGGAGAAATTACCTTAGGAAAACGGGGAAATAAAAGCAAAGATTACCATGAATTGCAAGATTA
CCTAGCAATTGCAAGGtagGAGGAGAGAGGTGGAGGGCGGAGTAGACAGGAGGGAGGGAGAAAGtgaGAGGAAGCTAGGC
TGGTGGAAATAACCCTGCACTTGGAACAGCGGCAAAGAAGCGCGATTTTCCAGCTTtaaATGCCTGCCCGCGTTCTGCTT
GCCTACCCGGGAACGGAGATGTTGACCCAGGGCGAGTCTGAAGGGCTCCAGACCTTGGGGATAGTAGTGGTCCTGTGTTC
CTCTCTGAAACTACTGCACTACCTCGGGCTGATTGACTTGTCGGATGACAAGATCGAGGATGATCTGGAGATGACCATGG
TTTGCCATCGGCCTGAGGGACTGGAGCAGCTTGAGGCACAGACGAACTTCACCAAGAGAGAACTGCAAGTCCTTTACCGG
GGATTCAAAAACGAGTGCCCCAGTGGTGTGGTTAACGAAGAGACATTCAAGCAGATCTACGCTCAGTTTTTCCCTCATGG
AGATGCCAGCACATACGCACATTACCTCTTCAATGCCTTCGACACCACCCAGACAGGCTCTGTAAAGTTCGAGGACTTTG
TGACTGCTCTGTCGATTTTACTGAGAGGAACGGTCCATGAAAAACTGAGGTGGACGTTTAATTTGTACGACATCAATAAA
GACGGCTACATAAACAAAGAGGAGATGATGGACATAGTGAAAGCCATCTATGACATGATGGGGAAATACACCTATCCTGT
GCTCAAAGAGGACACTCCCAGGCAGCACGTGGACGTCTTCTTCCAGAAAATGGATAAAAATAAAGATGGCATTGTAACGT
TAGACGAATTTCTCGAGTCCTGTCAGGAGGATGACAACATCATGAGGTCTCTACAGCTGTTCCAAAATGTCATGTAACTG
AGGACACTGGCCATCCTGCTCTCAGAGACACTGACAAACACCTCAATGCCCTGATCTGCCCTTGTTCCAGTTTTACACAT
CAACTCTCGGGACAGAAATACCTTTTACACTTTGGAAGAATTCTCTGCTGAAGACTTTCTACAAAACCTGGCACCGAGTG
GCTCAGTCTCTGATTGCCAACTCTTCCTCCCTCCTCCTCTTGAGAGGGACGAGCTGAAATCCGAAGTTTGTTTTGGAAGC
ATGCCCATCTCTCCATGCTGCTGCTGCCCTGTGGAAGGCCCCTCTGCTTGAGCTTAAACAGTAGTGCACAGTTTTCTGCG
TATACAGATCCCCAACTCACTGCCTCTAAGTCAGGCAGACCCTGATCAATCTGAACCAAATGTGCACCATCCTCCGATGG
CCTCCCAAGCCAATGTGCCTGCTTCTCTTCCTCTGGTGGGAAGAAAGAACGCTCTACAGAGCACTTAGAGCTTACCATGA
AAATACTGGGAGAGGCAGCACCTAACACATGTAGAATAGGACTGAATTATTAAGCATGGTGGTATCAGATGATGCAAACA
GCCCATGTCATTTTTTTTTCCAGAGGTAGGGACTAATAATTCTCCCACACTAGCACCTACGATCATAGAACAAGTCTTTT
AACACATCCAGGAGGGAAACCGCTGCCCAGTGGTCTATCCCTTCTCTCCATCCCCTGCTCAAGCCCAGCACTGCATGTCT
CTCCCGGAAGGTCCAGAATGCCTGTGAAATGCTGTAACTTTTATACCCTGTTATAATCAATAAACAGAACTATTTCGTAC
AAAAAAAAAAAAAAAA
```

Fig. 2A

RAT 1vN (r1vN) PROTEIN

MLTQGESEGLQTLGIVVVLCSSLKLLHYLGLIDLSDDKIEDDLEMTMVCHRPEGLEQLEAQTNFTKRELQVLYRGFKNEC

PSGVVNEETFKQIYAQFFPHGDASTYAHYLFNAFDTTQTGSVKFEDFVTALSILLRGTVHEKLRWTFNLYDINKDGYINK

EEMMDIVKAIYDMMGKYTYPVLKEDTPRQHVDVFFQKMDKNKDGIVTLDEFLESCQEDDNIMRSLQLFQNVM.

Fig. 2B

MOUSE 1V (CD:477-1127)
CGGCCCCCTGAGATCCAGCCCGAGCGCGGGGCGGAGCGGCCGGGTGGCAGCAGGGGCGGGCGGGCGGAGCGCAGCTCCCG
CACCGCACGCGGCGCGGGCTCGGCAGCCTCGGCCGTGCGGGCACGCCGGCCCCGTGTCCAACATCAGGCAGGCTTTGGGG
CTCGGGGCTCGGGCCTCGGAGAAGCCAGTGGCCCGGCTGGGTGCCCGCACCGGGGGGCGCCTGTCAAGGCTCCCGCGAGC
CTCTGGCCCTGGGAGTCAGTGCATGTGCCTGGCTGAAGAAGGCAGCAGCCACGAGCTCCAGGCGCCCCGGCCCCACGTTT
TCTGAATACCAAGCTGCAGGCGAGCTGCTCGGGGCTTTTTTGCTTTCTCGCTTTTCCTCTCCTCCAATTCAAAGTGGGCA
ATCCACACCGATTTCTTTTCAGGGGAGGGAAGAGACAGGGCCTGGGGTCCCAAGACGCACACAAGTCTTCGCTGCCATGG
GGGCCGTCATGGGCACTTTCTCCTCCCTGCAGACCAAACAAAGGCGACCCTCTAAAGACAAGATTGAGGATGAGCTAGAG
ATGACCATGGTTTGCCACCGGCCTGAGGGACTGGAGCAGCTTGAGGCACAGACGAACTTCACCAAGAGAGAACTGCAAGT
CTTGTACCGGGGATTCAAAAACGAGTGCCCTAGCGGTGTGGTCAATGAAGAAACATTCAAGCAGATCTACGCTCAGTTTT
TCCCTCACGGAGATGCCAGCACATATGCACATTACCTCTTCAATGCCTTCGACACCACCCAGACAGGCTCTGTAAAGTTC
GAGGACTTTGTGACTGCTCTGTCGATTTTACTGAGAGGGACAGTCCATGAAAAACTAAGGTGGACGTTTAATTTGTATGA
CATCAATAAAGACGGCTACATAAACAAAGAGGAGATGATGGACATAGTCAAAGCCATCTATGACATGATGGGGAAATACA
CCTATCCTGTGCTCAAAGAGGACACTCCCAGGCAGCATGTGGATGTCTTCTTCCAGAAAATGGATAAAAATAAAGATGGC
ATTGTAACGTTAGATGAATTTCTTGAATCATGTCAGGAGGATGACAACATCATGAGATCTCTACAGCTGTTCCAAAATGT
CATGTAACTGAGGACACTGGCCATTCTGCTCTCAGAGACACTGACAAACACCTTAATGCCCTGATCTGCCCTTGTTCCAA
TTTTACACACCAACTCTTGGGACAGAAATACCTTTTACACTTTGGAAGAATTCTCTGCTGAAGACTTTCTACAAAACCTG
GCACCACGTGGCTCTGTCTCTGAGGGACGAGCGGAGATCCGACTTTGTTTTGGAAGCATGCCCATCTCTTCATGCTGCTG
CCCTGTGGAAGGCCCCTCTGCTTGAGCTTAATCAATAGTGCACAGTTTTATGCTTACACATATCCCCAACTCACTGCCTC
CAAGTCAGGCAGACTCTGATGAATCTGAGCCAAATGTGCACCATCCTCCGATGGCCTCCCAAGCCAATGTGCCTGCTTCT
CTTCCTCTGGTGGGAAGAAAGAGTGTTCTACGGAACAATTAGAGCTTACCATGAAAATATTGGGAGAGGCAGCACCTAAC
ACATGTAGAATAGGACTGAATTATTAAGCATGGTGATATCAGATGATGCAAATTGCCCATGTCATTTTTTTCAAAGGTAG
GGACAAATGATTCTCCCACACTAGCACCTGTGGTCATAGAGCAAGTCTCTTAACATGCCCAGAAGGGGAACCACTGTCCA
GTGGTCTATCCCTCCTCTCCATCCCCTGCTCAAACCCAGCACTGCATGTCCCTCCAAGAAGGTCCAGAATGCCTGCGAAA
CGCTGTACTTTTATACCCTGTTCTAATCAATAAACAGAACTATTTCGTAAAAAAAAAAAAAAAAAAAA

MOUSE 1V PROTEIN
MGAVMGTFSSLQTKQRRPSKDKIEDELEMTMVCHRPEGLEQLEAQTNFTKRELQVLYRGFKNECPSGVVNEETFKQIYAQ
FFPHGDASTYAHYLFNAFDTTQTGSVKFEDFVTALSILLRGTVHEKLRWTFNLYDINKDGYINKEEMMDIVKAIYDMMGK
YTYPVLKEDTPRQHVDVFFQKMDKNKDGIVTLDEFLESCQEDDNIMRSLQLFQNVM.

Fig. 3

RAT 1VL DNA (CD: 31-714)
GTCCCAAGTCGCACACAAGTCTTCGCTGCCATGGGGGCCGTCATGGGTACCTTCTCGTCCCTGCAGACCAAACAAAGGCG
ACCCTCTAAAGACATCGCCTGGTGGTATTACCAGTATCAGAGAGACAAGATCGAGGATGATCTGGAGATGACCATGGTTT
GCCATCGGCCTGAGGGACTGGAGCAGCTTGAGGCACAGACGAACTTCACCAAGAGAGAACTGCAAGTCCTTTACCGGGGA
TTCAAAAACGAGTGCCCCAGTGGTGTGGTTAACGAAGAGACATTCAAGCAGATCTACGCTCAGTTTTTCCCTCATGGAGA
TGCCAGCACATACGCACATTACCTCTTCAATGCCTTCGACACCACCCAGACAGGCTCTGTAAAGTTCGAGGACTTTGTGA
CTGCTCTGTCGATTTTACTGAGAGGAACGGTCCATGAAAAACTGAGGTGGACGTTTAATTTGTACGACATCAATAAAGAC
GGCTACATAAACAAGAGGAGATGATGGACATAGTGAAAGCCATCTATGACATGATGGGGAAATACACCTATCCTGTGCT
CAAAGAGGACACTCCCAGGCAGCACGTGGACGTCTTCTTCCAGAAAATGGATAAAAATAAAGATGGCATTGTAACGTTAG
ACGAATTTCTCGAGTCCTGTCAGGAGGATGACAACATCATGAGGTCTCTACAGCTGTTCCAAAATGTCATGTAACTGAGG
ACACTGGCCATCCTGCTCTCAGAGACACTGACAAACACCTCAATGCCCTGATCTGCCCTTGTTCCAGTTTTACACATCAA
CTCTCGGGACAGAAATACCTTTTACACTTTGGAAGAATTCTCTGCTGAAGACTTTCTACAAAACCTGGCACCGCGTGGCT
CAGTCTCTGATTGCCAACTCTTCCTCCCTCCTCCTCTTGAGAGGGACGAGCTGAAATCCGAAGTTTGTTTTGGAAGCATG
CCCATCTCTCCATGCTGCTGCTGCCCTGTGGAAGGCCCCTCTGCTTGAGCTTAAACAGTAGTGCACAGTTTTCTGCGTAT
ACAGATCCCCAACTCACTGCCTCTAAGTCAGGCAGACCCTGATCAATCTGAACCAAATGTGCACCATCCTCCGATGGCCT
CCCAAGCCAATGTGCCTGCTTCTCTTCCTCTGGTGGGAAGAAAGAACGCTCTACAGAGCACTTAGAGCTTACCATGAAAA
TACTGGGAGAGGCAGCACCTAACACATGTAGAATAGGACTGAATTATTAAGCATGGTGGTATCAGATGATGCAAACAGCC
CATGTCATTTTTTTTCCAGAGGTAGGGACTAATAATTCTCCCACACTAGCACCTACGATCATAGAACAAGTCTTTTAACA
CATCCAGGAGGGAAACCGCTGCCCAGTGGTCTATCCCTTCTCTCCATCCCCTGCTCAAGCCCAGCACTGCATGTCTCTCC
CGGAAGGTCCAGAATGCCTGTGAAATGCTGTAACTTTTATACCCTGTTATAATCAATAAACAGAACTATTTCGTACAAAA
AAAAAAAAAAAAA

RAT 1VL PROTEIN
MGAVMGTFSSLQTKQRRPSKDIAWWYYQYQRDKIEDDLEMTMVCHRPEGLEQLEAQTNFTKRELQVLYRGFKNECPSGVV
NEEETFKQIYAQFFPHGDASTYAHYLFNAFDTTQTGSVKFEDFVTALSILLRGTVHEKLRWTFNLYDINKDGYINKEEMMD
IVKAIYDMMGKYTYPVLKEDTPRQHVDVFFQKMDKNKDGIVTLDEFLESCQEDDNIMRSLQLFQNVM.

Fig. 4

MOUSE 1VL DNA (CD: 77-760)
ATCCACACCGATTTCTTTTCAGGGGAGGGAAGAGACAGGGCCTGGGGTCCCAAGACGCACACAAGTCTTCGCTGCCATGG
GGGCCGTCATGGGCACTTTCTCCTCCCTGCAGACCAAACAAAGGCGACCCTCTAAAGACATCGCCTGGTGGTATTACCAG
TATCAGAGAGACAAGATTGAGGATGAGCTAGAGATGACCATGGTTTGCCACCGGCCTGAGGGACTGGAGCAGCTTGAGGC
ACAGACGAACTTCACCAAGAGAGAACTGCAAGTCTTGTACCGGGGATTCAAAAACGAGTGCCCTAGCGGTGTGGTCAATG
AAGAAACATTCAAGCAGATCTACGCTCAGTTTTTCCCTCACGGAGATGCCAGCACATATGCACATTACCTCTTCAATGCC
TTCGACACCACCCAGACAGGCTCTGTAAAGTTCGAGGACTTTGTGACTGCTCTGTCGATTTTACTGAGAGGGACAGTCCA
TGAAAAACTAAGGTGGACGTTTAATTTGTATGACATCAATAAAGACGGCTACATAAACAAAGAGGAGATGATGGACATAG
TCAAAGCCATCTATGACATGATGGGGAAATACACCTATCCTGTGCTCAAAGAGGACACTCCCAGGCAGCATGTGGATGTC
TTCTTCCAGAAAATGGATAAAAATAAAGATGGCATTGTAACGTTAGATGAATTTCTTGAATCATGTCAGGAGGATGACAA
CATCATGAGATCTCTACAGCTGTTCCAAAATGTCATGTAACTGAGGACACTGGCCATTCTGCTCTCAGAGACACTGACAA
ACACCTTAATGCCCTGATCTGCCCTTGTTCCAATTTTACACACCAACTCTTGGGACAGAAATACCTTTTACACTTTGGAA
GAATTCTCTGCTGAAGACTTTCTACAAAACCTGGCACCACGTGGCTCTGTCTCTGAGGGACGAGCGGAGATCCGACTTTG
TTTTGGAAGCATGCCCATCTCTTCATGCTGCTGCCCTGTGGAAGGCCCCTCTGCTTGAGCTTAATCAATAGTGCACAGTT
TTATGCTTACACATATCCCCAACTCACTGCCTCCAAGTCAGGCAGACTCTGATGAATCTGAGCCAAATGTGCACCATCCT
CCGATGGCCTCCCAAGCCAATGTGCCTGCTTCTCTTCCTCTGGTGGGAAGAAAGAGTGTTCTACGGAACAATTAGAGCTT
ACCATGAAAATATTGGGAGAGGCAGCACCTAACACATGTAGAATAGGACTGAATTATTAAGCATGGTGATATCAGATGAT
GCAAATTGCCCATGTCATTTTTTTCAAAGGTAGGGACAAATGATTCTCCCACACTAGCACCTGTGGTCATAGAGCAAGTC
TCTTAACATGCCCAGAAGGGGAACCACTGTCCAGTGGTCTATCCCTCCTCTCCATCCCCTGCTCAAACCCAGCACTGCAT
GTCCCTCCAAGAAGGTCCAGAATGCCTGCGAAACGCTGTACTTTTATACCCTGTTCTAATCAATAAACAGAACTATTTCG
TACAAAAAAAAAAAAAAAAA

MOUSE 1VL PROTEIN
MGAVMGTFSSLQTKQRRPSKDIAWWYYQYQRDKIEDELEMTMVCHRPEGLEQLEAQTNFTKRELQVLYRGFKNECPSGVV
NEETFKQIYAQFFPHGDASTYAHYLFNAFDTTQTGSVKFEDFVTALSILLRGTVHEKLRWTFNLYDINKDGYINKEEMMD
IVKAIYDMMGKYTYPVLKEDTPRQHVDVFFQKMDKNKDGIVTLDEFLESCQEDDNIMRSLQLFQNVM.

Fig. 5

RAT 1VN DNA (FIRST-PASS, PARTIAL; CD: 345-955)
GTCCGGGCACACAACCCCTGGATTCTTCGGAGAATATGCCGTGACGGTGTTGCCAATTATTAGTTCTCTTGGCTAGCAGA
TGTTTAGGGACTGGTTAAGCCTTTGGAGAAATTACCTTAGGAAAACGGGGAAATAAAAGCAAAGATTACCATGAATTGCA
AGATTACCTAGCAATTGCAAGGTAGGAGGAGAGAGGTGGAGGGCGGAGTAGACAGGAGGGAGGGAGAAAGTGAGAGGAAG
CTAGGCTGGTGGAAATAACCCTGCACTTGGAACAGCGGCAAAGAAGCGCGATTTTCCAGCTTTAAATGCCTGCCCGCGTT
CTGCTTGCCTACCCGGGAACGGAGATGTTGACCCAGGGCGAGTCTGAAGGGCTCCAGACCTTGGGGATAGTAGTGGTCCT
GTGTTCCTCTCTGAAACTACTGCACTACCTCGGGCTGATTGACTTGTCGGATGACAAGATCGAGGATGATCTGGAGATGA
CCATGGTTTGCCATCGGCCTGAGGGACTGGAGCAGCTTGAGGCACAGACGAACTTCACCAAGAGAGAACTGCAAGTCCTT
TACCGGGGATTCAAAAACGAGTGCCCCAGTGGTGTGGTTAACGAAGAGACATTCAAGCNGATCTACGCTCAGTTTTTCCC
TCATGGAGATGCCAGCACATACGCACATTACCTCTTCAATGCCTTCGACACCACCCAGACAGGCTCTGTAAAGTTCGAGG
ACTTTGTGACTGCTCTGTCGATTTTACTGAGAGGAACGGTCCATGAAAAACTGAAGTGGACGTTTAATTTGTACGACATC
AATAAAGACGGCTACATAAACAAAGAGGAGATGATGGACATAGTGAAAGCCATCTATGACATGATGGGGAAATACACCTA
TCTTGTGCTCAAAGAGGACACTTCCAGGCAGCACGTGGACGTCTTCTTCCAGAAAATGGATAAAAATAAAGATGG

RAT 1VN PROTEIN (PARTIAL)
MLTQGESEGLQTLGIVVVLCSSLKLLHYLGLIDLSDDKIEDDLEMTMVCHRPEGLEQLEAQTNFTKRELQVLYRGFKNEC
PSGVVNEETFKXIYAQFFPHGDASTYAHYLFNAFDTTQTGSVKFEDFVTALSILLRGTVHEKLKWTFNLYDINKDGYINK
EEMMDIVKAIYDMMGKYTYLVLKEDTSRQHVDVFFQKMDKNKD

Fig. 6

HUMAN 9QL DNA (CD:207-1019)

CTCACCTGCTGCCTAGTGTTCCCTCTCCTGCTCCAGGACCTCCGGGTAGACCTCAGACCCCGGGCCCATTCCCAGACTCA
GCCTCAGCCCGGACTTCCCCAGCCCCGACAGCACAGTAGGCCGCCAGGGGGCGCCGTGTGAGCGCCCTATCCCGGCCACC
CGGCGCCCCCTCCCACGGCCCGGGCGGGAGCGGGGCGCCGGGGGCCATGCGGGGCCAGGGCCGCAAGGAGAGTTTGTCCG
ATTCCCGAGACCTGGACGGCTCCTACGACCAGCTCACGGGCCACCCTCCAGGGCCCACTAAAAAAGCGCTGAAGCAGCGA
TTCCTCAAGCTGCTGCCGTGCTGCGGGCCCCAAGCCCTGCCCTCAGTCAGTGAAACATTAGCCGCCCCAGCCTCCCTCCG
CCCCCACAGACCCCGCCTGCTGGACCCAGACAGCGTGGACGATGAATTTGAATTGTCCACCGTGTGTCACCGGCCTGAGG
GTCTGGAGCAGCTGCAGGAGCAAACCAAATTCACGCGCAAGGAGTTGCAGGTCCTGTACCGGGGCTTCAAGAACGAATGT
CCCAGCGGAATTGTCAATGAGGAGAACTTCAAGCAGATTTACTCCCAGTTCTTTCCTCAAGGAGACTCCAGCACCTATGC
CACTTTTCTCTTCAATGCCTTTGACACCAACCATGATGGCTCGGTCAGTTTTGAGGACTTTGTGGCTGGTTTGTCCGTGA
TTCTTCGGGGAACTGTAGATGACAGGCTTAATTGGGCCTTCAACCTGTATGACCTTAACAAGGACGGCTGCATCACCAAG
GAGGAAATGCTTGACATCATGAAGTCCATCTATGACATGATGGGCAAGTACACGTACCCTGCACTCCGGGAGGAGGCCCC
AAGGGAACACGTGGAGAGCTTCTTCCAGAAGATGGACAGAAACAAGGATGGTGTGGTGACCATTGAGGAATTCATTGAGT
CTTGTCAAAAGGATGAGAACATCATGAGGTCCATGCAGCTCTTTGACAATGTCATCTAGCCCCCAGGAGAGGGGGTCAGT
GTTTCCTGGGGGACCATGCTCTAACCCTAGTCCAGGCGGACCTCACCCTTCTCTTCCCAGGTCTATCCTCATCCTACGC
CTCCCTGGGGGCTGGAGGGATCCAAGAGCTTGGGGATTCAGTAGTCCAGATCTCTGGAGCTGAAGGGGCCAGAGAGTGGG
CAGAGTGCATCTCGGGGGGTGTTCCCAACTCCCACCAGCTCTCACCCCCTTCCTGCCTGACACCCAGTGTTGAGAGTGCC
CCTCCTGTAGGAATTGAGCGGTTCCCCAC CTCCTACCCTACTCTAGAAACACACTAGAGCGATGTCTCCTGCTATGGTGC
TTCCCCCATCCCTGACCTCATAAACATTTCCCCTAAGACTCCCCTCTCAGAGAGAATGCTCCATTCTTGGCACTGGCTGG
CTTCTCAGACCAGCCATTGAGAGCCCTGTGGGAGGGGGACAAGAATGTATAGGGAGAAATCTTGGGCCTGAGTCAATGGA
TAGGTCCTAGGAGGTGGGTGGGGTTGAGAATAGAAGGGCCTGGACAGATTATGATTGCTCAGGCATACCAGGTTATAGCT
CCAAGTTCCACAGGTCTGCTACCACAGGCCATCAAAATATAAGTTTCCAGGCTTTGCAGAAGACCTTGTCTCCTTAGAAA
TGCCCCAGAAATTTTCCACACCCTCCTCGGTATCCATGGAGAGCCTGGGGCCAGATATCTGGCTCATCTCTGGCATTGCT
TCCTCTCCTTCCTTCCTGCATGTGTTGGTGGTGGTTGTGGTGGGGGAATGTGGATGGGGGATGTCCTGGCTGATGCCTGC
CAAAATTTCATCCCACCCTCCTTGCTTATCGTCCCTGTTTTGAGGGCTATGACTTGAGTTTTTGTTTCCCATGTTCTCTA
TAGACTTGGGACCTTCCTGAACTTGGGGCCTATCACTCCCCACAGTGGATGCCTTAGAAGGGAGAGGGAAGGAGGGAGGC
AGGCATAGC

Fig. 7A

HUMAN 9QL PROTEIN

MRGQGRKESLSDSRDLDGSYDQLTGHPPGPTKKALKQRFLKLLPCCGPQALPSVSETLAAPASLRPHRPRLLDPDSVDDE
FELSTVCHRPEGLEQLQEQTKFTRKELQVLYRGFKNECPSGIVNEENFKQIYSQFFPQGDSSTYATFLFNAFDTNHDGSV
SFEDFVAGLSVILRGTVDDRLNWAFNLYDLNKDGCITKEEMLDIMKSIYDMMGKYTYPALREEAPREHVESFFQKMDRNK
DGVVTIEEFIESCQKDENIMRSMQLFDNVI.

Fig. 7B

RAT 9QL DNA (PARTIAL; CD: 2-775)

CCGAGATCTGGACGGCTCCTATGACCAGCTTACGGGCCACCCTCCAGGGCCCAGTAAAAAAGCCCTGAAGCAGCGTTTCC
TCAAGCTGCTGCCGTGCTGCGGGCCCCAAGCCCTGCCCTCAGTCAGTGAAACATTAGCTGCCCCAGCCTCCCTCCGCCCC
CACAGACCCCGCCCGCTGGACCCAGACAGCGTAGAGGATGAGTTTGAATTATCCACGGTGTGTCACCGACCTGAGGGCCT
GGAACAACTCCAGGAACAGACCAAGTTCACACGCAGAGAGCTGCAGGTCCTGTACCGAGGCTTCAAGAACGAATGCCCCA
GTGGGATTGTCAACGAGGAGAACTTCAAGCAGATTTATTCTCAGTTCTTTCCCCAAGGAGACTCCAGCAACTATGCTACT
TTTCTCTTCAATGCCTTTGACACCAACCACGATGGCTCTGTCAGTTTTGAGGACTTTGTGGCTGGTTTGTCGGTGATTCT
TCGGGGGACCATAGATGATAGACTGAGCTGGGCTTTCAACTTATATGACCCTCAACAAGGACGGCTGTATCACAAAGGAGG
AAATGCTTGACATTATGAAGTCCATCTATGACATGATGGGCAAGTACACATACCCTGCCCTCCGGGAGGAGGCCCCAAGA
GAACACGTGGAGAGCTTCTTCCAGAAGATGGACAGGAACAAGGACGGCGTGGTGACCATCGAGGAATTCATCGAGTCTTG
TCAACAGGACGAGAACATCATGAGGTCCATGCAGCTCTTTGATAATGTCATCTAGCTCCCCAGGGAGAGGGGTTAGTGTG
TCCTAGGGTGACCAGGCTGTAGTCCTAGTCCAGACGAACCTAACCCTCTCTCTCCAGGCCTGTCCTCATCTTACCTGTAC
CCTGGGGGCTGTAGGGATTCAATATCCTGGGGCTTCAGTAGTCCAGATCCCTGAGCTAAGTCACAAAAGTAGGCAAGAGT
AGGCAAGCTAAATCTGGGGGCTTCCCAACCCCCGACAGCTCTCACCCCTTCTCAACTGATACCTAGTGCTGAGGACACCC
CTGGTGTAGGGACCAAGTGGTTCTCCACCTTCTAGTCCCACTCTAGAAACCACATTAGACAGAAGGTCTGGTGCTATGGT
GCTTTCCCCATCCCTAATCTCTTAGATTTTCCTCAAGACTCCCTTCTCAGAGAACACGCTCTGTCCATGTCCCCAGCTGG
GGACATGGACAGAGCGTGTTCTCTAGTTCTAGATCGCGAGCGGCCGC

RAT 9QL PROTEIN (PARTIAL)

RDLDGSYDQLTGHPPGPSKKALKQRFLKLLPCCGPQALPSVSETLAAPASLRPHRPRPLDPDSVEDEFELSTVCHRPEGL
EQLQEQTKFTRRELQVLYRGFKNECPSGIVNEENFKQIYSQFFPQGDSSNYATFLFNAFDTNHDGSVSFEDFVAGLSVIL
RGTIDDRLSWAFNLYDLNKDGCITKEEMLDIMKSIYDMMGKYTYPALREEAPREHVESFFQKMDRNKDGVVTIEEFIESC
QQDENIMRSMQLFDNVI.

Fig. 8

MOUSE 9QL DNA (CD: 181-993)
CGGGACTCTGAGGTGGGCCCTAAAATCCAGCGCTCCCCAGAGAAAAGCCTTGCCAGCCCCTACTCCCGGCCCCCAGCCCC
AGCAGGTCGCTGCGCCGCCAGGGGGCACTGTGTGAGCGCCCTATCCTGGCCACCCGGCGCCCCCTCCCACCGCCCAGGCG
GGAGCGGGGCGCCGGGGGCCATGCGGGGCCAAGGCCGAAAGGAGAGTTTGTCCGAATCCCGAGATTTGGACGGCTCCTAT
GACCAGCTTACGGGCCACCCTCCAGGGCCCAGTAAAAAAGCCCTGAAGCAGCGTTTCCTCAAGCTGCTGCCGTGCTGCGG
GCCCCAAGCCCTGCCCTCAGTCAGTGAAACATTAGCTGCCCCAGCCTCCCTCCGCCCCAGAGACCCCGCCCGCTGGACC
CAGACAGCGTGGAGGATGAGTTTGAACTATCCACGGTGTGCCACCGGCCTGAGGGTCTGGAACAACTCCAGGAACAAACC
AAGTTCACACGCAGAGAGTTGCAGGTCCTGTACAGAGGCTTCAAGAACGAATGTCCCAGCGGAATTGTCAACGAGGAGAA
CTTCAAGCAAATTTATTCTCAGTTCTTTCCCCAAGGAGACTCCAGCAACTACGCTACTTTTCTCTTCAATGCCTTTGACA
CCAACCATGATGGCTCTGTCAGTTTTGAGGACTTTGTGGCTGGTTTGTCAGTGATTCTTCGGGGAACCATAGATGATAGA
CTGAACTGGGCTTTCAACTTATATGACCTCAACAAGGATGGCTGTATCACGAAGGAGGAAATGCTCGACATCATGAAGTC
CATCTATGACATGATGGGCAAGTACACCTACCCTGCCCTCCGGGAGGAGGCCCCGAGGGAACACGTGGAGAGCTTCTTCC
AGAAGATGGACAGAAACAAGGACGGCGTGGTGACCATTGAGGAATTCATTGAGTCTTGTCAACAGGACGAGAACATCATG
AGGTCCATGCAACTCTTTGATAATGTCATCTAGCTCCCCAGGGAGAGGGGTTAGTGTGTCCCAGGGTAACCATGCTGTAG
CCCTAGTCCAGGCAAACCTAACCCTCCTCTCCCCGGGTCTGTCCTCATCCTACCTGTACCCTGGGGCTGTAGGGATTCA
ACATCCTGGCGCTTCAGTAGTCCAGATCCCTGAGCTAAGTGGCGAGAGTAGGCAAGCTAAGTCTTTGGAGGGTGGGTGGG
GGCGCGCAGATTCCCAACCCCCGACGACTCTCACCCCTTTCTCGACTGATACCCAGTGCTGAGGCTACCCCTGGTGTCGG
GAACGACCAAAGTGGTTCTCTGCCTCCCCAGCCCACTCTAGAGACCCACACTAGACGGGAATATCTCCTGCTATGGTGCT
TTCCCCATCCCTGACCGCAGATTTTCCTCCTAAGACTCCCTTCTCAGAGAATATGCTTTTGTCCCTTGTCCCTGGCTGGC
TTTTCAGCCTAGCCTTTGAGGACCCTGTGGGAGGGGAGAATAAGAAAGCAGACAAAATCTTGGCCCTGAGCCAGTGGTTA
GGTCCTAGGAATCAGGCTGGAGTGGAGACCAGAAAGCCTGGGCAGGCTATGAGAGCCCCAGGTTGGCTTGTCACCGCCAG
GTTCCACAGGGCTGCTGCTCTGGGTCAGCAGAGTATGAGTTTCCAGACTTTCCAGAAGGCCTTATGTCCTTAGCAATGTC
CCAGAAATTCACCATACACTTCTCAGTGTCTTAGGATCCAGATGTCCGGTCCATCCCTGAAACCTCTCCCTCCTCCTTGC
TCCTATGGTGGGAGTGGTGGCCAGGGGACGATGAGTGAGCCGGTGTCCTGGATGATGCCTGTCAAGGTCCCACCTACCCT
CCGGCTGTCAAGCCGTTCTGGTGACCCTGTTTGATTCTCCATGACCCCTGTCTAGATGTAGAGGTGTGGAGTGAGTCTAG
TGGCAGCCTTAGGGGAATGGGAAGAACGAGAGGGGCACTCCATCTGAACCCAGTGTGGGGGCATCCATTCGAATCTTTGC
CTGGCTCCCCACAATGCCCTAGGATCCTCTAGGGTCCCCACCCCCACTCTTTAGTCTACCCAGAGATGCTCCAGAGCTCA
CCTAGAGGGCAGGGACCATAGGATCCAGGTCCAACCTGTCATCAGCATCCGGCCATGCTGCTGCTGCTTATTAATAAACC
TGCTTGTCGTTCAGCGCCCCTTCCCAGTCAGCCAGGGTCTGAGGGGAAGGCCCCCACTTTCCCGCCTCCTGTCAGACATT
GTTGACTGCTTTGCATTTTGGGCTCTTCTACCTATATTTTGTATAATAAGAAAGACACCAGATCCAATAAAACACATGGC
TATGCACAAAAAAAAAAAAAAAA

MOUSE 9QL PROTEIN
MRGQGRKESLSESRDLDGSYDQLTGHPPGPSKKALKQRFLKLLPCCGPQALPSVSETLAAPASLRPHRPRPLDPDSVEDE
FELSTVCHRPEGLEQLQEQTKFTRRELQVLYRGFKNECPSGIVNEENFKQIYSQFFPQGDSSNYATFLFNAFDTNHDGSV
SFEDFVAGLSVILRGTIDDRLNWAFNLYDLNKDGCITKEEMLDIMKSITDMMGKYTYPALREEAPREHVESFFQKMDRNK
DGVVTIEEFIESCQQDENIMRSMQLFDNVI

Fig. 9

HUMAN 9QM DNA (CD: 207-965)

```
CTCACCTGCTGCCTAGTGTTCCCTCTCCTGCTCCAGGACCTCCGGGTAGACCTCAGACCCCGGGCCCATTCCCAGACTCA
GCCTCAGCCCGGACTTCCCCAGCCCCGACAGCACAGTAGGCCGCCAGGGGGCGCCGTGTGAGCGCCCTATCCCGGCCACC
CGGCGCCCCCTCCCACGGCCCGGGCGGGAGCGGGGCGCCGGGGGCCATGCGGGGCCAGGGCCGCAAGGAGAGTTTGTCCG
ATTCCCGAGACCTGGACGGCTCCTACGACCAGCTCACGGGCCACCCTCCAGGGCCCACTAAAAAAGCGCTGAAGCAGCGA
TTCCTCAAGCTGCTGCCGTGCTGCGGGCCCCAAGCCCTGCCCTCAGTCAGTGAAAACAGCGTGGACGATGAATTTGAATT
GTCCACCGTGTGTCACCGGCCTGAGGGTCTGGAGCAGCTGCAGGAGCAAACCAAATTCACGCGCAAGGAGTTGCAGGTCC
TGTACCGGGGCTTCAAGAACGAATGTCCCAGCGGAATTGTCAATGAGGAGAACTTCAAGCAGATTTACTCCCAGTTCTTT
CCTCAAGGAGACTCCAGCACCTATGCCACTTTTCTCTTCAATGCCTTTGACACCAACCATGATGGCTCGGTCAGTTTTGA
GGACTTTGTGGCTGGTTTGTCCGTGATTCTTCGGGGAACTGTAGATGACAGGCTTAATTGGGCCTTCAACCTGTATGACC
TTAACAAGGACGGCTGCATCACCAAGGAGGAAATGCTTGACATCATGAAGTCCATCTATGACATGATGGGCAAGTACACG
TACCCTGCACTCCGGGAGGAGGCCCCAAGGGAACACGTGGAGAGCTTCTTCCAGAAGATGGACAGAAACAAGGATGGTGT
GGTGACCATTGAGGAATTCATTGAGTCTTGTGAAAAGGATGAGAACATCATGAGGTCCATGCAGCTCTTTGACAATGTCA
TCTAGCCCCCAGGAGAGGGGGTCAGTGTTTCCTGGGGGGACCATGCTCTAACCCTAGTCCAGGCGGACCTCACCCTTCTC
TTCCCAGGTCTATCCTCATCCTACGCCTCCCTGGGGGCTGGAGGGATCCAAGAGCTTGGGGATTCAGTAGTCCAGATCTC
TGGAGCTGAAGGGGCCAGAGAGTGGGCAGAGTGCATCTCGGGGGGTGTTCCCAACTCCCACCAGCTCTCACCCCCTTCCT
GCCTGACACCCAGTGTTGAGAGTGCCCCTCCTGTAGGAATTGAGCGGTTCCCCACCTCCTACCCTACTCTAGAAACACAC
TAGAGCGATGTCTCCTGCTATGGTGCTTCCCCCATCCCTGACCTCATAAACATTTCCCCTAAGACTCCCCTCTCAGAGAG
AATGCTCCATTCTTGGCACTGGCTGGCTTCTCAGACCAGCCATTGAGAGCCCTGTGGGAGGGGGACAAGAATGTATAGGG
AGAAATCTTGGGCCTGAGTCAATGGATAGGTCCTAGGAGGTGGGTGGGGTTGAGAATAGAAGGGCCTGGACAGATTATGA
TTGCTCAGGCATACCAGGTTATAGCTCCAAGTTCCACAGGTCTGCTACCACAGGCCATCAAAATATAAGTTTCCAGGCTT
TGCAGAAGACCTTGTCTCCTTAGAAATGCCCCAGAAATTTTCCACACCCTCCTCGGTATCCATGGAGAGCCTGGGGCCAG
ATATCTGGCTCATCTCTGGCATTGCTTCCTCTCCTTCCTTCCTGCATGTGTTGGTGGTGGTTGTGGTGGGGAATGTGGA
TGGGGGATGTCCTGGCTGATGCCTGCCAAAATTTCATCCCACCCTCCTTGCTTATCGTCCCTGTTTTGAGGGCTATGACT
TGAGTTTTTGTTTCCCATGTTCTCTATAGACTTGGGACCTTCCTGAACTTGGGGCCTATCACTCCCCACAGTGGATGCCT
TAGAAGGGAGAGGGAAGGAGGGAGGCAGGCATAGC
```

Fig. 10A

HUMAN 9QM PROTEIN

MRGQGRKESLSDSRDLDGSYDQLTGHPPGPTKKALKQRFLKLLPCCGPQALPSVSENSVDDEFELSTVCHRPEGLEQLQE
QTKFTRKELQVLYRGFKNECPSGIVNEENFKQIYSQFFPQGDSSTYATFLFNAFDTNHDGSVSFEDFVAGLSVILRGTVD
DRLNWAFNLYDLNKDGCITKEEMLDIMKSIYDMMGKYTYPALREEAPREHVESFFQKMDRNKDGVVTIEEFIESCQKDEN
IMRSMQLFDNVI.

Fig. 10B

RAT 9QM DNA (CD: 214-972)
CTCACTTGCTGCCCAAGGCTCCTGCTCCTGCCCCAGGACTCTGAGGTGGGCCCTAAAACCCAGCGCTGTCTAAAGAAAAG
CCTTGCCAGCCCCTACTCCCGGCCCCCAACCCCAGCAGGTCGCTGCGCCGCCAGGGGGCGCTGTGTGAGCGCCCTATTCT
GGCCACCCGGCGCCCCCTCCCACGGCCCAGGCGGGAGCGGGGCGCCGGGGGCCATGCGGGGCCAAGGCAGAAAGGAGAGT
TTGTCCGAATCCCGAGATCTGGACGGCTCCTATGACCAGCTTACGGGCCACCCTCCAGGGCCCAGTAAAAAAGCCCTGAA
GCAGCGTTTCCTCAAGCTGCTGCCGTGCTGCGGGCCCCAAGCCCTGCCCTCAGTCAGTGAAAACAGCGTAGAGGATGAGT
TTGAATTATCCACGGTGTGTCACCGACCTGAGGGCCTGGAACAACTCCAGGAACAGACCAAGTTCACACGCAGAGAGCTG
CAGGTCCTGTACCGAGGCTTCAAGAACGAATGCCCCAGTGGGATTGTCAACGAGGAGAACTTCAAGCAGATTTATTCTCA
GTTCTTTCCCCAAGGAGACTCCAGCAACTATGCTACTTTTCTCTTCAATGCCTTTGACACCAACCACGATGGCTCTGTCA
GTTTTGAGGACTTTGTGGCTGGTTTGTCGGTGATTCTTCGGGGACCATAGATGATAGACTGAGCTGGGCTTTCAACTTA
TATGACCTCAACAAGGACGGCTGTATCACAAAGGAGGAAATGCTTGACATTATGAAGTCCATCTATGACATGATGGGCAA
GTACACATACCCTGCCCTCCGGGAGGAGGCCCCAAGAGAACACGTGGAGAGCTTCTTCCAGAAGATGGACAGGAACAAGG
ACGGCGTGGTGACCATCGAGGAATTCATCGAGTCTTGTCAACAGGACGAGAACATCATGAGGTCCATGCAGCTCTTTGAT
AATGTCATCTAGCTCCCCAGGGAGAGGGGTTAGTGTGTCCTAGGGTGACCAGGCTGTAGTCCTAGTCCAGACGAACCTAA
CCCTCTCTCTCCAGGCCTGTCCTCATCTTACCTGTACCCTGGGGGCTGTAGGGATTCAATATCCTGGGGCTTCAGTAGTC
CAGATCCCTGAGCTAAGTCACAAAAGTAGGCAAGAGTAGGCAAGCTAAATCTGGGGGCTTCCCAACCCCCGACAGCTCTC
ACCCCTTCTCAACTGATACCTAGTGCTGAGGACACCCCTGGTGTAGGGACCAAGTGGTTCTCCACCTTCTAGTCCCACTC
TAGAAACCACATTAGACAGAAGGTCTCCTGCTATGGTGCTTTCCCCATCCCTAATCTCTTAGATTTTCCTCAAGACTCCC
TTCTCAGAGAACACGCTCTGTCCATGTCCCCAGCTGGCTTCTCAGCCTAGCCTTTGAGGGCCCTGTGGGGAGGCGGGGAC
AAGAAAGCAGAAAAGTCTTGGCCCCGAGCCAGTGGTTAGGTCCTAGGAATTGGCTGGAGTGGAGGCCAGAAAGCCTGGGC
AGATGATGAGAGCCCAGCTGGGCTGTCACTGCAGGTTCCGGGGCCTACAGCCCTGGGTCAGCAGAGTATGAGTTCCCAGA
CTTTCCAGAAGGTCCTTAGCAATGTCCCAGAAATTCACCGTACACTTCTCAGTGTCTTAGGAGGGCCCGGGATCCAGATG
TCTGGTTCATCCCTGAATCCTCTCCCTCCTTCTTGCTCGTATGGTGGGAGTGGTGGCCAGGGGAAGATGAGTGGTGTCCC
GGATGATGCCTGTCAAGGTCCCACCTCCCCTCCGGCTGTTCTCATGACAGCTGTTTGGTTCTCCATGACCCCTATCTAGA
TGTAGAGGCATGGAGTGAGTCAGGGATTTCCCGAACTTGAGTTTTACCACTCCTCCTAGTGGCTGCCTTAGGGGAATGGG
AAGAACCCAGTGTGGGGCACCCATTAGAATCTTTGCCCGGCTCCTCACAATGCCCTAGGGTCCCCTAGGGTACCCGCTC
CCTCTGTTTAGTCTACCCAGAGATGCTCCTGAGCTCACCTAGAGGGTAGGGACGGTAGGCTCCAGGTCCAACCTCTCCAG
GTCAGCACCCTGCCATGCTGCTGCTCCTCATTAACAAACCTGCTTGTCTCCTCCTGCGCCCCTTCTCAGTCAGCCAGGGT
CTGAGGGGAAGGGCCTCCCGTTTCCCCATCCGTCAGACATGGTTGACTGCTTTGCATTTTGGGCTCTTCTATCTATTTTG
TAAAATAAGACATCAGATCCAATAAAACACACGGCTATGCACAAAAAAAAAAAAAAAAAA

RAT 9QM PROTEIN
MRGQGRKESLSESRDLDGSYDQLTGHPPGPSKKALKQRFLKLLPCCGPQALPSVSENSVEDEFELSTVCHRPEGLEQLQE
QTKFTRRELQVLYRGFKNECPSGIVNEENFKQIYSQFFPQGDSSNYATFLFNAFDTNHDGSVSFEDFVAGLSVILRGTID
DRLSWAFNLYDLNKDGCITKEEMLDIMKSIYDMMGKYTYPALREEAPREHVESFFQKMDRNKDGVVTIEEFIESCQQDEN
IMRSMQLFDNVI.

Fig. 11

HUMAN 9QS DNA (CD: 207-869)

CTCACCTGCTGCCTAGTGTTCCCTCTCCTGCTCCAGGACCTCCGGGTAGACCTCAGACCCCGGGCCCATTCCCAGACTCA
GCCTCAGCCCGGACTTCCCCAGCCCCGACAGCACAGTAGGCCGCCAGGGGGCGCCGTGTGAGCGCCCTATCCCGGCCACC
CGGCGCCCCTCCCACGGCCCGGGCGGGAGCGGGGCGCCGGGGGCCATGCGGGGCCAGGGCCGCAAGGAGAGTTTGTCCG
ATTCCCGAGACCTGGACGGCTCCTACGACCAGCTCACGGACAGCGTGGACGATGAATTTGAATTGTCCACCGTGTGTCAC
CGGCCTGAGGGTCTGGAGCAGCTGCAGGAGCAAACCAAATTCACGCGCAAGGAGTTGCAGGTCCTGTACCGGGGCTTCAA
GAACGAATGTCCCAGCGGAATTGTCAATGAGGAGAACTTCAAGCAGATTTACTCCCAGTTCTTTCCTCAAGGAGACTCCA
GCACCTATGCCACTTTTCTCTTCAATGCCTTTGACACCAACCATGATGGCTCGGTCAGTTTTGAGGACTTTGTGGCTGGT
TTGTCCGTGATTCTTCGGGGAACTGTAGATGACAGGCTTAATTGGGCCTTCAACCTGTATGACCTTAACAAGGACGGCTG
CATCACCAAGGAGGAAATGCTTGACATCATGAAGTCCATCTATGACATGATGGGCAAGTACACGTACCCTGCACTCCGGG
AGGAGGCCCCAAGGGAACACGTGGAGAGCTTCTTCCAGAAGATGGACAGAAACAAGGATGGTGTGGTGACCATTGAGGAA
TTCATTGAGTCTTGTCAAAAGGATGAGAACATCATGAGGTCCATGCAGCTCTTTGACAATGTCATCTAGCCCCCAGGAGA
GGGGGTCAGTGTTTCCTGGGGGGACCATGCTCTAACCCTAGTCCAGGCGGACCTCACCCTTCTCTTCCCAGGTCTATCCT
CATCCTACGCCTCCCTGGGGGCTGGAGGGATCCAAGAGCTTGGGGATTCAGTAGTCCAGATCTCTGGAGCTGAAGGGGCC
AGAGAGTGGGCAGAGTGCATCTCGGGGGGTGTTCCCAACTCCCACCAGCTCTCACCCCCTTCCTGCCTGACACCCAGTGT
TGAGAGTGCCCCTCCTGTAGGAATTGAGCGGTTCCCCACCTCCTACCCTACTCTAGAAACACACTAGAGCGATGTCTCCT
GCTATGGTGCTTCCCCCATCCCTGACCTCATAAACATTTCCCCTAAGACTCCCCTCTCAGAGAGAATGCTCCATTCTTGG
CACTGGCTGGCTTCTCAGACCAGCCATTGAGAGCCCTGTGGGAGGGGGACAAGAATGTATAGGGAGAAATCTTGGGCCTG
AGTCAATGGATAGGTCCTAGGAGGTGGGTGGGGTTGAGAATAGAAGGGCCTGGACAGATTATGATTGCTCAGGCATACCA
GGTTATAGCTCCAAGTTCCACAGGTCTGCTACCACAGGCCATCAAAATATAAGTTTCCAGGCTTTGCAGAAGACCTTGTC
TCCTTAGAAATGCCCCAGAAATTTTCCACACCCTCCTCGGTATCCATGGAGAGCCTGGGGCCAGATATCTGGCTCATCTC
TGGCATTGCTTCCTCTCCTTCCTTCCTGCATGTGTTGGTGGTGGTTGTGGTGGGGGAATGTGGATGGGGGATGTCCTGGC
TGATGCCTGCCAAAATTTCATCCCACCCTCCTTGCTTATCGTCCCTGTTTTGAGGGCTATGACTTGAGTTTTTGTTTCCC
ATGTTCTCTATAGACTTGGGACCTTCCTGAACTTGGGGCCTATCACTCCCCACAGTGGATGCCTTAGAAGGGAGAGGGAA
GGAGGGAGGCAGGCATAGC

Fig. 12

MONKEY 9QS DNA (CD: 133-795)
CCCACGCGTCCGCCCACGCGTCCGCGGACGCGTGGGGTGCACTAGGCCGCCAGGGGGCGCCGTGTGAGCGCCCTATCCCG
GCCACCCGGCGCCCCCTCCCACGGACCGGGCGGGAGCGGGGCGCCGGGGGCCATGCGGGGCCAGGGCCGCAAGGAGAGTT
TGTCCGATTCCCGAGACCTGGACGGATCCTACGACCAGCTCACGGACAGCGTGGAGGATGAATTTGAATTGTCCACCGTG
TGTCACCGGCCTGAGGGTCTGGAGCAGCTGCAGGAGCAAACCAAATTCACGCGCAAGGAGTTGCAGGTCCTGTACCGGGG
CTTCAAGAACGAATGTCCGAGCGGAATTGTCAATGAGGAGAACTTCAAGCAAATTTACTCCCAGTTCTTTCCTCAAGGAG
ACTCCAGCACCTATGCCACTTTTCTCTTCAATGCCTTTGACACCAACCATGATGGCTCGGTCAGTTTTGAGGACTTTGTG
GCTGGTTTGTCCGTGATTCTTCGGGGAACTGTAGATGACAGGCTTAATTGGGCCTTCAACTTGTATGACCTCAACAAGGA
CGGCTGCATCACCAAGGAGGAAATGCTTGACATCATGAAGTCCATCTATGACATGATGGGCAAGTACACATACCCTGCAC
TCCGGGAGGAGGCCCCAAGGGAACATGTGGAGAACTTCTTCCAGAAGATGGACAGAAACAAGGATGGCGTGGTGACCATT
GAGGAATTCATTGAGTCTTGTCAAAAGGATGAGAACATCATGAGGTCCATGCAGCTCTTTGACAATGTCATCTAGCCCCC
AGGAGAGGGGGTCAGTGTTTCCTGGGGGGACCATGCTCTAACCCTAGTCCAGGTGGACCTCACCCTTCTCTTCCCAGGTC
TATCCTTGTCCTAGGCCTCCCTGGGGGCTGGAGGGATCCAAGAGCTTGGGGATTCAGTAGTCCAGATCTCTGGAGCTGAA
GGGGCCAGAGAGTGGGCAGAGTGCATCTTGGGGGGTGTTCCCAACTCCCACCAGCTTTCACCCGCTTCCTGCCTGACACC
CAGTGTTGAGAGTGCCCCTCCTGTAGGAACTGAGTGGTTCCCCACCTCCTACCCCCACTCTAGAAACACACTAGACAGAT
GTCTCCTGCTATGGTGCTTCCCCCATCCCTGACTTCATAAACATTTCCCCTAAAACTCCCTTCTCAGAGAGAATGCTCCA
TTCTTGGCACTGGCTGGCTTCTCAGACCAGCCTTTGAGAGCCCTGTGGGAGGGGGACAAGAATGTATAGGGGAGAAATCT
TGGGCCTGAGTCAATGGATAGGTCCTAGGAGGTGGCTGGGGTTGAGAATAGAAAGGCCTGGACACAATGTGATTGCTCAG
GCATACCAAGTTATAGCTCCAAGTTCCACAGGTCTGCTACCACAGGCCATCAAAATATAAGTTTCCAGGCTTTGCAGAAG
ACCTTGTCTCCTTGGAAATGCCCCAGATATTTTCCATACCCTCCTCGATATCCATGGAGAGCCTGGGGCTAGATATCTGG
CATATCCCTGGCATTGCTTCCTCTCCTTCCTTCCTGCATGTGTTGGTGGTGGTTGTGGCAGGGGAATGTGGATAGGAGAT
GTCCTGGCAGATGCCTGCCAAAGTTTCATCCCACCCTCCCTGCTCATCGCCCCTGTTTTGAGGGCTGTGACTTGAGTTTT
TGTTTCCCATGTTCTCTATAGACTTGGGACCTTCCTGAACTTGGGGCCTATCACTCCCCACAGTGGATGCCTTAGAAGGG
AGAGGGAAGGAGGGAGGCAGGCATAGCATCTGAACCCAGTGTGGGGGCATTCACTAGGATCTTCAATCAACCCGGGCTCT
CCCCAACCCCCCAGATAACCTCCTCAGTTCCCTAGAGTCTCCTCTTGCTCTACTCAATCTACCCAGAGATGCCCCTTAGC
ACACTCAGAGGGCAGGGACCATAGGACCCAGGTTCCAACCCCATTGTCAGCACCCCAGCCATGCTGCCATCCCTTAGCAC
ACCTGCTCGTCCCATTCAGCTTACCCTCCCAGTCAGCCAGAATCTGAGGGGAGGGCCCCAGAGAGCCCCCTTCCCCATC
AGAAGACTGTTGACTGCTTTGCATTTTGGGCTCTTCTATATATTTTGTAAAATAAGAACTATACCAGATCTAATAAAACA
CAATGGCTATGCAAAAAAAAAAAAAAAAAAA

MONKEY 9QS PROTEIN
MRGQGRKESLSDSRDLDGSYDQLTDSVEDEFELSTVCHRPEGLEQLQEQTKFTRKELQVLYRGFKNECPSGIVNEENFKQ
IYSQFFPQGDSSTYATFLFNAFDTNHDGSVSFEDFVAGLSVILRGTVDDRLNWAFNLYDLNKDGCITKEEMLDIMKSIYD
MMGKYTYPALREEAPREHVENFFQKMDRNKDGVVTIEEFIESCQKDENIMRSMQLFDNVI

Fig. 13

RAT 9QC DNA (CD: 208-966)

TGCTGCCCAAGGCTCCTGCTCCTGCCCCAGGACTCTGAGGTGGGCCCTAAAACCCAGCGCTCTCTAAAGAAAAGCCTTGC
CAGCCCCTACTCCCGGCCCCCAACCCCAGCAGGTCGCTGCGCCGCCAGGGGGCGCTGTGTGAGCGCCCTATTCTGGCCAC
CCGGCGCCCCCTCCCACGGCCCAGGCGGGAGCGGGGCGCCGGGGGCCATGCGGGGCCAAGGCAGAAAGGAGTTTGTCC
GAATCCCGAGATCTGGACGGCTCCTATGACCAGCTTACGGGCCACCCTCCAGGGCCCAGTAAAAAAGCCCTGAAGCAGCG
TTTCCTCAAGCTGCTGCCGTGCTGCGGGCCCCAAGCCCTGCCCTCAGTCAGTGAAAACAGCGTAGAGGATGAGTTTGAAT
TATCCACGGTGTGTCACCGACCTGAGGGCCTGGAACAACTCCAGGAACAGACCAAGTTCACACGCAGAGAGCTGCAGGTC
CTGTACCGAGGCTTCAAGAACGAATGCCCCAGTGGGATTGTCAACGAGGAGAACTTCAAGCAGATTTATTCTCAGTTCTT
TCCCCAAGGAGACTCCAGCAACTATGCTACTTTTCTCTTCAATGCCTTTGACACCAACCACGATGGCTCTGTCAGTTTTG
AGGACTTTGTGGCTGGTTTGTCGGTGATTCTTCGGGGGACCATAGATGATAGACTGAGCTGGGCTTTCAACTTATATGAC
CTCAACAAGGACGGCTGTATCACAAAGGAGGAAATGCTTGACATTATGAAGTCCATCTATGACATGATGGGCAAGTACAC
ATACCCTGCCCTCCGGGAGGAGGCCCCAAGAGAACACGTGGAGAGCTTCTTCCAGAAGATGGACAGGAACAAGGACGGCG
TGGTGACCATCGAGGAATTCATCGAGTCTTGTCAACAGGACGAGAACATCATGAGGTCCATGCAGCTCTCACCCCTTCTC
AACTGATACCTAGTGCTGAGGACACCCCTGGTGTAGGGACCAAGTGGTTCTCCACCTTCTAGTCCCACTCTAGAAACCAC
ATTAGACAGAAGGTCTCCTGCTATGGTGCTTTCCCCATCCCTAATCTCTTAGATTTTCCTCAAGACTCCCTTCTCAGAGA
ACACGCTCTGTCCATGTCCCCAGCTGGCTTCTCAGCCTAGCCTTTGAGGGCCCTGTGGGGAGGCGGGGACAAGAAAGCAG
AAAAGTCTTGGCCCCGAGCCAGTGGTTAGGTCCTAGGAATTGGCTGGAGTGGAGGCCAGAAAGCCTGGGCAGATGATGAG
AGCCCAGCTGGGCTGTCACTGCAGGTTCCGGGGCCTACAGCCCTGGGTCAGCAGAGTATGAGTTCCCAGACTTTCCAGAA
GGTCCTTAGCAATGTCCCAGAAATTCACCGTACACTTCTCAGTGTCTTAGGAGGGCCCGGGATCCAGATGTCTGGTTCAT
CCCTGAATCCTCTCCCTCCTTCTTGCTCGTATGGTGGGAGTGGTGGCCAGGGGAAGATGAGTGGTGTCCCGGATGATGCC
TGTCAAGGTCCCACCTCCCCTCCGGCTGTTCTCATGACAGCTGTTTGGTTCTCCATGACCCCTATCTAGATGTAGAGGCA
TGGAGTGAGTCAGGGATTTCCCGAACTTGAGTTTTACCACTCCTCCTAGTGGCTGCCTTAGGGGAATGGGAAGAACCCAG
TGTGGGGGCACCCATTAGAATCTTTGCCCGGCTCCTCACAATGCCCTAGGGTCCCCTAGGGTACCCGCTCCCTCTGTTTA
GTCTACCCAGAGATGCTCCTGAGCTCACCTAGAGGGTAGGGACGGTAGGCTCCAGGTCCAACCTCTCCAGGTCAGCACCC
TGCCATGCTGCTGCTCCTCATTAACAAACCTGCTTGTCTCCTCCTGCGCCCCTTCTCAGTCAGCCAGGGTCTGAGGGGAA
GGGCCTCCCGTTTCCCCATCCGTCAGACATGGTTGACTGCTTTGCATTTGGGCTCTTCTATCTATTTTGTAAAATAAGA
CATCAGATCCAATAAAACACACGGCTATGCACAAAAAAAAAAAAAAAAAAAAAAAAAA

RAT 9QC PROTEIN

MRGQGRKESLSESRDLDGSTDQLTGHPPGPSKKALKQRFLKLLPCCGPQALPSVSENSVEDEFELSTVCHRPEGLEQLQE
QTKFTRRELQVLYRGFKNECPSGIVNEENFKQIYSQFFPQGDSSNYATFLFNAFDTNHDGSVSFEDFVAGLSVILRGTID
DRLSWAFNLYDLNKDGCITKEEMLDIMKSIYDMMGKYTYPALREEAPREHVESFFQKMDRNKDGVVTIEEFIESCQQDEN
IMRSMQLSPLLN.

Fig. 14

RAT 8T (9Q SPLICE VARAIANT) DNA (MAY NOT BE FULL LENGTH, CD: 1-678)
ATGAACCACTGCCCTCGCAGGTGCCGGAGCCCGTTGGGGCAGGCAGCTCGATCTCTCTACCAGTTGGTAACTGGGTCGCT
GTCGCCAGACAGCGTAGAGGATGAGTTTGAATTATCCACGGTGTGTCACCGACCTGAGGGCCTGGAACAACTCCAGGAAC
AGACCAAGTTCACACGCAGAGAGCTGCAGGTCCTGTACCGAGGCTTCAAGAACGAATGCCCCAGTGGGATTGTCAACGAG
GAGAACTTCAAGCAGATTTATTCTCAGTTCTTTCCCCAAGGAGACTCCAGCAACTATGCTACTTTTCTCTTCAATGCCTT
TGACACCAACCACGATGGCTCTGTCAGTTTTGAGGACTTTGTGGCTGGTTTGTCGGTGATTCTTCGGGGGACCATAGATG
ATAGACTGAGCTGGGCTTTCAACTTATATGACCTCAACAAGGACGGCTGTATCACAAAGGAGGAAATGCTTGACATTATG
AAGTCCATCTATGACATGATGGGCAAGTACACATACCCTGCCCTCCGGGAGGAGGCCCCAAGAGAACACGTGGAGAGCTT
CTTCCAGAAGATGGACAGGAACAAGGACGGCGTGGTGACCATCGAGGAATTCATCGAGTCTTGTCAACAGGACGAGAACA
TCATGAGGTCCATGCAGCTCTTTGATAATGTCATCTAGCTCCCCAGGGAGAGGGGTTAGTGTGTCCTAGGGTGACCAGGC
TGTAGTCCTAGTCCAGACGAACCTAACCCTCTCTCTCCAGGCCTGTCCTCATCTTACCTGTACCCTGGGGGCTGTAGGGA
TTCAATATCCTGGGGCTTCAGTAGTCCAGATCCCTGAGCTAAGTCACAAAAGTAGGCAAGAGTAGGCAAGCTAAATCTGG
GGGCTTCCCAACCCCCGACAGCTCTCACCCCTTCTCAACTGATACCTAGTGCTGAGGACACCCCTGGTGTAGGGACCAAG
TGGTTCTCCACCTTCTAGTCCCACTCTAGAAACCACATTAGACAGAAGGTCTCCTGCTATGGTGCTTTCCCCATCCCTAA
TCTCTTAGATTTTCCTCAAGACTCCCTTCTCAGAGAACACGCTCTGTCCATGTCCCCAGCTGGCTTCTCAGCCTAGCCTT
TGAGGGCCCTGTGGGGAGGCGGGGACAAGAAAGCAGAAAAGTCTTGGCCCCGAGCTAGTGGTTAGGTCCTAGGAATTGGC
TGGAGTGGAGGCCAGAAAGCCTGGGCAGATGATGAGAGCCCAGCTGGGCTGTCACTGCAGGTTCCAGGGCCTACAGCCCT
GGGTCAGCAGAGTATGAGTTCCCAGACTTTCCAGAAGGTCCTTAGCAATGTCCCAGAAATTCACCATACACTTCTCAGTG
TCCCGGATGATGCCTGTCAAGGTCCCACCTCCCCTCCGGCTGTTCTCATGACAGCTGTTTGGTTCTCCATGACCCCTATC
TAGATGTAGAGGCATGGAGTGAGTCAGGGATTTCCCGAACTTGAGTTTTACCACTCCTCCTAGTGGCTGCCTTAGGGGAA
TGGGAAGAACCCAGTGTGGGGGCACCCATTAGAATCTTTGCCCGGTTCCTCACAATGCCCTAGGGTCCCCTAGGGTACCC
GCTCCCTCTGTTTAGTCTACCCAGAGATGCTCCTGAGCTCACCTAGAGGGTAGGGACGGTAGGCTCCAGGTCCAACCTCT
CCAGGTCAGCACCCTGCCATGCTGCTGCTCCTCATTAACAAACCTGCTTGTCTCCTCCTGCGCCCCTTCTCAGTCAGCCA
GGGTCTGAGGGGAAGGGCCTCCCGTTTCCCCATCCGTCAGACATGGTTGACTGCTTTGCATTTTGGGCTCTTCTATCTAT
TTTGTAAAATAAGACATCAGATCCAATAAAACACACGGCTATGCACAAAAAAAAAAAAAAAAAAAA

RAT 8T (9Q SPLICE VARAIANT) PROTEIN (MAY NOT BE FULL LENGTH)
MNHCPRRCRSPLGQAARSLYQLVTGSLSPDSVEDEFELSTVCHRPEGLEQLQEQTKFTRRELQVLYRGFKNECPSGIVNE
ENFKQIYSQFFPQGDSSNYATFLFNAFDTNHDGSVSFEDFVAGLSVILRGTIDDRLSWAFNLYDLNKDGCITKEEMLDIM
KSIYDMMGKYTYPALREEAPREHVESFFQKMDRNKDGVVTIEEFIESCQQDENIMRSMQLFDNVI

Fig. 15

HUMAN P19 (hP195) DNA (partial, CD: 20-619)

GTTTTCTTCAGCGCCCAGGATGCAGCCGGCTAAGGAAGTGACAAAGGCGTCGGACGGCAGCCTCCTGGGGGACCTCGGGC
ACACACCACTTAGCAAGAAGGAGGGTATCAAGTGGCAGAGGCCGAGGCTCAGCCGCCAGGCTTTGATGAGATGCTGCCTG
GTCAAGTGGATCCTGTCCAGCACAGCCCCACAGGGCTCAGATAGCAGCGACAGTGAGCTGGAGCTGTCCACGGTGCGCCA
CCAGCCAGAGGGGCTGGACCAGCTGCAGGCCCAGACCAAGTTCACCAAGAAGGAGCTGCAGTCTCTCTACAGGGGCTTTA
AGAATGAGTGTCCCACGGGCCTGGTGGACGAAGACACCTTCAAACTCATTTACGCGCAGTTCTTCCCTCAGGGAGATGCC
ACCACCTATGCACACTTCCTCTTCAACGCCTTTGATGCGGACGGGAACGGGGCCATCCACTTTGAGGACTTTGTGGTTGG
CCTCTCCATCCTGCTGCGGGGCACAGTCCACGAGAAGCTCAAGTGGGCCTTTAATCTCTACGACATTAACAAGGATGGCT
ACATCACCAAAGAGGAGATGCTGGCCATCATGAAGTCCATCTATGACATGATGGGCCGC

HUMAN P19 (hP195) PROTEIN (PARTIAL)

MQPAKEVTKASDGSLLGDLGHTPLSKKEGIKWQRPRLSRQALMRCCLVKWILSSTAPQGSDSSDSELELSTVRHQPEGLD
QLQAQTKFTKKELQSLYRGFKNECPTGLVDEDTFKLIYAQFFPQGDATTYAHFLFNAFDADGNGAIHFEDFVVGLSILLR
GTVHEKLKWAFNLYDINKDGYITKEEMLAIMKSIYDMMGR

Fig. 16

RAT P19 DNA (FIRST-PASS, PARTIAL; CD: 1-330)
TTTGAGGACTTTGTGGTTGGGCTCTCCATCCTGCTTCGAGGGACCGTCCATGAGAAGCTCAAGTGGGCCTTCAATCTCTA
CGACATCAACAAGGACGGTTACATCACCAAAGAGGAGATGCTGGCCATCATGAAGTCCATCTACGACATGATGGGCCGCC
ACACCTACCCTATCCTGCGGGAGGACGCACCTCTGGAGCATGTGGAGAGGTTCTTCCAGAAAATGGACAGGAACCAGGAT
GGAGTAGTGACTATTGATGAATTTCTGGAGACTTGTCAGAAGGACGAGAACATCATGAGCTCCATGCAGCTGTTTGAGAA
CGTCATCTAGGACATGTAGGAGGGGACCCTGGGTGGCCATGGGTTCTCAACCCAGAGAAGCCTCAATCCTGACAGGAGAA
GCCTCTATGAGAAACATTTTTCTAATATATTTGCAAAAAGTG

RAT P19 PROTEIN (PARTIAL)
FEDFVVGLSILLRGTVHEKLKWAFNLYDINKDGYITKEEMLAIMKSIYDMMGRHTYPILREDAPLEHVERFFQKMDRNQD
GVVTIDEFLETCQKDENIMSSMQLFENVI

Fig. 17

MOUSE P19 DNA (CD: 49-819)
CGGGCTGCAAAGCGGGAAGATTAGTGACGGTCCCTTTCAGCAGCAGAGATGCAGAGGACCAAGGAAGCCGTGAAGGCATC
AGATGGCAACCTCCTGGGAGATCCTGGGCGCATACCACTGAGCAAGAGGGAAAGCATCAAGTGGCAAAGGCCACGGTTCA
CCCGCCAGGCCCTGATGCGTTGCTGCTTAATCAAGTGGATCCTGTCCAGTGCTGCCCCACAAGGCTCAGACAGCAGTGAC
AGTGAACTGGAGTTATCCACGGTGCGCCATCAGCCAGAGGGCTTGGACCAGCTACAAGCTCAGACCAAGTTCACCAAGAA
GGAGCTGCAGTCCCTTTACCGAGGCTTCAAGAATGAGTGTCCCACAGGCCTGGTGGATGAAGACACCTTCAAACTCATTT
ATTCCCAGTTCTTCCCTCAGGGAGATGCCACCACCTATGCACACTTCCTCTTCAATGCCTTTGATGCTGATGGGAACGGG
GCCATCCACTTTGAGGACTTTGTGGTTGGGCTCTCCATCCTGCTTCGAGGGACGGTCCATGAGAAGCTCAAGTGGGCCTT
CAATCTCTATGACATTAACAAGGATGGTTGCATCACCAAGGAGGAGATGCTGGCCATCATGAAGTCCATCTACGACATGA
TGGGCCGCCACACCTACCCCATCCTGCGGGAGGATGCACCCCTGGAGCATGTGGAGAGGTTCTTTCAGAAAATGGACAGG
AACCAGGATGGAGTGGTGACCATTGATGAATTTCTGGAGACTTGTCAGAAGGATGAGAACATCATGAACTCCATGCAGCT
GTTTGAGAACGTCATCTAGGACATGTGGGAGGGGACCCCAGTGGTCATTGCTTCTCAACCCAGAGAAGCCTCAATCCTGA
CAGGAGAAGCCTCTATGAGAAACATTTTTCTAATATATTTGCAAAAAGTGAGCAGTTTACTTCCAAGACACAGCCACCGT
CACACACAGACACAGACATACAGACACACACACACACACACACATGGTTCCTCTGGCTTGGCCAAGGAAGTGGCAGCC
AGAAGGCACCCCCGCCTATTCCTAGGTCAATAAAAAAGGCTGCCTCTGGGATGGCCAGCCCTGGCTAGATGTTACCCACA
AGGAACTCAGAGATCGAGAGGACCAGGTCTACAAAGCTAAGGTCCCTGTGTCTTTTCTACCACTCGGGAGATCAAACTAC
TCCCTGCCTATGGACCCATGCTCTTAGGAAGCTCCCAGAAACTCCAAGGGGACAAAGAGGGGAGAGGTCTATAGGAAGAA
ATGGTTTTGGAAGCTGGGCTTGCAGCCTTATGCTAATGATCACCTGGGGTCCTGGAACCCGAGTGCCAGGCTACCTACTA
TGCCGTGAGCTTAGATAGTGAGGGGCCATTGGACTAAGACCTCCTGTAAGAGTGGGGCAGGATTGAGGTTTTTGGAGAAA
CTGAGGAAACAATTTGTCCATACCACTGGGTGAAGACTGCTGGCCAGTGGGAATGTGGCTGGTGGAGATTTCCCAACTTC
CAGCACCAGGATGGCCTCTCCAAGGTCCTCTTTGATTCCCTGGGGAGATCACCTGGCTCATAGACTGACAACCAGGGAAC
TGGGCTGAAATGGGAGGTCTGGTAGGGGGCATCCCCCTCCTTTTCCCTGGCCACTTGCCACCCAGTTCCTTAACACAGTG
GATCGGCCACACCTCTGTGGCTGCCCTTGAACAGACTCATCCCGACCAAGACAAAAAAGCACAAACTCCTAGCAGCTCAG
GCCAAGCCCACAAGGGAAGGCCTGGGTCCCTGCAGCCCTGATTCAGTGGCCGAGGAAGACGCTCAGACATCCATCCTGTA
CCTCGGAGCCTTGGGGGTCTCACAGCCCTTTCCCAGCCCAGCTCGCCAACATTCTAAAGCACAAACCTGCGGATTCTGCT
TGCTTGGGCTGCGCCCTGGGGATTGAAGGCCACTGTTAACCCTAAGCTGGAGCTAGCCCTGAGGGCTGGGGACCTGTGAC
CAGGCAACAGGTCAGCAGACCCTCAGGAGGAGAGAGAGCTGTTCCTGCCTCCCCAGGCCTCGCCCAGAAGGAACAGTGTC
CCAAGAAGCATGTTTCCTGGAGGAACATCCCCACAAAAGTACATTCCATCATCTGAAGCCCGGTCTCTGCTCAGGCCTGC
CTCTGAAAGTCCACGTGTGTTCCCCAGAAGGCCAGCCCCAAGATAAGGGAGGTCCTTAGAGGAAGGACAGGGTGACAACA
CCCCTATACACAGGTGGACCCCCCCTCTGAGGACTGTACTGACCCCATCTCCATCCTGACCGGGGCCTTCCTTTACCCGA
TCTACAGACCACCAGTTCTCCCTGGCTCAGGGACCCCCTGTCCCCAGTCTGACTCTTCCCATCGAGGTCCCTGTCTTGT
GAAAAGCCAAGGCCACGGGAAAAGGCCACCACTCTAACCTGCTGCATCCCTTAGCCTCTGGCTGCACGCCCAACCTGGAG
GGGTCTGTCCCCTTTGCAGGGACACAGACTGGCCGCATGTCCGCATGGCAGAAGCGTCTCCCTTGGGTGCAGCCTGGAAG
GGTGGTTTCTGTCTCAGCGCCCACCAATATTCAGTCCTATATATTTTAATAAAAGAAACTTGACAAAGGAAAAAAAAAAA
AAAA

Fig. 18

PUTATIVE ADDITIONAL HUMAN PARALOG (W28559) DNA (FIRST-PASS, PARTIAL; CD: 2-380)

GGCTNCACCCTGCGTCCCCAGACATGAATGTGAGGAGGGTGGAAAGCATTTCGGGCTCAGCTGGAGGAGGCCAGCTCTAC

AAGGCGGTTTCCTGTACGCTCAGAACAGCACCAAGCGCAGCATTAAAGAGCGGCTCATGAAGCTCTTGCCCTGCTCAGCT

GCCNAAACGTCGTCTCCTGCTATTCNAAACAGCGTGGAAGATGAACTGGAGATGGCCACCGTCAGGCATCGGCCCGAAGC

CCTTGAGCTTCTGGAAGCCCAGAGCAAATTTACCAAGAAAGAGCTTCAGATCCTTTACAGAGGATTTAAGAACGAATGCC

CCAGTGGTGNTGTTAATGAAGAAACCTTCAAAGAGATTACTCGCAGTCTTTCCACAGAAA

PUTATIVE ADDITIONAL HUMAN PARALOG (W28559) PROTEIN (PARTIAL)
AXPCVPRHECEEGGKHFGLSWRRPALQGGFLYAQNSTKRSIKERLMKLLPCSAAXTSSPAIXNSVEDELEMATVRHRPEA
LELLEAQSKFTKKELQILYRGFKNECPSGXVNEETFKEITRSLSTE

Fig. 19

P193 (AA349365) DNA (CD: 2-127, partial)
```
TGAAAGGTTCTTCGAGAAAATGGACCGGAACCAGGATGGGGTAGTGACCATTGAAGAGTTCCTGGAGGC
CTGTCAGAAGGATGAGAACATCATGAGCTCCATGCAGCTGTTTGAGAATGTCATCTAGGACACGTCCAAA
GGAGTGCATGGCCACAGCCACCTCCACCCCCAAGAAACCTCCATCCTGCCAGGAGCAGCCTCCAAGAAA
CTTTTAAAAAATAGATTTGCAAAAAGTGAACAGATTGCTACACACACACACACACACACACACACACAC
ACACACACACAGCCATTCATCTGGGCTGGCAGAGGGGACAGAGTTCAGGGAGGGGCTGAGTCTGGCTAG
GGGCCGAGTCCAGGAGCCCCAGCCAGCCCTTCCCAGGCCAGCGAGGCGAGGCTGCCTCTGGGTGAGTGG
CTGACAGAGCAGGTCTGCAGGCCACCAGCTGCTGGATGTCACCAAGAAGGGGCTCGAGTGCCCCTGCAG
GGGAGGGTCCAATCTCCGGTGTGAGCCCACCTCGTCCCGTTCTCCATTCTGCTTTCTTGCCACACAGTGGG
CCGGCCCCAGGCTCCCCTGGTCTCCTCCCCGTAGCCACTCTCTGCCCACTACCTATGCTTCTAGAAAGCCC
CTCACCTCAGGACCCCAGAGGGACCAGCTGGGGGGCAGGGGGGAGAGGGGGTAATGGAGGCCAAGCCT
GCAGCTTTCTGGAAATTCTTCCCTGGGGGTCCCAGGATCCCCTGCTACTCCACTGACCTGGAAGAGCTGG
GTACCAGGCCACCCACTGTGGGGCAAGCCTGAGTGGTGAGGGGCCACTGGGCCCCATTCTCCCTCCATGG
CAGGAAGGCGGGGGATTTCAAGTTTAGGGATTGGGTCGTGGTGGAGAATCTGAGGGCACTCTCTGCCAG
CTCCACAGGGTGGGATGAGCCTCTCCTTGCCCCAGTCCTGGTTCAGTGGGAATGCAGTGGGTGGGGCTGT
ACACACCCTCCAGCACAGACTGTTCCCTCCAAGGTCCTCTTAGGTCCCGGGAGGAACGTGGTTCAGAGAC
TGGCAGCCAGGGAGCCCGGGGCAGAGCTCAGAGGAGTCTGGGAAGGGGCGTGTCCCTCCTCTTCCTGTA
GTGCCCCTCCCATGGCCCAGCAGCTTGGCTGAGCCCCCTCTCCTGAAGCAGTGTCGCCGTCCCTCTGCCTT
GCACAAAAAGCACAAGCATTCCTTAGCAGCTCAGGCGCAGCCCTAGTGGGAGCCCAGCACACTGCTTCT
CGGAGGCCAGGCCCTCCTGCTGGCTGAGGCTTGGGCCCAGTAGCCCCAATATGGTGGCCCTGGGGAAGA
GGCCTTGGGGGTCTGCTCTGTGCCTGGGATCAGTGGGGCCCCAAAGCCCAGCCCGGCTGACCAACATTCA
AAAGCACAAACCCTGGGGACTCTGCTTGGCTGTCCCCTCCATCTGGGGATGGAGAATGCCAGCCCAAAG
CTGGAGCCAATGGTGAGGGCTGAGAGGGCTGTGGCTGGGTGGTCAGCAGAAACCCCCAGGAGGAGAGA
GATGCTGCTCCCGCCTGATTGGGGCCTCACCCAGAAGGAACCCGGTCCCAGGCCGCATGGCCCCTCCAGG
AACATTCCCACATAATACATTCCATCACAGCCAGCCCAGCTCCACTCAGGGCTGGCCCGGGGAGTCCCCG
TGTGCCCCAAGAGGCTAGCCCCAGGGTGAGCAGGGCCCTCAGAGGAAAGGCAGTATGGCGGAGGCCATG
GGGGCCCCTCGGCATTCACACACAGCCTGGCCTCCCCTGCGGAGCTGCATGGACGCCTGGCTCCAGGCTC
CAGGCTGACTGGGGGCCTCTGCCTCCAGGAGGGCATCAGCTTTCCCTGGCTCAGGGATCTTCTCCCTCCC
CTCACCCGCTGCCCAGCCCTCCCAGCTGGTGTCACTCTGCCTCTAAGGCCAAGGCCTCAGGAGAGCATCA
CCACCACACCCCTGCCGGCCTTGGCCTTGGGGCCAGACTGGCTGCACAGCCCAACCAGGAGGGGTCTGC
CTCCCACGCTGGGACACAGACCGGCCGCATGTCTGCATGGCAGAAGCGTCTCCCTTGGCCACGGCCTGGG
AGGGTGGTTCCTGTTCTCAGCATCCACTAATATTCAGTCCTGTATATTTTAATAAAATAAACTTGACAAAG
GAAAAAAAAAAAAAAAAA
```
P193 PROTEIN (PARTIAL)
ERFFEKMDRNQDGVVTIEEFLEACQKDENIMSSMQLFENVI

Fig. 20 exon1 SEQUENCE (WITH INTRONS INCLUDED):
CGGGAGGAGAGAGGCAGCTCGGCTCGGCTCCGCGCTCAGCTCCGCTCTGCCTCCGGCTCTGCGCTCACCTGCTGCCT
AGTGTTCCCTCTCCTGCTCCAGGACCTCCGGGTAGACCTCAGACCCCGGGCCCATTCCCAGACTCAGCCTCAGCCCG
GACTTCCCCAGCCCCGACAGCACAGTAGGCCGCCAGGGGGCGCCGTGTGAGCGCCCTATCCCGGCCACCCGGCGCCC
CCTCCCACGGCCCGGGCGGGAGCGGGGCGCCGGGGGCCATGCGGGGCCAGGGCCGCAAGGAGAGTTTGTCCGATTCC
CGAGACCTGGACGGCTCCTACGACCAGCTCACGGGTGAGTCAGTGACGTGGGGGTCGCGGGAGGGAGGGTGGATTCC
ATTCCTCCAGACCCTTCCGCCTCTCCGACCCCGGCCTGGCCCGCACCAACACTCTGCCCCATTCCCAGGCACTCTTA
TGGCCGGTCTGGGCGGCAGGACACTGGGGGTTCAAAGCCTTGGGTCCCGCAGGGGTTGGGGAGGAACAGAAGAGGCA
GGTGTGGAGAGGCAGCAGGTGTGGGCGTATGTGACACAGGGCTGAGAGGGTGTCTGGAGTGGGAGGTGTTACCGTGC
GTGAGCACCTGTCATTCTGTGTGTGTGTGTGTGTGTGCGCGCGCACCTCCCACAGCTGGTTGCCATGTGCCCTGGGC
TTGGTGACAGCTAGGGTGAGTGTGATTGTATGTGGCAGTGCAATTGTATGGTCTCGTCAGATGTTTGAGTTTGCGTA
GGACCCTGGTTGTACTGATGAAGTTGTTTTGACCATGTGTCTYTATGTGCAACGATGTGTTGTGAGTGTGTAATTCT
GTATGAAAGTGGTGTGTAACTACCAGAATGTGTCAGGGCTCTACTTTAGGGTGGCTTGTCTCTTTG

Fig. 22A exon 2-11 SEQUENCE (WITH INTRONS INCLUDED):
AGCCNANTGGGTCNCCATGTGTATGCATCCTGTTTACTTAGGTCACATTTGTATATGTTGTGTAAGGAGTACCAGGT
CAATGTGTGTGTGTGTGTGAGCATGNATAAACGCCANCAGGTGTGAGTTANTGAATATCAAGCTGTCACTGGCACCC
ATCACTGTGATGTATTGTTCATACATGTCACNAACACGGCCTGTCACTGTAGGTGTGTGTATRAGAGAGGTGTTCTT
ACCCAGGCAATCCTTGGGTTGGACATCATCNTGAGAGGTCCAGCCATGGCACTTGAGCCAAGGGTACTAGGTCAGCA
AAGACATTGAGGCCACTGCCACCTCATCCTTGCCGCCTCGCTGTCACCGGCCACGTCCCATTAAACCAAGTGCNTGA
GCCTCACCTCTATGGACTCACTGGGCTCCCCTAACCCGATTCCAACCACCCTTGCCATTCCTTTCCTCCCCTTAATT
CCTCCCCCAGCCCGGTCCCCAGATGGGGTTGATTTGTGACTGGCGGGGAGGGGACAGGGAACAGAGGGACCCCGGGA
GTTAATGTGCCTTCCTGGGGTCTTTCTCTCTTCNCAGGCCACCCTCCAGGGCCCACTAAAAAAGCGCTGAAGCAGCGA
TTCCTCAAGCTGCTGCCGAGCTGCGGGCCCCAAGCCCTGCCCTCAGTCAGTGAAAGCAAGTGCCTCTCATGTGCTTC
CCGGGGCGGGGCTCGATGTGTGCGTGCGTGTCTGTGCATGANTGTGTGCGCGTGTGCCCCAGGCCTGCRAGTGTRCS
CATGYTCCAGGCTTGCATGTGTGGGGGGGCGTGCCCCAAGCCTKSGTGTTTGGGGGTGGGGCCTGCCCCAVGCCTGT
GCGTGTGTATGTGTGTGCATGTGCGCRCGAGCGTRCCCCAGACCGGCGTGTGTGTGTGGGGGCGTGCCCTACCCC
TGCATGTGTGTGGAGGGCGTGCCCCAKGCCCKCGGCGNGTTGTTTGTTGTGTATGGGAAGGCGTACCGCACGCCTGC
GTGTGGGGGAGGGCGTGCCCCAGAGCCTGCGTGCGTGTGTGTGTGTGTGTGTGTGTGTGGGCGTGACCAGCG
TGGCGAGGGCGGGTGCTGGCAAGGCTGGAGCATAAGNGGGCGNGGCTACATGTGTGNGTGTACGNCTGAAGCCAGCG
TGTGTGGGCGTGGTCAGTTGGNAGCGGGTGTGTGTCACCGCTCCCGCAAAACTGTGGGACCCGAGAGTGTGGGTGTG
ACCATTGTGACCAGGNTGAGGCCTGAGCCTGTGTAGCTGTGGCGGCCTGTGTAGACCAGGCGGCCGTGAGGGTCTGT
ATGTGGCTTAGCTGGGTTAGTGTCTTCAACTCCGTGCGGCCGCCCCCTTCCCCACCGTGTTTTGGACCCCTGATGTG
TGTTGCCTATGCCCCGACAGGATGGTGACAGGTGTAGAGGATGGCGCCTGCCCTCCTCCAGACGCCAGGGTATTTGG
GTTTTCTGTGCCAGCCTGGTCCCCTGCTGAAGTGATCTCCAGTTGAGTGACCTCGCTTTGTCTCTAGGTCTCCATTT
CCTCAGTTGGGCCTTGCCCACCTCATAGGATCATACTGCATTTTGCAAACCATAAAGGCCCGCTTTGTAGTTATTTG
AGCATGCTGTTGTGTTGGACTTAGATGGGTCCCACACGGGGGTGGATTCGGARAAGGACAGGCGTGAGTCCCGCAAG
CTTGTGTGCATGGGGTCCGTTTCGTGTGTGTCTGTGCTGGTTGGGTGTGCCTTTGCACGGGCTGGGTTGTCAGGTTT
GCTCTGAGTGTGAGGGGCCAGGTGTGTGTATGCAGTTGGCCGGGTCTTCCGCTTTCTCGGTGWCAGTTCGCTCCCTT
CAGCATTAGCCGCCCCAGCCTCCCTCCGCCCCACAGACCCCGCCTGCTGGACCCAGGTGACTTACGCTCCTGGTGG
GGGCGGGGCGGGGCAGGGCGGCTTTGCCATCTTGGGGTGGGGGCACTTGCCTGGGGGCTGGACGTTGGGGCGGGG
CAGGATTGAGATGGGGCCGGGGGTGGGGTCTGGATGGAGGTTGGCTGAGCTGGGCGGGGCATGGCTCAGGCATGGCT
GGGATAGATGGGGCTGGGCGGGGCGAGGGGAGGGGCTGGGTGGGACGAGGGGAGGGTTTGGGCGGGGCAAGGCTGGG
GCTGGGCGGATCTGAGTTGGTCCCCGAAGGCCCGGAGCTCTGACCCTCAGACGCCCCTCTTGAACTGGCTTTTCCC
ACTCCTCCCTTTCTAAAACGAAGATGCGGCTGGGGGCCTTCCCCTCCAACGAGGGATCGAGGGCCGCGGGGCGAGCA
CTGAGTCGGATCCCTGGCTCTGGGGCCAGGCCAGGCCTTGGCCCGCTGATAGACCTCGAAGATGGCCATCATCTTTT
CTCCTTACCTCAGTGTCCTTGGCTCGGGGCCCAGGGAACTGGCAGCCTGGTCTCCGGCATCGGATGGGACCGGGGGG
CGGGGAGGGGGTGAATGGGCAGTGATTTGAAGAGGGGTCGCGGAGGCTGGGCATGAGGCGCGGCTGTCCTCACCGC
TCCCGCAGACAGCGTGGACGATGAATTTGAATTGTCCACCGTGTGTCACCGGCCTGAGGGTCTGGAGCAGCTGCAGG
AGCAAACCAAATTCACGCGCAAGGAGTTGCAGGTCCTGTACCGGGGCTTCAAGAACGTGAGTGCNGGGCGAGGCCAA

Fig. 22B

```
ACTCAGCGNGGGTGGGACAGGAGGACCCAANCCGGTCCANATTTTTCCCANAAAGCATGGCTTNGATGCTTGAGGNG
CGGGCGGAAGGGAGGCAAGGCCCTGAGACTGAACTTCTAGCTGGAGGTTCTGGGGCGGGGCCAGAACGRAAGTGGCG
CCTGTAGACTGTCAGTTTCGTTCCATGTTTTTTATTTGTGCACTGGGAAAGAAGTCTTCCCTCCCATCACATGAGCC
ACGTGGTGAGTCCTCTGGAGGCTTGAAGATTATCCCCCTCCCTGGGAGTCTTGGGCCATGGAGGGTGGGGGCGGTGA
ACGGAAGGGGATTTTGTCTCTGCCCTCAGCCTGGTGCCCTCTCCTTCCAGGAATGTCCCAGCGGAATTGTCAATGAG
GAGAACTTCAAGCAGATTTACTCCCAGTTCTTTCCTCAAGGAGGTGAGGGGACAAGGCCCAAGGGGAAGCAGTTGTC
CTTCTCTAGGCTGAGGGAGGGAGGGATTCTGGAGGAGCTGGGAATGCCAAGGTGATGGGGGGTATGGGGAGCTCCTT
AGAGGGAGGAAGTCCTCTCCTGTGTGGAAGCCAACTTCTCCACACTCACCCTGCAGACTCCAGCACCTATGCCACTT
TTCTCTTCAATGCCTTTGACACCAACCATGATGGCTCGGTCAGTTTTGAGGTGAGCTGGGCGAGGTGGGCCAGGGAA
GCCTGTTTCCTGGAGTTCAGGGCCAGGATCTCCAGGCCAAACCCAGAGAAGGAGTTGGGTGAAGAGKACCCGAGGAC
ACAGCTCCCTNCTGCCTTCTTCCCAGGACTTTGTGGCTGGTTTGYCCGTGATTCTTCGGGGAACTGTAGATGACAGG
CTTAATTGGGCCTTCAACCTGTATGACCTTAACAAGGACGGCTGCATCACCAAGGAGGTGCAGGGCAACTGAAGGGC
TGGGGGTCTGTGGCGGTGATGGGGGTGGCGTGCAKAGGGTGATGGGAGGGAAATATGACCCACATATGCCCACAAGC
AATGGGATCAAGGGAGGCTGGAGGCTCTGAGGAAGGATCCTCTTCTCTCTTGGCCTAACAGGAAATGCTTGACATCA
TGAAGTCCATCTATGACATGATGGGCAAGTACACGTACCCTGCACTCCGGGAGGAGGCCCCAAGGGAACACGTGGAG
AGCTTCTTCCAGGTACTTGGGAGTGGGTATGGCTGGAGGGCCCTGGAGTGAAGGGAAGAAGGCCAAGAACCAGCAGG
GAACTCACCTGACTTCTGTCTGCCTCTCTCTTGCCATCCCTCCTGTTCTCCCTGCCTGACCACCTTCTTGCAGAAGA
TGGACAGAAACAAGGATGGTGTGGTGACCATTGAGGAATTCATTGAGTCTTGTCAAAAGGTACAGCTCCCTGCCCTC
TACATTACCCTGACCTGGACTCAGGCCTGATTTAGTAATGCAGGGAAAAGCTTCTTTGGGAAGAATACCACCTTCCC
ACCTCACCCCCATATTTCAATCCTATTCCTTTGTGGGAGGCTTACCCCTTCCCTACCTCAGGTCTCTCTGGGCATCT
CCTTCCTCTGTGCTTTTGAATGTCCCCGTCTGTGACTCAAGTGTCCCTCTCACTGTCTCTGATAAAGCTCCTTCTCT
TTCTCTCTCTTCAATCTGCCTCGCTCACATCATGGCCACAGGATGAGAACATCATGAGGTCCATGCAGCTCTTTGAC
AATGTCATCTAGCCCCCAGGAGAGGGGGTCAGTGTTTCCTGGGGGGACCATGCTCTAACCCTAGTCCAGGCGGACCT
CACCCTTCTCTTCCCAGGTCTATCCTCATCCTACGCCTCCCTGGGGGCTGGAGGGATCCAAGAGCTTGGGGATTCAG
TAGTCCAGATCTCTGGAGCTGAAGGGGCCAGAGAGTGGGCAGAGTGCATCTCGGGGGGTGTTCCCAACTCCCACCAG
CTCTCACCCCCTTCCTGCCTGACACCCAGTGTTGAGAGTGCCCCTCCTGTAGGAATTGAGCGGTTCCCCACCTCCTA
CCCCTACTCTAGAAACACACTAGACAGATGTCTCCTGGCTATGGTGCTTCCCCCATCCCTGACCTCATAAACATTTCC
CCTAAGACTCCCCTCTCAGAGAGAATGCTCCATTCTTGGCACTGGCTGGCTTCTCAGACCAGCCATTGAGAGCCCTG
TGGGAGGGGGACAAGAATGTATAGGGAGAAATCTTGGGCCTGAGTCAATGGATAGGTCCTAGRAGGTGGCTGGGGTT
GAGAATAGAAGGGCCTGGACAGATTATGATTGCTCAGGCATACCAGGTTATAGCTCCAAGTTCCACAGGTCTGCTAC
CACAGGCCATCAAAATATAAGTTTCCAGGCTTTGCAGAAGACCTTGTCTCCTTAGAAATGCCCCAGAAATTTTCCAC
ACCCTCCTCGGTATCCATGGAGAGCCTGGGGCCAGATATCTGGCTCATCTCTGGCATTGCTTCCTCTCCTTCTTTCC
TGCATGTGTTGGTGGTGGTTGTGGTGGGGGAATGTGGATGGGGATGTCCTGGCTGATGCCTGCCAAAATTTCATCC
CACCCTCCTTGCTTATCGTCCCTGTTTTGAGGGCTATGACTTGAGTTTTTGTTTCCCATGTTCTCTATAGACTTGGG
ACCTTCCTGAACTTGGGGCCTATCACTCCCCACAGTGGATGCCTTAGAAGGGAGAGGGAAGGAGGGAGGCAGGCATA
GCATCTGAACCCAGTGTGGGGGCATTCACTAGAATCTTCAATCAACCTGGGCTCTCCCCACCCCACCCCAGATAACC
TCCTCAGKTCCCTAGGGTCTCTTCTYGCTTGACTCAATCTACCCAGAGATGCCCCTTAGCACACCTAGAGGGCAGGG
ACCATAGGACCCAGGTTCCAACCCCATTGTCAGCACCCCAGCCATGCGGCCACCCCTTAGCACACCTGCTCGTCCCA
TTTAGCTTACCCTCCCAGTTGGCCAGAATCTGAGGGGAGAGCCCCCAGAGAGCCCCCTTCCCCATCAGAAGACTGTT
GACTGCTTTGCATTTTGGGCTCTTCTATATATTTTGTAAAGTAAGAAATATACCAGATC:TAATAAAACACAATGGC
TATGCACAGGCTGCCGTCTCTGCCTTTTGTCCCTCCCACCTACAAATACTACACAACCCCTAACGAATGCACCTGCA
GCCTTTTAGATCCCCAAGAAAGTGGCTTTCTTTTCCATAGTTGGCCATACCTTGGCATGAGACTGAGACACAGGCTC
TGGAATGGTTGGAAACCCACCCAACCTCAGGCCCCCACATGAATCTCCCTCCCACACAGCCTGAGAGGAGACAAGGA
AGGAAGGACAGGACACTGATGTCCCGAAGACTGTGCCAAGCAAGCTGTTTTTTAGCTGACATTCTTACAAGTTGAAT
CACAGATTTCTAATTTACAGAGTTTTTAGTTAATCTCAAAGTGCTTTCTTTTGAGGGGCCTCCTTTAAGTTCYTTCT
TTTTTTTTTTTTTT
```

FIGURE 22 B (cont'd)

POTASSIUM CHANNEL INTERACTING POLYPEPTIDES AND USES THEREOF

RELATED APPLICATIONS

This application is a continuation of 09/298,731 Apr. 23, 1999, now U.S. Pat. No. 6,369,197, which claims benefit of 60/110,033 filed Nov. 25, 1998, and claims benefit of 60/109,333 filed Nov. 20, 1998, and claims benefit of 60/110,277 filed Nov. 30, 1998.

TECHNICAL FIELD

The present invention relates to novel polynucleotides and proteins encoded by such polynucleotides, along with therapeutic, diagnostic, and research utilities for these polynucleotides and proteins. Specifically, the present invention provides novel polypeptide interactors of potassium channel proteins which form the basis of drug discovery and design, therapeutic treatment, and diagnostic methods.

BACKGROUND OF THE INVENTION

Mammalian cell membranes are important to the structural integrity and activity of many cells and tissues. Of particular interest in membrane physiology is the study of trans-membrane ion channels which act to directly control a variety of pharmacological, physiological, and cellular processes. Numerous ion channels have been identified including calcium, sodium, and potassium channels, each of which have been investigated to determine their roles in vertebrate and insect cells.

Because of their involvement in maintaining normal cellular homeostasis, much attention has been given to potassium channels. A number of these potassium channels open in response to changes in the cell membrane potential. Many voltage-gated potassium channels have been identified and characterized by their electrophysiological and pharmacological properties. Potassium currents are more diverse than sodium or calcium currents and are further involved in determining the response of a cell to external stimuli.

The diversity of potassium channels and their important physiological role highlights their potential as targets for developing therapeutic agents for various diseases. One of the best characterized classes of potassium channels are the voltage-gated potassium channels. The prototypical member of this class is the protein encoded by the Shaker gene in *Drosophila melanogaster*. Proteins of the Shal or Kv4 family are a type of voltage-gated potassium channels that underlies many of the native A type currents that have been recorded from different primary cells. Kv4 channels have a major role in the repolarization of cardiac action potentials. In neurons, Kv4 channels and the A currents they may comprise play an important role in modulation of firing rate, action potential initiation and in controlling dendritic responses to synaptic inputs.

The fundamental function of a neuron is to receive, conduct, and transmit signals. Despite the varied purpose of the signals carried by different classes of neurons, the form of the signal is always the same and consists of changes in the electrical potential across the plasma membrane of the neuron. The plasma membrane of a neuron contains voltage-gated cation channels, which are responsible for propagating this electrical potential (also referred to as an action potential or nerve impulse) across and along the plasma membrane.

The Kv family of channels includes, among others: (1) the delayed-rectifier potassium channels, which repolarize the membrane after each action potential to prepare the cell to fire again; and (2) the rapidly inactivating (A-type) potassium channels, which are active predominantly at subthreshold voltages and and act to reduce the rate at which excitable cells reach firing threshold. In addition to being critical for action potential conduction, Kv channels also control the response to depolarizing, e.g., synaptic, inputs and play a role in neurotransmitter release. As a result of these activities, voltage-gated potassium channels are key regulators of neuronal excitability (Hille B., Ionic Channels of Excitable Membranes, Second Edition, Sunderland, Mass.: Sinauer, (1992)).

There is tremendous structural and functional diversity within the Kv potassium channel superfamily. This diversity is generated both by the existence of multiple genes and by alternative splicing of RNA transcripts produced from the same gene. Nonetheless, the amino acid sequences of the known Kv potassium channels show high similarity. All appear to be comprised of four, pore forming β-subunits and some are known to have four cytoplasmic (β-subunit polypeptides (Jan L. Y. et al. (1990) *Trends Neurosci* 13:415–419, and Pongs, O. et al. (1995) *Sem Neurosci.* 7:137–146). The known Kv channel (—subunits fall into four sub-families named for their homology to channels first isolated from *Drosophila*: the Kv1, or Shaker-related subfamily; the Kv2, or Shab-related subfamily; the Kv3, or Shaw-related subfamily; and the Kv4, or Shal-related subfamily. Kv4.2 and Kv4.3 are examples of Kv channel (β-subunits of the Shal-related subfamily. Kv4.3 has a unique neuroanatomical distribution in that its mRNA is highly expressed in brainstem monoaminergic and forebrain cholinergic neurons, where it is involved in the release of the neurotransmitters dopamine, norepinephrine, serotonin, and acetylcholine.

This channel is also highly expressed in cortical pyramidal cells and in interneurons. (Serdio P. et al. (1996) *J. Neurophys* 75:2174–2179). Interestingly, the Kv4.3 polypeptide is highly expressed in neurons which express the corresponding mRNA. The Kv4.3 polypeptide is expressed in the somatodendritic membranes of these cells, where it is thought to contribute to the rapidly inactivating K+ conductance. Kv4.2 mRNA is widely expressed in brain, and the corresponding polypeptide also appears to be concentrated in somatodendritic membranes where it also contributes to the rapidly inactivating $K^+$ conductance (Sheng et al. (1992) Neuron 9:271–84). These somatodendritic A-type Kv channels, like Kv4.2 and Kv4.3 are likely involved in processes which underlie learning and memory, such as integration of sub-threshold synaptic responses and the conductance of back-propagating action potentials (Hoffman D. A. et al. (1997) *Nature* 387:869–875).

Thus, proteins which interact with and modulate the activity of potassium channel proteins e.g., potassium channels having a Kv4.2 or Kv4.3 subunit, provide novel molecular targets to modulate neuronal excitability, e.g., action potential conduction, somatodendritic excitability and neurotransmitter release, in cells expressing these channels. In addition, detection of genetic lesions in the gene encoding these proteins could be used to diagnose and treat central nervous system disorders such as epilepsy, anxiety, depression, age-related memory loss, migraine, obesity, Parkinsons disease or Alzheimer's disease.

SUMMARY OF THE INVENTION

The present invention is based, at least in part, on the discovery of four novel sets (1v, 9q, p19, and W28559) of nucleic acid molecules which encode gene products that interact with potassium channel proteins or possess substantial homology to the gene products of the invention that interact with potassium channel proteins (paralogs). Potassium channel proteins are, for example, potassium channels having a Kv4.2 or Kv4.3 subunit. The nucleic acid molecules of the invention and their gene products are referred to herein as "Potassium Channel Interacting Proteins" or "PCIP" nucleic acid and protein molecules. Preferably, the PCIP proteins of the present invention interact with, e.g., bind to a potassium channel protein, modulate the activity of a potassium channel protein, and/or modulate a potassium channel mediated activity in a cell, e.g., a neuronal cell. The PCIP molecules of the present invention are useful as modulating agents to regulate a variety of cellular processes, e.g., neuronal cell processes. Accordingly, in one aspect, this invention provides isolated nucleic acid molecules encoding PCIP proteins or biologically active portions thereof, as well as nucleic acid fragments suitable as primers or hybridization probes for the detection of PCIP-encoding nucleic acids.

In one embodiment, a PCIP nucleic acid molecule of the invention is at least 50%, 55%, 60%, 65%, 70%, 75%, 80%, 85%, 90%, 95% or more identical to the nucleotide sequence (e.g., to the entire length of the nucleotide sequence) shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a complement thereof.

In another preferred embodiment, the isolated nucleic acid molecule includes the nucleotide sequence shown SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or a complement thereof. In another preferred embodiment, the nucleic acid molecule includes a fragment of at least 300, 350, 400, 426, 471, or 583 nucleotides of the nucleotide sequence of SEQ ID NO:1, SEQ ID NO:3 SEQ ID NO:5, SEQ ID NO:7, SEQ ID NO:9, SEQ ID NO:11, SEQ ID NO: 13, SEQ ID NO: 15, SEQ ID NO: 17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or a complement thereof.

In another embodiment, a PCIP nucleic acid molecule includes a nucleotide sequence encoding a protein having an amino acid sequence sufficiently identical to the amino acid sequence of SEQ ID NO: 2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40, or an amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In a preferred embodiment, a PCIP nucleic acid molecule includes a nucleotide sequence encoding a protein having an amino acid sequence at least 50%, 55%, 60%, 65%, 70%, 75%, 80%, 85%, 90%, 95% or more identical to the amino acid sequence of SEQ ID NO: 2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40, or the amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994.

In another preferred embodiment, an isolated nucleic acid molecule encodes the amino acid sequence of 1v, 9q, p19, or W28559 protein. In yet another preferred embodiment, the nucleic acid molecule includes a nucleotide sequence encoding a protein having the amino acid sequence of SEQ ID NO: 2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40, or the amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In yet another preferred embodiment, the nucleic acid molecule is at least 426, 471, or 583 nucleotides in length and encodes a protein having a PCIP activity (as described herein).

Another embodiment of the invention features nucleic acid molecules, preferably PCIP nucleic acid molecules, which specifically detect PCIP nucleic acid molecules relative to nucleic acid molecules encoding non-PCIP proteins. For example, in one embodiment, such a nucleic acid molecule is at least 426, 400–450, 471, 450–500, 500–550, 583, 550–600, 600–650, 650–700, 700–750, 750–800 or more nucleotides in length and hybridizes under stringent conditions to a nucleic acid molecule comprising the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a complement thereof. In preferred embodiments, the nucleic acid molecules are at least 15 (e.g., contiguous) nucleotides in length and hybridize under stringent conditions to nucleotides 93–126, 360–462, 732–825, 1028–1054, or 1517–1534 of SEQ ID NO:7. In other preferred embodiments, the nucleic acid molecules comprise nucleotides 93–126, 360–462, 732–825, 1028–1054, or 1517–1534 of SEQ ID NO:7.

In other preferred embodiments, the nucleic acid molecules are at least 15 (e.g., contiguous) nucleotides in length and hybridize under stringent conditions to nucleotides 1–14, 49–116, 137–311, 345–410,430–482, 503–518,662–693, 1406–1421, 1441–1457, 1478–1494, or 1882–1959 of SEQ ID NO:13. In other preferred embodiments, the nucleic acid molecules comprise nucleotides 1–14, 49–116, 137–311, 345–410, 430–482, 503–518, 662–693, 1406–1421, 1441–1457, 1478–1494, or 1882–1959 of SEQ ID NO:13.

In preferred embodiments, the nucleic acid molecules are at least 15 (e.g., contiguous) nucleotides in length and hybridize under stringent conditions to nucleotides 932–1527, 1548–1765, 1786–1871, 1908–2091, 2259–2265, or 2630–2654 of SEQ ID NO:35. In other preferred embodiments, the nucleic acid molecules comprise nucleotides 932–1527, 1548–1765, 1786–1871, 1908–2091, 2259–2265, or 2630–2654 of SEQ ID NO:35.

In other preferred embodiments, the nucleic acid molecule encodes a naturally occurring allelic variant of a polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40 or an amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, wherein the nucleic acid molecule hybridizes to a nucleic acid molecule comprising SEQ ID NO:1, SEQ ID NO:3 SEQ ID NO:5, SEQ ID NO:7, SEQ ID NO:9, SEQ ID NO:11, SEQ ID NO: 13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47 under stringent conditions.

Another embodiment of the invention provides an isolated nucleic acid molecule which is antisense to a PCIP nucleic acid molecule, e.g., the coding strand of a PCIP nucleic acid molecule.

Another aspect of the invention provides a vector comprising a PCIP nucleic acid molecule. In certain embodiments, the vector is a recombinant expression vector. In another embodiment, the invention provides a host cell containing a vector of the invention. The invention also provides a method for producing a protein, preferably a PCIP protein, by culturing in a suitable medium, a host cell, e.g., a mammalian host cell such as a non-human mammalian cell, of the invention containing a recombinant expression vector, such that the protein is produced.

Another aspect of this invention features isolated or recombinant PCIP proteins and polypeptides. In one embodiment, the isolated protein, preferably a PCIP protein, includes at least one calcium binding domain. In a preferred embodiment, the protein, preferably a PCIP protein, includes at least one calcium binding domain and has an amino acid sequence at least about 50%, 55%, 60%, 65%, 70%, 75%, 80%, 85%, 90%, 95% or more identical to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40, or the amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In another preferred embodiment, the protein, preferably a PCIP protein, includes at least one calcium binding domain and modulates a potassium channel mediated activity. In yet another preferred embodiment, the protein, preferably a PCIP protein, includes at least one calcium binding domain and is encoded by a nucleic acid molecule having a nucleotide sequence which hybridizes under stringent hybridization conditions to a nucleic acid molecule comprising the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47.

In another embodiment, the invention features fragments of the proteins having the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40, wherein the fragment comprises at least 15 amino acids (e.g., contiguous amino acids) of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40, or an amino acid sequence encoded by the DNA insert of the plasmid deposited with the ATCC as Accession Number 98936, 98937, 98938, 98939, 98940, 98941, 98942, 98943, 98944, 98945, 98946, 98947, 98948, 98949, 98950, 98951, 98991, 98993, or 98994. In another embodiment, the protein, preferably a PCIP protein, has the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40.

In another embodiment, the invention features an isolated protein, preferably a PCIP protein, which is encoded by a nucleic acid molecule having a nucleotide sequence at least about 50%, 55%, 60%, 65%, 70%, 75%, 80%, 85%, 90%, 95% or more identical to a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or a complement thereof.

The proteins of the present invention or biologically active portions thereof, can be operatively linked to a non-PCIP polypeptide (e.g., heterologous amino acid sequences) to form fusion proteins. The invention further features antibodies, such as monoclonal or polyclonal antibodies, that specifically bind proteins of the invention, preferably PCIP proteins. In addition, the PCIP proteins or biologically active portions thereof can be incorporated into pharmaceutical compositions, which optionally include pharmaceutically acceptable carriers.

In another aspect, the present invention provides a method for detecting the presence of a PCIP nucleic acid molecule, protein or polypeptide in a biological sample by contacting the biological sample with an agent capable of detecting a PCIP nucleic acid molecule, protein or polypeptide such that the presence of a PCIP nucleic acid molecule, protein or polypeptide is detected in the biological sample.

In another aspect, the present invention provides a method for detecting the presence of PCIP activity in a biological sample by contacting the biological sample with an agent capable of detecting an indicator of PCIP activity such that the presence of PCIP activity is detected in the biological sample.

In another aspect, the invention provides a method for modulating PCIP activity comprising contacting a cell capable of expressing PCIP with an agent that modulates PCIP activity such that PCIP activity in the cell is modulated. In one embodiment, the agent inhibits PCIP activity. In another embodiment, the agent stimulates PCIP activity. In one embodiment, the agent is an antibody that specifically binds to a PCIP protein. In another embodiment, the agent modulates expression of PCIP by modulating transcription of a PCIP gene or translation of a PCIP mRNA. In yet another embodiment, the agent is a nucleic acid molecule having a nucleotide sequence that is antisense to the coding strand of a PCIP mRNA or a PCIP gene.

In one embodiment, the methods of the present invention are used to treat a subject having a disorder characterized by aberrant PCIP protein or nucleic acid expression or activity by administering an agent which is a PCIP modulator to the subject. In one embodiment, the PCIP modulator is a PCIP protein. In another embodiment the PCIP modulator is a PCIP nucleic acid molecule. In yet another embodiment, the PCIP modulator is a peptide, peptidomimetic, or other small molecule. In a preferred embodiment, the disorder characterized by aberrant PCIP protein or nucleic acid expression is a CNS disorder.

The present invention also provides a diagnostic assay for identifying the presence or absence of a genetic alteration characterized by at least one of (i) aberrant modification or mutation of a gene encoding a PCIP protein; (ii) misregulation of the gene; and (iii) aberrant post-translational modification of a PCIP protein, wherein a wild-type form of the gene encodes a protein with a PCIP activity.

In another aspect the invention provides a method for identifying a compound that binds to or modulates the activity of a PCIP protein, by providing an indicator composition comprising a PCIP protein having PCIP activity, contacting the indicator composition with a test compound, and determining the effect of the test compound on PCIP activity in the indicator composition to identify a compound that modulates the activity of a PCIP protein.

Other features and advantages of the invention will be apparent from the following detailed description and claims.

BRIEF DESCRIPTION OF THE DRAWINGS

FIG. 1 depicts the cDNA sequence and predicted amino acid sequence of human 1v. The nucleotide sequence corresponds to nucleic acids 1 to 1463 of SEQ ID NO:1. The amino acid sequence corresponds to amino acids 1 to 216 of SEQ ID NO:2.

FIG. 2 depicts the cDNA sequence and predicted amino acid sequence of rat 1v. The nucleotide sequence corresponds to nucleic acids 1 to 1856 of SEQ ID NO:3. The amino acid sequence corresponds to amino acids 1 to 245 of SEQ ID NO:4.

FIG. 3 depicts the cDNA sequence and predicted amino acid sequence of mouse 1v. The nucleotide sequence corresponds to nucleic acids 1 to 1907 of SEQ ID NO:5. The amino acid sequence corresponds to amino acids 1 to 216 of SEQ ID NO:6.

FIG. 4 depicts the cDNA sequence and predicted amino acid sequence of rat 1 vl. The nucleotide sequence corresponds to nucleic acids 1 to 1534 of SEQ ID NO:7. The amino acid sequence corresponds to amino acids 1 to 227 of SEQ ID NO:8.

FIG. 5 depicts the cDNA sequence and predicted amino acid sequence of mouse lyl. The nucleotide sequence corresponds to nucleic acids 1 to 1540 of SEQ ID NO:9. The amino acid sequence corresponds to amino acids 1 to 227 of SEQ ID NO: 10.

FIG. 6 depicts the cDNA sequence and predicted amino acid sequence of rat 1 vn. The nucleotide sequence corresponds to nucleic acids 1 to 955 of SEQ ID NO:11. The amino acid sequence corresponds to amino acids 1 to 203 of SEQ ID NO:12.

FIG. 7 depicts the cDNA sequence and predicted amino acid sequence of human 9ql. The nucleotide sequence corresponds to nucleic acids 1 to 2009 of SEQ ID NO:13. The amino acid sequence corresponds to amino acids 1 to 270 of SEQ ID NO:14.

FIG. 8 depicts the cDNA sequence and predicted amino acid sequence of rat 9ql. The nucleotide sequence corresponds to nucleic acids 1 to 1247 of SEQ ID NO:15. The amino acid sequence corresponds to amino acids 1 to 257 of SEQ ID NO:16.

FIG. 9 depicts the cDNA sequence and predicted amino acid sequence of mouse 9ql. The nucleotide sequence corresponds to nucleic acids 1 to 2343 of SEQ ID NO:17. The amino acid sequence corresponds to amino acids 1 to 270 of SEQ ID NO:18.

FIG. 10 depicts the cDNA sequence and predicted amino acid sequence of human 9qm. The nucleotide sequence corresponds to nucleic acids 1 to 1955 of SEQ ID NO:19. The amino acid sequence corresponds to amino acids 1 to 252 of SEQ ID NO:20.

FIG. 11 depicts the cDNA sequence and predicted amino acid sequence of rat 9qm. The nucleotide sequence corresponds to nucleic acids 1 to 2300 of SEQ ID NO:21. The amino acid sequence corresponds to amino acids 1 to 252 of SEQ ID NO:22.

FIG. 12 depicts the cDNA sequence and predicted amino acid sequence of human 9qs. The nucleotide sequence corresponds to nucleic acids 1 to 1859 of SEQ ID NO:23. The amino acid sequence corresponds to amino acids 1 to 220 of SEQ ID NO:24.

FIG. 13 depicts the cDNA sequence and predicted amino acid sequence of monkey 9qs. The nucleotide sequence corresponds to nucleic acids 1 to 2191 of SEQ ID NO:25. The amino acid sequence corresponds to amino acids 1 to 220 of SEQ ID NO:26.

FIG. 14 depicts the cDNA sequence and predicted amino acid sequence of rat 9qc. The nucleotide sequence corresponds to nucleic acids 1 to 2057 of SEQ ID NO:27. The amino acid sequence corresponds to amino acids 1 to 252 of SEQ ID NO:28.

FIG. 15 depicts the cDNA sequence and predicted amino acid sequence of rat 8t. The nucleotide sequence corresponds to nucleic acids 1 to 1904 of SEQ ID NO:29. The amino acid sequence corresponds to amino acids 1 to 225 of SEQ ID NO:30.

FIG. 16 depicts the cDNA sequence and predicted amino acid sequence of human p19. The nucleotide sequence corresponds to nucleic acids 1 to 619 of SEQ ID NO:31. The amino acid sequence corresponds to amino acids 1 to 200 of SEQ ID NO:32.

FIG. 17 depicts the cDNA sequence and predicted amino acid sequence of rat p19 The nucleotide sequence corresponds to nucleic acids 1 to 442 of SEQ ID NO:33. The amino acid sequence corresponds to amino acids 1 to 109 of SEQ ID NO:34.

FIG. 18 depicts the cDNA sequence and predicted amino acid sequence of mouse p19. The nucleotide sequence corresponds to nucleic acids 1 to 2644 of SEQ ID NO:35. The amino acid sequence corresponds to amino acids 1 to 256 of SEQ ID NO:36.

FIG. 19 depicts the cDNA sequence and predicted amino acid sequence of human W28559. The nucleotide sequence corresponds to nucleic acids 1 to 380 of SEQ ID NO:37. The amino acid sequence corresponds to amino acids 1 to 126 of SEQ ID NO:38.

FIG. 20 depicts the cDNA sequence and predicted amino acid sequence of human P193. The nucleotide sequence corresponds to nucleic acids 1 to 2176 of SEQ ID NO:39. The amino acid sequence corresponds to amino acids 1 to 41 of SEQ ID NO:40.

FIG. 22 depicts the genomic DNA sequence of human 9q. FIG. 22A depicts exon 1 and its flanking intron sequences (SEQ ID NO:46). FIG. 22B depicts exons 2–11 and the flanking intron sequences (SEQ ID NO:47).

DETAILED DESCRIPTION OF THE INVENTION

Figure 21:
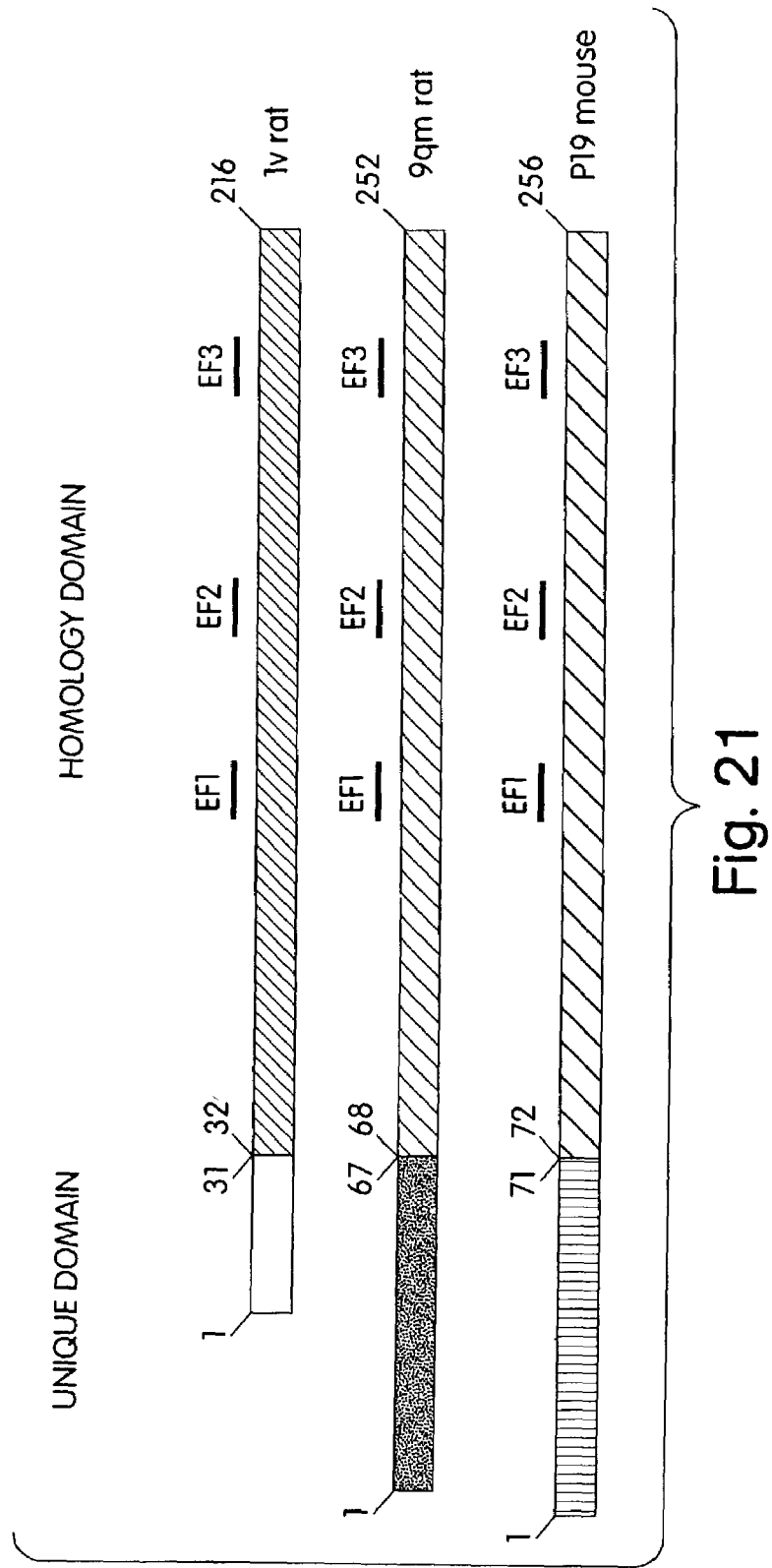
FIG. 21 depicts a schematic representation of the rat 1 v, the rat 9qm, and the mouse P19 proteins, aligned to indicate the conserved domains among these proteins.

| | | |
|---|---|---|
| I. | Isolated Nucleic Acid Molecules | 17 |
| II. | Isolated PCIP Proteins and Anti-PCIP Antibodies | 31 |
| III. | Recombinant Expression Vectors and Host Cells | 40 |
| IV. | Pharmaceutical Compositions | 47 |
| V. | Uses and Methods of the Invention | 51 |
| | A. Screening Assays | 52 |
| | B. Detection Assays | 57 |
| |   1. Chromosome Mapping | 57 |
| |   2. Tissue Typing | 59 |
| |   3. Use of Partial PCIP Sequences in Forensic Biology | 60 |
| | C. Predictive Medicine | 61 |
| |   1. Diagnostic Assays | 61 |
| |   2. Prognostic Assays | 63 |
| |   3. Monitoring of Effects During Clinical Trials | 67 |
| | D. Methods of Treatment | 68 |
| |   1. Prophylactic Methods | 69 |
| |   2. Therapeutic Methods | 69 |
| |   3. Pharmacogenomics | 71 |

The present invention is based, at least in part, on the discovery of four novel sets (1v, 9q, p19, and W28559) of nucleic acid molecules which encode gene products that interact with potassium channel proteins or possess substantial homology to the gene products of the invention that interact with potassium channel proteins (paralogs).

Potassium channel proteins are, for example, potassium channels having a Kv4.2 or Kv4.3 subunit. The nucleic acid molecules of the invention and their gene products are referred to herein as "Potassium Channel Interacting Proteins" or "PCIP" nucleic acid and protein molecules. Preferably, the PCIP proteins of the present invention interact with, e.g., bind to a potassium channel protein, modulate the activity of a potassium channel protein, and/or modulate a potassium channel mediated activity in a cell, e.g., a neuronal cell.

The nucleic acid molecules of the invention that are members of the 1v, 9q, p19, and W28559 sets are listed in Table 1 and described below. For PCIP set 1v, the invention provides full length human, mouse, and rat 1v cDNA clones, full length mouse and rat cDNA clones of 1v splice variant 1vl, a partial rat cDNA clone of 1v splice variant 1vn, and the proteins encoded by these cDNAs. For PCIP set 9q, the invention provides full length human and mouse and partial rat 9ql cDNA clones, full length human and rat cDNA clones of 9ql splice variant 9qm, full length human and monkey cDNA clones of 9ql splice variant 9qs, a full length rat cDNA clone of 9ql splice variant 9qc, a partial rat cDNA clone of 9ql splice variant 8t, and the proteins encoded by these cDNAs. For PCIP set p19, the invention provides full length mouse and partial rat and human p19 cDNA clones and the proteins encoded by these cDNAs. Two partial human cDNA clones of p19 are provided, p195 and p193, representing, respectively, the 5' and 3' ends of the human p19 cDNA. For PCIP set W28559, the invention provides a partial human W28559 cDNA clone and the protein encoded by this cDNA.

As used herein, a "potassium channel" includes a protein or polypeptide that is involved in receiving, conducting, and transmitting signals in an excitable cell. Potassium channels are typically expressed in electrically excitable cells, e.g., neurons, cardiac, skeletal and smooth muscle, renal, endocrine, and egg cells, and can form heteromultimeric structures, e.g., composed of pore-forming and cytoplasmic subunits. Examples of potassium channels include: (1) the voltage-gated potassium channels, (2) the ligand-gated potassium channels, and (3) the mechanically-gated potassium channels. For a detailed description of potassium channels, see Kandel E. R. et al., Principles of Neural Science, second edition, (Elsevier Science Publishing Co., Inc., N.Y. (1985)), the contents of which are incorporated herein by reference. The PCIP proteins of the present invention have been shown to interact with, for example, potassium channels having a Kv4.3 subunit or a Kv4.2 subunit.

As used herein, a "potassium channel mediated activity" includes an activity which involves a potassium channel, e.g., a potassium channel in a neuronal cell or a muscle cell, associated with receiving, conducting, and transmitting signals in, for example, the nervous system. Potassium channel mediated activities include release of neurotransmitters, e.g., dopamine or norepinephrine, from cells, e.g., neuronal cells; modulation of resting potential of membranes, wave forms and frequencies of action potentials, and thresholds of excitation; and modulation of processes such as integration of sub-threshold synaptic responses and the conductance of back-propagating action potentials in, for example, neuronal cells or muscle cells. As the PCIP proteins of the present invention modulate potassium channel mediated activities, they may be useful as novel diagnostic and therapeutic agents for potassium channel associated disorders.

As used herein, a "potassium channel associated disorder" includes a disorder, disease or condition which is characterized by a misregulation of a potassium channel mediated activity. Potassium channel associated disorders can detrimentally affect conveyance of sensory impulses from the periphery to the brain and/or conductance of motor impulses from the brain to the periphery; integration of reflexes; interpretation of sensory impulses; and emotional, intellectual (e.g., learning and memory), or motor processes.

Examples of potassium channel associated disorders include neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, epileptic syndromes, and Jakob-Creutzfieldt disease; psychiatric disorders, e.g., depression, schizophrenic disorders, Korsakoff's psychosis, mania, anxiety disorders, bipolar affective disorders, or phobic disorders; learning or memory disorders, e.g., amnesia or age-related memory loss; neurological disorders, e.g., migraine; pain disorders, e.g., hyperalgesia or pain associated with muscoloskeletal disorders; spinal cord injury; stroke; and head trauma.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

For example, the family of PCIP proteins comprise at least one "calcium binding domain". As used herein, the term "calcium binding domain" includes an amino acid domain, e.g., an EF hand (Baimbridge K. G. et al. (1992) *TINS* 15(8): 303–308), which is involved in calcium binding. Preferably, a calcium binding domain has a sequence, which is substantially identical to the consensus sequence:

EQ..OO..ODKDGDG.O...EF..OO. (SEQ ID NO:41).

O can be I, L, V or M, and "." indicates a position with no strongly preferred residue. Each residue listed is present in more than 25% of sequences, and those underlined are present in more than 80% of sequences. Amino acid residues 126–154 and 174–202 of the human 1v protein, amino acid residues 126–154 and 174–202 of the rat 1v protein, amino acid residues 137–165 and 185–213 of the rat 1vl protein, amino acid residues 142–170 of the rat 1vn protein, amino acid residues 126–154 and 174–202 of the mouse 1v protein, amino acid residues 137–165 and 185–213 of the mouse 1vl protein, amino acid residues 144–172, 180–208, and 228–256 of the human 9ql protein, amino acid residues 126–154, 162–190, and 210–238 of the human 9qm protein, amino acid residues 94–122, 130–158, and 178–206 of the human 9qs protein, amino acid residues 126–154, 162–190, and 210–238 of the rat 9qm protein, amino acid residues 131–159, 167–195, and 215–243 of the rat 9ql protein, amino acid residues 126–154, 162–190, and 210–238 of the rat 9qc protein, amino acid residues 99–127, 135–163, and 183–211 of the rat 8t protein, amino acid residues 144–172, 180–208, and 228–256 of the mouse 9ql protein, amino acid residues 94–122, 130–158, and 178–206 of the monkey 9qs protein, amino acid residues 94–122, 130–158, and 178–206 of the human p19 protein, amino acid residues 19–47 and 67–95 of the rat p19 protein, and amino acid residues 130–158, 166–194, and 214–242 of the mouse p19 protein comprise calcium binding domains (EF hands) (see FIG. 21).

Isolated proteins of the present invention, preferably 1v, 9q, p 19, and W28559 proteins, have an amino acid sequence sufficiently identical to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40 or are encoded by a nucleotide sequence sufficiently identical to SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% identity, preferably 60% identity, more preferably 70%–80%, and even more preferably 90–95% identity across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% identity and share a common functional activity are defined herein as sufficiently identical.

As used interchangeably herein, a "PCIP activity", "biological activity of PCIP" or "functional activity of PCIP", refers to an activity exerted by a PCIP protein, polypeptide or nucleic acid molecule on a PCIP responsive cell or on a PCIP protein substrate, as determined in vivo, or in vitro, according to standard techniques. In one embodiment, a PCIP activity is a direct activity, such as an association with a PCIP-target molecule. As used herein, a "target molecule" or "binding partner" is a molecule with which a PCIP protein binds or interacts in nature, such that PCIP-mediated function is achieved. A PCIP target molecule can be a non-PCIP molecule or a PCIP protein or polypeptide of the present invention. In an exemplary embodiment, a PCIP target molecule is a PCIP ligand. Alternatively, a PCIP activity is an indirect activity, such as a cellular signaling activity mediated by interaction of the PCIP protein with a PCIP ligand. The biological activities of PCIP are described herein. For example, the PCIP proteins of the present invention can have one or more of the following activities: (1) interaction with (e.g., bind to) a potassium channel protein or portion thereof; (2) regulation of the phosphorylation state of a potassium channel protein or portion thereof, (3) association with (e.g., bind) calcium and can, for example, act as calcium dependent kinases, e.g., phosphorylate a potassium channel or a G-protein coupled receptor in a calcium-dependent manner; (4) modulation of a potassium channel mediated activity in a cell (e.g., a neuronal cell) to, for example, beneficially affect the cell; (5) modulation of the release of neurotransmitters; (6) modulation of membrane excitability; (7) influence on the resting potential of membranes; (8) modulation of wave forms and frequencies of action potentials; and (9) modulation of thresholds of excitation.

Accordingly, another embodiment of the invention features isolated PCIP proteins and polypeptides having a PCIP activity. Preferred proteins are PCIP proteins having at least one calcium binding domain and, preferably, a PCIP activity. Other preferred proteins are PCIP proteins having at least one calcium binding domain, and are, preferably, encoded by a nucleic acid molecule having a nucleotide sequence which hybridizes under stringent hybridization conditions to a nucleic acid molecule comprising the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47.

The PCIP molecules of the present invention were initially identified from a rat midbrain cDNA library based on their ability, as determined using yeast two-hybrid assays (described in detail in Example 1), to interact with the amino-terminal 180 amino acids of rat Kv4.3 subunit. Further binding studies with other potassium subunits were performed to demonstrate specificity of the PCIP for Kv4.3 and Kv4.2. In situ localization, immuno-histochemical methods, co-immunoprecipitation and patch clamping methods were then used to clearly demonstrate that the PCIPs of the present invention interact with and modulate the activity of potassium channels, particularly those comprising a 4.3 or 4.2 subunit.

Several novel human, mouse and rat PCIP family members have been identified, referred to herein as 1v, 9q, p19, and W28559 proteins and nucleic acid molecules. The human, rat, and mouse cDNAs encoding the 1v polypeptide are represented by SEQ ID NOs: 13, and 5, and shown in FIGS. 1, 2, and 3, respectively. In the brain, 1v mRNA is highly expressed in neocortical and hippocampal interneurons, in the thalamic reticular nucleus and medial habenula, in basal forebrain and striatal cholinergic neurons, in the superior colliculus, and in cerebellar granule cells. The 1v polypeptide is highly expressed in the somata, dendrites, axons and axon terminals of cells that express 1v mRNA. Splice variants of the 1v gene have been identified in rat and mouse and are represented by SEQ ID NOs: 7, 9, and 11 and shown in FIGS. 4, 5, and 6, respectively. 1v polypeptide interacts with potassium channels comprising Kv4.3 or kv4.2 subunits, but not with Kv1.1 subunits. As determined by Northern blot, the 1v transcripts (mRNA) are expressed predominantly in the heart and the brain.

The 8t cDNA (SEQ ID NO: 29) encodes a polypeptide having a molecular weight of approximately 26 kD corresponding to SEQ ID NO:30 (see FIG. 15). The 8t polypeptide interacts with potassium channel comprising Kv4.3 or Kv4.2 subunits, but not with Kv1.1 subunits. As determined by Northern blot and in situ data, the 8t mRNA is expressed predominantly in the heart and the brain. The 8t cDNA is a splice variant of 9q.

Human, rat, monkey, and mouse 9q cDNA was also isolated. Splice variants include human 9ql (SEQ ID NO:13; FIG. 7) rat 9ql (SEQ ID NO:15; FIG. 8), mouse 9ql (SEQ ID NO:17; FIG. 9), human 9qm (SEQ ID NO:19; FIG. 10), rat 9qm (SEQ ID NO:21; FIG. 11), human 9qs (SEQ ID NO:23; FIG. 12), monkey 9qs (SEQ ID NO:25; FIG. 13), and rat 9qc (SEQ ID NO:27; FIG. 14). The genomic DNA sequence of 9q has also be determined. Exon 1 and its flanking intron sequences (SEQ ID NO:46) are ahown in FIG. 22A. Exons 2–11 and the flanking intron sequences (SEQ ID NO:47) are shown in FIG. 22B. 9q polypeptides interact with potassium channels comprising Kv4.3 or Kv4.2 subunits, but not with Kv1.1 subunits. As determined by Northern blot and in situ data, the 9q proteins are expressed predominantly in the heart and the brain. In the brain, 9q mRNA is highly expressed in the neostriatum, hippocampal formation, neocortical pyramidal cells and interneurons, and in the thalamus, superior colliculus, and cerebellum.

Human, rat, and mouse P19 cDNA was also isolated. Human P19 is shown in SEQ ID NO:31 and FIG. 16 (the 5' sequence); and in SEQ ID NO:39 and FIG. 20 (the 3' sequence). Rat P19 is shown in SEQ ID NO:33 and FIG. 17, and mouse P19 is shown in SEQ ID NO:35 and FIG. 18. P19 polypeptides interact with potassium channels comprising Kv4.3 or Kv4.2 subunits, but not with Kv1.1 subunits. As determined by northern blot aalysis, the P 19 transcripts (mRNA) are expressed predominantly in the brain.

Finally, a partial human paralog of the PCIP molecules was identified. This paralog is referred to herein as W28559 and is shown in SEQ ID NO:37 and FIG. 19.

The sequences of the present invention are summarized below, in Table I.

TABLE I

Novel Polynucleotides and Polypeptides of the Present Invention (full length except where noted)

| PCIP | Nucleic Acid Molecule Form | Source | SEQ ID NO: DNA | SEQ ID NO: PROTEIN | ATCC |
|---|---|---|---|---|---|
| 1v | 1v | human (225–875)* | 1 | 2 | 98994 |
| | 1v | rat (210–860) | 3 | 4 | 98946 |
| | 1v | mouse (477–1127) | 5 | 6 | 98945 |
| | 1vl | rat (31–714) | 7 | 8 | 98942 |
| | 1vl | mouse (77–760) | 9 | 10 | 98943 |
| | 1vn (partial) | rat (345–955) | 11 | 12 | 98944 |
| 9q | Genomic DNA sequence (Exon 1 and flanking intron sequences) | human | 46 | | |
| | Genomic DNA sequence (Exons 2–11 and flanking intron sequences) | human | 47 | | |
| | 9ql | human (207–1019) | 13 | 14 | 98993 98991 |
| | 9ql (partial) | rat (2–775) | 15 | 16 | 98948 |
| | 9ql | mouse (181–993) | 17 | 18 | 98937 |
| | 9qm | human (207–965) | 19 | 20 | 98993 98991 |
| | 9qm | rat (214–972) | 21 | 22 | 98941 |
| | 9qs | human (207–869) | 23 | 24 | 98951 |
| | 9qs | monkey (133–795) | 25 | 26 | 98950 |
| | 9qc | rat (208–966) | 27 | 28 | 98947 |
| | 8t (partial) | rat (1–678) | 29 | 30 | 98939 |
| p19 | p195 (partial) | Human (12–440) | 31 | 32 | 98938 |
| | p19 (partial) | rat (1–330) | 33 | 34 | 98936 |
| | p19 | mouse (49–819) | 35 | 36 | 98940 |

TABLE I-continued

Novel Polynucleotides and Polypeptides of the Present Invention
(full length except where noted)

| PCIP | Nucleic Acid Molecule Form | Source | SEQ ID NO: DNA | SEQ ID NO: PROTEIN | ATCC |
|---|---|---|---|---|---|
| | p193 (partial) | human (2–127) | 39 | 40 | 98949 |
| W28559 | W28559 (partial) | human (2–380) | 37 | 38 | |

*The cordinates of the coding sequence are shown in parenthesis.
The first column indicates the four families of PCIPs which were identified and column 2 indicates the various nucleic acid forms identified for each family.

Plasmids containing the nucleotide sequences encoding human, rat and monkey PCIPs were deposited with American Type Culture Collection (ATCC), 10801 University Boulevard, Manassas, Va. 20110-2209, on Nov. 17, 1998, and assigned the Accession Numbers described above. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112.

Various aspects of the invention are described in further detail in the following subsections:

I. Isolated Nucleic Acid Molecules

One aspect of the invention pertains to isolated nucleic acid molecules that encode PCIP proteins or biologically active portions thereof, as well as nucleic acid fragments sufficient for use as hybridization probes to identify PCIP-encoding nucleic acid molecules (e.g., PCIP mRNA) and fragments for use as PCR primers for the amplification or mutation of PCIP nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PCIP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion thereof, can be isolated using standard molecular biology techniques and the sequence information provided herein. Using all or portion of the nucleic acid sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, as a hybridization probe, PCIP nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 can be isolated by the polymerase chain reaction (PCR) using synthetic oligonucleotide primers designed based upon the sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to PCIP nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion of any of these nucleotide sequences.

In another preferred embodiment, an isolated nucleic acid molecule of the invention comprises a nucleic acid molecule which is a complement of the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion of any of these nucleotide sequences. A nucleic acid molecule which is complementary to the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO: 19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, is one which is sufficiently complementary to the nucleotide sequence shown in SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, such that it can hybridize to the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95% or more identical to the entire length of the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the entire length of the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion of any of these nucleotide sequences.

Moreover, the nucleic acid molecule of the invention can comprise only a portion of the nucleic acid sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, for example a fragment which can be used as a probe or primer or a fragment encoding a biologically active portion of a PCIP protein. The nucleotide sequence determined from the cloning of the PCIP gene allows for the generation of probes and primers designed for use in identifying and/or cloning other PCIP family members, as well as PCIP homologues from other species.

The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, of an anti-sense sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or of a naturally occurring allelic variant or mutant of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In an exemplary embodiment, a nucleic acid molecule of the present invention comprises a nucleotide sequence which is 350–400, 400–450, 450–500, 500–550, 550–600, 600–650, 650–700, 700–750, 750–800, 800–850, 850–900, 949, 950–1000, or more nucleotides in length and hybridizes under stringent hybridization conditions to a nucleic acid molecule of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994.

Probes based on the PCIP nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a PCIP protein, such as by measuring a level of a PCIP-encoding nucleic acid in a sample of cells from a subject e.g., detecting PCIP mRNA levels or determining whether a genomic PCIP gene has been mutated or deleted.

A nucleic acid fragment encoding a "biologically active portion of a PCIP protein" can be prepared by isolating a portion of the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, which encodes a polypeptide having a PCIP biological activity (the biological activities of the PCIP proteins are described herein), expressing the encoded portion of the PCIP protein (e.g., by recombinant expression in vitro) and assessing the activity of the encoded portion of the PCIP protein.

The invention further encompasses nucleic acid molecules that differ from the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47 or the nucleotide sequence of the DNA insert of the plasmid deposited with 98936, 98937, 98938, 98939, 98940, 98941, 98942, 98943, 98944, 98945, 98946, 98947, 98948, 98949, 98950, 98951, 98991, 98993, or 98994, due to degeneracy of the genetic code and thus encode the same PCIP proteins as those encoded by the nucleotide sequence shown in SSEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47 or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In another embodiment, an isolated nucleic acid molecule of the invention has a nucleotide sequence encoding a protein having an amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40.

In addition to the PCIP nucleotide sequences shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, it will be appreciated by those skilled in the art that DNA sequence polymorphisms that lead to changes in the amino acid sequences of the PCIP proteins may exist within a population (e.g., the human population). Such genetic polymorphism in the PCIP genes may exist among individuals within a population due to natural allelic variation. As used herein, the terms "gene" and "recombinant gene" refer to nucleic acid molecules which include an open reading frame encoding a PCIP protein, preferably a mammalian PCIP protein, and can further include non-coding regulatory sequences, and introns.

Allelic variants of human PCIP include both functional and non-functional PCIP proteins. Functional allelic variants are naturally occurring amino acid sequence variants of the human PCIP protein that maintain the ability to bind a PCIP ligand and/or modulate any of the PCIP activities described herein. Functional allelic variants will typically contain only conservative substitution of one or more amino acids of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40 or substitution, deletion or insertion of non-critical residues in non-critical regions of the protein.

Non-functional allelic variants are naturally occurring amino acid sequence variants of the human PCIP protein that do not have the ability to either bind a PCIP ligand and/or modulate any of the PCIP activities described herein. Non-functional allelic variants will typically contain a non-conservative substitution, a deletion, or insertion or premature truncation of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40 or a substitution, insertion or deletion in critical residues or critical regions.

The present invention further provides non-human orthologues of the human PCIP protein. Orthologues of the human PCIP protein are proteins that are isolated from non-human organisms and possess the same PCIP ligand binding and/or modulation of potassium channel mediated activities of the human PCIP protein. Orthologues of the human PCIP protein can readily be identified as comprising an amino acid sequence that is substantially identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40.

Moreover, nucleic acid molecules encoding other PCIP family members and, thus, which have a nucleotide sequence which differs from the PCIP sequences of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 are intended to be within the scope of the invention. For example, another PCIP cDNA can be identified based on the nucleotide sequence of human PCIP. Moreover, nucleic acid molecules encoding PCIP proteins from different species, and thus which have a nucleotide sequence which differs from the PCIP sequences of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47 or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 are intended to be within the scope of the invention. For example, a mouse PCIP cDNA can be identified based on the nucleotide sequence of a human PCIP.

Nucleic acid molecules corresponding to natural allelic variants and homologues of the PCIP cDNAs of the invention can be isolated based on their homology to the PCIP nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47 or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In other embodiment, the nucleic acid is at least 30, 50, 100, 150, 200, 250, 300, 307, 350, 400, 450, 500, 550, 600, 650, 700, 750, 800, 850, 900, 949, or 950 nucleotides in length. As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45C, followed by one or more washes in 0.2×SSC, 0.1% SDS at 50° C., preferably at 55° C., and more preferably at 60° C. or 65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the PCIP sequences that may exist in the population, the skilled artisan will further appreciate that changes can be introduced by mutation into the nucleotide sequences of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, thereby leading to changes in the amino acid sequence of the encoded PCIP proteins, without altering the functional ability of the PCIP proteins. For example, nucleotide substitutions leading to amino acid substitutions at "non-essential" amino acid residues can be made in the sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. A "non-essential" amino acid residue is a residue that can be altered from the wild-type sequence of PCIP (e.g., the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40) without altering the biological activity, whereas an "essential" amino acid residue is required for biological activity. For example, amino acid residues that are conserved among the PCIP proteins of the present invention, are predicted to be particularly unamenable to alteration. Furthermore, additional amino acid residues that are conserved between the PCIP proteins of the present invention and other members of the PCIP family of proteins are not likely to be amenable to alteration.

Accordingly, another aspect of the invention pertains to nucleic acid molecules encoding PCIP proteins that contain changes in amino acid residues that are not essential for activity. Such PCIP proteins differ in amino acid sequence from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95% or more identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO: 18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40.

An isolated nucleic acid molecule encoding a PCIP protein homologous to the protein of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40 can be created by introducing one or more nucleotide substitutions, additions or deletions into the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, such that one or more amino acid substitutions, additions or deletions are introduced into the encoded protein. Mutations can be introduced into SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO: 19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PCIP protein is preferably replaced with another amino acid residue from the same side chain family. Alternatively, in another embodiment, mutations can be introduced randomly along all or part of a PCIP coding sequence, such as by saturation mutagenesis, and the resultant mutants can be screened for PCIP biological activity to identify mutants that retain activity. Following mutagenesis of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, the encoded protein can be expressed recombinantly and the activity of the protein can be determined.

In a preferred embodiment, a mutant PCIP protein can be assayed for the ability to (1) interact with (e.g., bind to) a potassium channel protein or portion thereof; (2) regulate the phosphorylation state of a potassium channel protein or portion thereof; (3) associate with (e.g., bind) calcium and, for example, act as a calcium dependent kinase, e.g., phosphorylate a potassium channel in a calcium-dependent manner; (4) modulate a potassium channel mediated activity in a cell (e.g., a neuronal cell) to, for example, beneficially affect the cell; (5) modulate the release of neurotransmitters; (6) modulate membrane excitability; (7) influence the resting potential of membranes; (8) modulate wave forms and frequencies of action potentials; and (9) modulate thresholds of excitation.

In addition to the nucleic acid molecules encoding PCIP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PCIP coding strand, or to only a portion thereof. In one embodiment, an antisense nucleic acid molecule is antisense to a "coding region" of the coding strand of a nucleotide sequence encoding PCIP. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding PCIP. The term "noncoding region" refers to 5' and 3' sequences which flank the coding region that are not translated into amino acids (i.e., also referred to as 5' and 3' untranslated regions).

Given the coding strand sequences encoding PCIP disclosed herein, antisense nucleic acids of the invention can be designed according to the rules of Watson and Crick base pairing. The antisense nucleic acid molecule can be complementary to the entire coding region of PCIP mRNA, but more preferably is an oligonucleotide which is antisense to only a portion of the coding or noncoding region of PCIP mRNA. For example, the antisense oligonucleotide can be complementary to the region surrounding the translation start site of PCIP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PCIP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave PCIP mRNA transcripts to thereby inhibit translation of PCIP mRNA. A ribozyme having specificity for a PCIP-encoding nucleic acid can be designed based upon the nucleotide sequence of a PCIP cDNA disclosed herein (i.e., SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994). For example, a derivative of a Tetrahymena L-19 IVS RNA can be constructed in which the nucleotide sequence of the active site is complementary to the nucleotide sequence to be cleaved in a PCIP-encoding mRNA. See, e.g., Cech et al. U.S. Pat. No. 4,987,071; and Cech et al. U.S. Pat. No. 5,116,742. Alternatively, PCIP mRNA can be used to select a catalytic RNA having a specific ribonuclease activity from a pool of RNA molecules. See, e.g., Bartel, D. and Szostak, J. W. (1993) *Science* 261:1411–1418.

Alternatively, PCIP gene expression can be inhibited by targeting nucleotide sequences complementary to the regulatory region of the PCIP (e.g., the PCIP promoter and/or enhancers) to form triple helical structures that prevent transcription of the PCIP gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the PCIP nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of PCIP nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of PCIP nucleic acid molecules can also be used in the analysis of single base pair mutations in a gene, (e.g., by PNA-directed PCR clamping); as 'artificial restriction enzymes' when used in combination with other enzymes, (e.g., S1nucleases (Hyrup B. (1996) supra)); or as probes or primers for DNA sequencing or hybridization (Hyrup B. et al. (1996) supra; Perry-O'Keefe supra).

In another embodiment, PNAs of PCIP can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of PCIP nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated PCIP Proteins and Anti-PCIP Antibodies

One aspect of the invention pertains to isolated PCIP proteins, and biologically active portions thereof, as well as polypeptide fragments suitable for use as immunogens to raise anti-PCIP antibodies. In one embodiment, native PCIP proteins can be isolated from cells or tissue sources by an appropriate purification scheme using standard protein purification techniques. In another embodiment, PCIP proteins are produced by recombinant DNA techniques. Alternative to recombinant expression, a PCIP protein or polypeptide can be synthesized chemically using standard peptide synthesis techniques.

An "isolated" or "purified" protein or biologically active portion thereof is substantially free of cellular material or other contaminating proteins from the cell or tissue source from which the PCIP protein is derived, or substantially free from chemical precursors or other chemicals when chemically synthesized. The language "substantially free of cellular material" includes preparations of PCIP protein in which the protein is separated from cellular components of the cells from which it is isolated or recombinantly produced. In one embodiment, the language "substantially free of cellular material" includes preparations of PCIP protein having less than about 30% (by dry weight) of non-PCIP protein (also referred to herein as a "contaminating protein"), more preferably less than about 20% of non-PCIP protein, still more preferably less than about 10% of non-PCIP protein, and most preferably less than about 5% non-PCIP protein. When the PCIP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PCIP protein in which the protein is separated from chemical precursors or other chemicals which are involved in the synthesis of the protein. In one embodiment, the language "substantially free of chemical precursors or other chemicals" includes preparations of PCIP protein having less than about 30% (by dry weight) of chemical precursors or non-PCIP chemicals, more preferably less than about 20% chemical precursors or non-PCIP chemicals, still more preferably less than about 10% chemical precursors or non-PCIP chemicals, and most preferably less than about 5% chemical precursors or non-PCIP chemicals.

As used herein, a "biologically active portion" of a PCIP protein includes a fragment of a PCIP protein which participates in an interaction between a PCIP molecule and a non-PCIP molecule. Biologically active portions of a PCIP protein include peptides comprising amino acid sequences sufficiently identical to or derived from the amino acid sequence of the PCIP protein, e.g., the amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40, which include less amino acids than the full length PCIP proteins, and exhibit at least one activity of a PCIP protein. Typically, biologically active portions comprise a domain or motif with at least one activity of the PCIP protein, e.g., binding of a potassium channel subunit. A biologically active portion of a PCIP protein can be a polypeptide which is, for example, 10, 25, 50, 100, 200, or more amino acids in length. Biologically active portions of a PCIP protein can be used as targets for developing agents which modulate a potassium channel mediated activity.

In one embodiment, a biologically active portion of a PCIP protein comprises at least one calcium binding domain.

It is to be understood that a preferred biologically active portion of a PCIP protein of the present invention may contain at least one of the above-identified structural domains. A more preferred biologically active portion of a PCIP protein may contain at least two of the above-identified structural domains. Moreover, other biologically active portions, in which other regions of the protein are deleted, can be prepared by recombinant techniques and evaluated for one or more of the functional activities of a native PCIP protein.

In a preferred embodiment, the PCIP protein has an amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40. In other embodiments, the PCIP protein is substantially homologous to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO: 18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40, and retains the functional activity of the protein of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40, yet differs in amino acid sequence due to natural allelic variation or mutagenesis, as described in detail in subsection I above. Accordingly, in another embodiment, the PCIP protein is a protein which comprises an amino acid sequence at least about 50%, 55%, 60%, 65%, 70%, 75%, 80%, 85%, 90%, 95% or more identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the PCIP amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40 having 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to PCIP nucleic acid molecules of the invention. BLAST protein searches can be performed with the XBLAST program, score=50, wordlength=3 to obtain amino acid sequences homologous to PCIP protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The invention also provides PCIP chimeric or fusion proteins. As used herein, a PCIP "chimeric protein" or "fusion protein" comprises a PCIP polypeptide operatively linked to a non-PCIP polypeptide. An "PCIP polypeptide" refers to a polypeptide having an amino acid sequence corresponding to PCIP, whereas a "non-PCIP polypeptide" refers to a polypeptide having an amino acid sequence corresponding to a protein which is not substantially homologous to the PCIP protein, e.g., a protein which is different from the PCIP protein and which is derived from the same or a different organism. Within a PCIP fusion protein the PCIP polypeptide can correspond to all or a portion of a PCIP protein. In a preferred embodiment, a PCIP fusion protein comprises at least one biologically active portion of a PCIP protein. In another preferred embodiment, a PCIP fusion protein comprises at least two biologically active portions of a PCIP protein. Within the fusion protein, the term "operatively linked" is intended to indicate that the PCIP polypeptide and the non-PCIP polypeptide are fused in-frame to each other. The non-PCIP polypeptide can be fused to the N-terminus or C-terminus of the PCIP polypeptide.

For example, in one embodiment, the fusion protein is a GST-PCIP fusion protein in which the PCIP sequences are fused to the C-terminus of the GST sequences. Such fusion proteins can facilitate the purification of recombinant PCIP.

In another embodiment, the fusion protein is a PCIP protein containing a heterologous signal sequence at its N-terminus. In certain host cells (e.g., mammalian host cells), expression and/or secretion of PCIP can be increased through use of a heterologous signal sequence.

The PCIP fusion proteins of the invention can be incorporated into pharmaceutical compositions and administered to a subject in vivo. The PCIP fusion proteins can be used to affect the bioavailability of a PCIP substrate. Use of PCIP fusion proteins may be useful therapeutically for the treatment of potassium channel associated disorders such as CNS disorders, e.g., neurodegenerative disorders such as Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy and Jakob-Creutzfieldt disease; psychiatric disorders, e.g., depression, schizophrenic disorders, Korsakoff's psychosis, mania, anxiety disorders, or phobic disorders; learning or memory disorders, e.g., amnesia or age-related memory loss; and neurological disorders; e.g., migraine.

Moreover, the PCIP-fusion proteins of the invention can be used as immunogens to produce anti-PCIP antibodies in a subject, to purify PCIP ligands and in screening assays to identify molecules which inhibit the interaction of PCIP with a PCIP substrate.

Preferably, a PCIP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PCIP-encoding nucleic acid can be cloned into such an expression vector such that the fusion moiety is linked in-frame to the PCIP protein.

The present invention also pertains to variants of the PCIP proteins which function as either PCIP agonists (mimetics) or as PCIP antagonists. Variants of the PCIP proteins can be generated by mutagenesis, e.g., discrete point mutation or truncation of a PCIP protein. An agonist of the PCIP proteins can retain substantially the same, or a subset, of the biological activities of the naturally occurring form of a PCIP protein. An antagonist of a PCIP protein can inhibit one or more of the activities of the naturally occurring form of the PCIP protein by, for example, competitively modulating a potassium channel mediated activity of a PCIP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PCIP protein.

In one embodiment, variants of a PCIP protein which function as either PCIP agonists (mimetics) or as PCIP antagonists can be identified by screening combinatorial libraries of mutants, e.g., truncation mutants, of a PCIP protein for PCIP protein agonist or antagonist activity. In one embodiment, a variegated library of PCIP variants is generated by combinatorial mutagenesis at the nucleic acid level and is encoded by a variegated gene library. A variegated library of PCIP variants can be produced by, for example, enzymatically ligating a mixture of synthetic oligonucleotides into gene sequences such that a degenerate set of potential PCIP sequences is expressible as individual polypeptides, or alternatively, as a set of larger fusion proteins (e.g., for phage display) containing the set of PCIP sequences therein. There are a variety of methods which can be used to produce libraries of potential PCIP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PCIP sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a PCIP protein coding sequence can be used to generate a variegated population of PCIP fragments for screening and subsequent selection of variants of a PCIP protein. In one embodiment, a library of coding sequence fragments can be generated by treating a double stranded PCR fragment of a PCIP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PCIP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PCIP proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PCIP variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated PCIP library. For example, a library of expression vectors can be transfected into a cell line which ordinarily possesses a potassium channel mediated activity. The effect of the PCIP mutant on the potassium channel mediated activity can then be detected, e.g., by any of a number of enzymatic assays or by detecting the release of a neurotransmitter. Plasmid DNA can then be recovered from the cells which score for inhibition, or alternatively, potentiation of the potassium channel mediated activity, and the individual clones further characterized.

An isolated PCIP protein, or a portion or fragment thereof, can be used as an immunogen to generate antibodies that bind PCIP using standard techniques for polyclonal and monoclonal antibody preparation. A full-length PCIP protein can be used or, alternatively, the invention provides antigenic peptide fragments of PCIP for use as immunogens. The antigenic peptide of PCIP comprises at least 8 amino acid residues of the amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40 and encompasses an epitope of PCIP such that an antibody raised against the peptide forms a specific immune complex with PCIP. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of PCIP that are located on the surface of the protein, e.g., hydrophilic regions, as well as regions with high antigenicity.

A PCIP immunogen typically is used to prepare antibodies by immunizing a suitable subject, (e.g., rabbit, goat, mouse or other mammal) with the immunogen. An appropriate immunogenic preparation can contain, for example, recombinantly expressed PCIP protein or a chemically synthesized PCIP polypeptide. The preparation can further include an adjuvant, such as Freund's complete or incomplete adjuvant, or similar immunostimulatory agent. Immunization of a suitable subject with an immunogenic PCIP preparation induces a polyclonal anti-PCIP antibody response.

Accordingly, another aspect of the invention pertains to anti-PCIP antibodies. The term "antibody" as used herein refers to immunoglobulin molecules and immunologically active portions of immunoglobulin molecules, i.e., molecules that contain an antigen binding site which specifically binds (immunoreacts with) an antigen, such as PCIP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind PCIP. The term "monoclonal antibody" or "monoclonal antibody composition", as used herein, refers to a population of antibody molecules that contain only one species of an antigen binding site capable of immunoreacting with a particular epitope of PCIP. A monoclonal antibody composition thus typically displays a single binding affinity for a particular PCIP protein with which it immunoreacts.

Polyclonal anti-PCIP antibodies can be prepared as described above by immunizing a suitable subject with a PCIP immunogen. The anti-PCIP antibody titer in the immunized subject can be monitored over time by standard techniques, such as with an enzyme linked immunosorbent assay (ELISA) using immobilized PCIP. If desired, the antibody molecules directed against PCIP can be isolated from the mammal (e.g., from the blood) and further purified by well known techniques, such as protein A chromatography to obtain the IgG fraction. At an appropriate time after immunization, e.g., when the anti-PCIP antibody titers are highest, antibody-producing cells can be obtained from the subject and used to prepare monoclonal antibodies by standard techniques, such as the hybridoma technique originally described by Kohler and Milstein (1975) Nature 256:495–497) (see also, Brown et al. (1981) J. Immunol. 127:539–46; Brown et al. (1980) J. Biol. Chem. 255:4980–83; Yeh et al. (1976) Proc. Natl. Acad. Sci. USA 76:2927–31; and Yeh et al. (1982) Int. J. Cancer 29:269–75), the more recent human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387–402; M. L. Gefter et al. (1977) Somatic Cell Genet. 3:231–36). Briefly, an immortal cell line (typically a myeloma) is fused to lymphocytes (typically splenocytes) from a mammal immunized with a PCIP immunogen as described above, and the culture supernatants of the resulting hybridoma cells are screened to identify a hybridoma producing a monoclonal antibody that binds PCIP.

Any of the many well known protocols used for fusing lymphocytes and immortalized cell lines can be applied for the purpose of generating an anti-PCIP monoclonal antibody (see, e.g., G. Galfre et al. (1977) Nature 266:55052; Gefter et al. Somatic Cell Genet., cited supra; Lerner, Yale J. Biol. Med., cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PCIP, e.g., using a standard ELISA assay.

Alternative to preparing monoclonal antibody-secreting hybridomas, a monoclonal anti-PCIP antibody can be identified and isolated by screening a recombinant combinatorial immunoglobulin library (e.g., an antibody phage display library) with PCIP to thereby isolate immunoglobulin library members that bind PCIP. Kits for generating and screening phage display libraries are commercially available (e.g., the *Pharmacia Recombinant Phage Antibody System*, Catalog No. 27-9400-01; and the Stratagene SurfZAP™ Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226: 889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-PCIP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) Science 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-PCIP antibody (e.g., monoclonal antibody) can be used to isolate PCIP by standard techniques, such as affinity chromatography or immunoprecipitation. An anti-PCIP antibody can facilitate the purification of natural PCIP from cells and of recombinantly produced PCIP expressed in host cells. Moreover, an anti-PCIP antibody can be used to detect PCIP protein (e.g., in a cellular lysate or cell supernatant) in order to evaluate the abundance and pattern of expression of the PCIP protein. Anti-PCIP antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a PCIP protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PCIP proteins, mutant forms of PCIP proteins, fusion proteins, and the like).

The recombinant expression vectors of the invention can be designed for expression of PCIP proteins in prokaryotic or eukaryotic cells. For example, PCIP proteins can be expressed in bacterial cells such as E. coli, insect cells (using baculovirus expression vectors) yeast cells or mammalian cells. Suitable host cells are discussed further in Goeddel, *Gene Expression Technology. Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:3140), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in PCIP activity assays, (e.g., direct assays or competitive assays described in detail below), or to generate antibodies specific for PCIP proteins, for example. In a preferred embodiment, a PCIP fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion E coli expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS 174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al., (1992) *Nucleic Acids Res.* 20:2111–2118). Such alteration of nucleic acid sequences of the invention can be carried out by standard DNA synthesis techniques.

In another embodiment, the PCIP expression vector is a yeast expression vector. Examples of vectors for expression in yeast S. cerivisae include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, PCIP proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Baneiji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PCIP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PCIP protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory ManuaL 2nd, ed, Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a PCIP protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a PCIP protein. Accordingly, the invention further provides methods for producing a PCIP protein using the host cells of the invention. In one embodiment, the method comprises culturing the host cell of invention (into which a recombinant expression vector encoding a PCIP protein has been introduced) in a suitable medium such that a PCIP protein is produced. In another embodiment, the method further comprises isolating a PCIP protein from the medium or the host cell.

The host cells of the invention can also be used to produce non-human transgenic animals. For example, in one embodiment, a host cell of the invention is a fertilized oocyte or an embryonic stem cell into which PCIP-coding sequences have been introduced. Such host cells can then be used to create non-human transgenic animals in which exogenous PCIP sequences have been introduced into their genome or homologous recombinant animals in which endogenous PCIP sequences have been altered. Such animals are useful for studying the function and/or activity of a PCIP and for identifying and/or evaluating modulators of PCIP activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous PCIP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a PCIP-encoding nucleic acid into the male pronuclei of a fertilized oocyte, e.g., by microinjection, retroviral infection, and allowing the oocyte to develop in a pseudopregnant female foster animal. The PCIP cDNA sequence of SEQ ID NO:1, SEQ ID NO:3 SEQ ID NO:5, SEQ ID NO:7, SEQ ID NO:9, SEQ ID NO:1, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47 can be introduced as a transgene into the genome of a non-human animal. Alternatively, a nonhuman homologue of a human PCIP gene, such as a mouse or rat PCIP gene, can be used as a transgene. Alternatively, a PCIP gene homologue, such as another PCIP family member, can be isolated based on hybridization to the PCIP cDNA sequences of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47 or the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 (described further in subsection I above) and used as a transgene. Intronic sequences and polyadenylation signals can also be included in the transgene to increase the efficiency of expression of the transgene. A tissue-specific regulatory sequence(s) can be operably linked to a PCIP transgene to direct expression of a PCIP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals.

A transgenic founder animal can be identified based upon the presence of a PCIP transgene in its genome and/or expression of PCIP mRNA in tissues or cells of the animals. A transgenic founder animal can then be used to breed additional animals carrying the transgene. Moreover, transgenic animals carrying a transgene encoding a PCIP protein can further be bred to other transgenic animals carrying other transgenes.

To create a homologous recombinant animal, a vector is prepared which contains at least a portion of a PCIP gene into which a deletion, addition or substitution has been introduced to thereby alter, e.g., functionally disrupt, the PCIP gene. The PCIP gene can be a human gene (e.g., the cDNA of SEQ ID NO:1), but more preferably, is a non-human homologue of a human PCIP gene (e.g., the cDNA of SEQ ID NO:3 or 5). For example, a mouse PCIP gene can be used to construct a homologous recombination vector suitable for altering an endogenous PCIP gene in the mouse genome. In a preferred embodiment, the vector is designed such that, upon homologous recombination, the endogenous PCIP gene is functionally disrupted (i.e., no longer encodes a functional protein; also referred to as a "knock out" vector). Alternatively, the vector can be designed such that, upon homologous recombination, the endogenous PCIP gene is mutated or otherwise altered but still encodes functional protein (e.g., the upstream regulatory region can be altered to thereby alter the expression of the endogenous PCIP protein). In the homologous recombination vector, the altered portion of the PCIP gene is flanked at its 5' and 3' ends by additional nucleic acid sequence of the PCIP gene to allow for homologous recombination to occur between the exogenous PCIP gene carried by the vector and an endogenous PCIP gene in an embryonic stem cell. The additional flanking PCIP nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced PCIP gene has homologously recombined with the endogenous PCIP gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The PCIP nucleic acid molecules, fragments of PCIP proteins, and anti-PCIP antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a PCIP protein or an anti-PCIP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a PCIP protein of the invention has one or more of the following activities: (1) interaction with (e.g., bind to) a potassium channel protein or portion thereof; (2) regulation of the phosphorylation state of a potassium channel protein or portion thereof; (3) association with (e.g., bind) calcium and can, for example, act as calcium dependent kinases, e.g., phosphorylate a potassium channel or a G-protein coupled receptor in a calcium-dependent manner; (4) modulation of a potassium channel mediated activity in a cell (e.g., a neuronal cell) to, for example, beneficially affect the cell; (5) modulation of the release of neurotransmitters; (6) modulation of membrane excitability; (7) influence on the resting potential of membranes; (8) modulation of wave forms and frequencies of action potentials; and (9) modulation of thresholds of excitation and, thus, can be used to, for example, (1) modulate the activity of a potassium channel protein or portion thereof; (2) modulate the phosphorylation state of a potassium channel protein or portion thereof; (3) modulate the phosphorylation state of a potassium channel or a G-protein coupled receptor in a calcium-dependent manner; (4) modulate a potassium channel mediated activity in a cell (e.g., a neuronal cell) to, for example, beneficially affect the cell; (5) modulate the release of neurotransmitters; (6) modulate membrane excitability; (7) influence the resting potential of membranes; (8) modulate wave forms and frequencies of action potentials; and (9) modulate thresholds of excitation.

The isolated nucleic acid molecules of the invention can be used, for example, to express PCIP protein (e.g., via a recombinant expression vector in a host cell in gene therapy applications), to detect PCIP mRNA (e.g., in a biological sample) or a genetic alteration in a PCIP gene, and to modulate PCIP activity, as described further below. The PCIP proteins can be used to treat disorders characterized by insufficient or excessive production of a PCIP substrate or production of PCIP inhibitors. In addition, the PCIP proteins can be used to screen for naturally occurring PCIP substrates, to screen for drugs or compounds which modulate PCIP activity, as well as to treat disorders characterized by insufficient or excessive production of PCIP protein or production of PCIP protein forms which have decreased or aberrant activity compared to PCIP wild type protein (e.g., CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy and Jakob-Creutzfieldt disease; psychiatric disorders, e.g., depression, schizophrenic disorders, Korsakoff's psychosis, mania, anxiety disorders, bipolar affective disorders, or phobic disorders; learning or memory disorders, e.g., amnesia or age-related memory loss; neurological disorders, e.g., migraine; pain disorders, e.g., hyperalgesia or pain associated with muscoloskeletal disorders; spinal cord injury; stroke; and head trauma). Moreover, the anti-PCIP antibodies of the invention can be used to detect and isolate PCIP proteins, regulate the bioavailability of PCIP proteins, and modulate PCIP activity.

A. Screening Assays

The invention provides a method (also referred to herein as a "screening assay") for identifying modulators, i.e., candidate or test compounds or agents (e.g., peptides, peptidomimetics, small molecules or other drugs) which bind to PCIP proteins, have a stimulatory or inhibitory effect on, for example, PCIP expression or PCIP activity, or have a stimulatory or inhibitory effect on, for example, the expression or activity of PCIP substrate.

In one embodiment, the invention provides assays for screening candidate or test compounds which are substrates of a PCIP protein or polypeptide or biologically active portion thereof. In another embodiment, the invention provides assays for screening candidate or test compounds which bind to or modulate the activity of a PCIP protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990)*Proc. Natl. Acad. Sci.* 87:6378–6382); (Felici (1991)*J. Mol. Biol.* 222:301–310); (Ladner supra.).

In one embodiment, an assay is a cell-based assay in which a cell which expresses a PCIP protein or biologically active portion thereof is contacted with a test compound and the ability of the test compound to modulate PCIP activity, e.g., binding to a potassium channel or a portion thereof, is determined. Determining the ability of the test compound to modulate PCIP activity can be accomplished by monitoring, for example, the release of a neurotransmitter, e.g., dopamine, form a cell which expresses PCIP such as a neuronal cell, e.g., a substantia nigra neuronal cell. The cell, for example, can be of mammalian origin. Determining the ability of the test compound to modulate the ability of PCIP to bind to a substrate can be accomplished, for example, by coupling the PCIP substrate with a radioisotope or enzymatic label such that binding of the PCIP substrate to PCIP can be determined by detecting the labeled PCIP substrate in a complex. For example, compounds (e.g., PCIP substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., PCIP substrate) to interact with PCIP without the labeling of any of the interactants. For example, a microphysiometer can be used to detect the interaction of a compound with PCIP without the labeling of either the compound or the PCIP. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PCIP.

In another embodiment, an assay is a cell-based assay comprising contacting a cell expressing a PCIP target molecule (e.g., a potassium channel or a fragment thereof) with a test compound and determining the ability of the test compound to modulate (e.g. stimulate or inhibit) the activity of the PCIP target molecule. Determining the ability of the test compound to modulate the activity of a PCIP target molecule can be accomplished, for example, by determining the ability of the PCIP protein to bind to or interact with the PCIP target molecule, e.g., a potassium channel or a fragment thereof.

Determining the ability of the PCIP protein or a biologically active fragment thereof, to bind to or interact with a PCIP target molecule can be accomplished by one of the methods described above for determining direct binding. In a preferred embodiment, determining the ability of the PCIP protein to bind to or interact with a PCIP target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response such as the release of a neurotransmitter.

In yet another embodiment, an assay of the present invention is a cell-free assay in which a PCIP protein or biologically active portion thereof is contacted with a test compound and the ability of the test compound to bind to the PCIP protein or biologically active portion thereof is determined. Preferred biologically active portions of the PCIP proteins to be used in assays of the present invention include fragments which participate in interactions with non-PCIP molecules, e.g., potassium channels or fragments thereof, or fragments with high surface probability scores. Binding of the test compound to the PCIP protein can be determined either directly or indirectly as described above. In a preferred embodiment, the assay includes contacting the PCIP protein or biologically active portion thereof with a known compound which binds PCIP to form an assay mixture, contacting the assay mixture with a test compound, and determining the ability of the test compound to interact with a PCIP protein, wherein determining the ability of the test compound to interact with a PCIP protein comprises determining the ability of the test compound to preferentially bind to PCIP or biologically active portion thereof as compared to the known compound.

In another embodiment, the assay is a cell-free assay in which a PCIP protein or biologically active portion thereof is contacted with a test compound and the ability of the test compound to modulate (e.g., stimulate or inhibit) the activity of the PCIP protein or biologically active portion thereof is determined. Determining the ability of the test compound to modulate the activity of a PCIP protein can be accomplished, for example, by determining the ability of the PCIP protein to bind to a PCIP target molecule by one of the methods described above for determining direct binding. Determining the ability of the PCIP protein to bind to a PCIP target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a PCIP protein can be accomplished by determining the ability of the PCIP protein to further modulate the activity of a downstream effector of a PCIP target molecule. For example, the activity of the effector molecule on an appropriate target can be determined or the binding of the effector to an appropriate target can be determined as previously described.

In yet another embodiment, the cell-free assay involves contacting a PCIP protein or biologically active portion thereof with a known compound which binds the PCIP protein to form an assay mixture, contacting the assay mixture with a test compound, and determining the ability of the test compound to interact with the PCIP protein, wherein determining the ability of the test compound to interact with the PCIP protein comprises determining the ability of the PCIP protein to preferentially bind to or modulate the activity of a PCIP target molecule.

The cell-free assays of the present invention are amenable to use of both soluble and/or membrane-bound forms of isolated proteins. In the case of cell-free assays in which a membrane-bound form of an isolated protein is used (e.g., a potassium channel) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton®X-114, Thesit®, Isotridecypoly (ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either PCIP or its target molecule to facilitate separation of complexed from uncomplexed forms of one or both of the proteins, as well as to accommodate automation of the assay. Binding of a test compound to a PCIP protein, or interaction of a PCIP protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/PCIP fusion proteins or glutathione-5-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or PCIP protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of PCIP binding or activity determined using standard techniques.

Other techniques for immobilizing proteins on matrices can also be used in the screening assays of the invention. For example, either a PCIP protein or a PCIP target molecule can be immobilized utilizing conjugation of biotin and streptavidin. Biotinylated PCIP protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with PCIP protein or target molecules but which do not interfere with binding of the PCIP protein to its target molecule can be derivatized to the wells of the plate, and unbound target or PCIP protein trapped in the wells by antibody conjugation. Methods for detecting such complexes, in addition to those described above for the GST-immobilized complexes, include immunodetection of complexes using antibodies reactive with the PCIP protein or target molecule, as well as enzyme-linked assays which rely on detecting an enzymatic activity associated with the PCIP protein or target molecule.

In another embodiment, modulators of PCIP expression are identified in a method wherein a cell is contacted with a candidate compound and the expression of PCIP mRNA or protein in the cell is determined. The level of expression of PCIP mRNA or protein in the presence of the candidate compound is compared to the level of expression of PCIP mRNA or protein in the absence of the candidate compound. The candidate compound can then be identified as a modulator of PCIP expression based on this comparison. For example, when expression of PCIP mRNA or protein is greater (statistically significantly greater) in the presence of the candidate compound than in its absence, the candidate compound is identified as a stimulator of PCIP mRNA or protein expression. Alternatively, when expression of PCIP mRNA or protein is less (statistically significantly less) in the presence of the candidate compound than in its absence, the candidate compound is identified as an inhibitor of PCIP mRNA or protein expression. The level of PCIP mRNA or protein expression in the cells can be determined by methods described herein for detecting PCIP mRNA or protein.

In yet another aspect of the invention, the PCIP proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with PCIP ("PCIP-binding proteins" or "PCIP-bp") and are involved in PCIP activity (described in more detail in the Examples section below). Such PCIP-binding proteins are also likely to be involved in the propagation of signals by the PCIP proteins or PCIP targets as, for example, downstream elements of a PCIP-mediated signaling pathway. Alternatively, such PCIP-binding proteins are likely to be PCIP inhibitors.

The two-hybrid system is based on the modular nature of most transcription factors, which consist of separable DNA-binding and activation domains. Briefly, the assay utilizes two different DNA constructs. In one construct, the gene that codes for a PCIP protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PCIP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PCIP protein.

This invention further pertains to novel agents identified by the above-described screening assays. Accordingly, it is within the scope of this invention to further use an agent identified as described herein in an appropriate animal model. For example, an agent identified as described herein (e.g., a PCIP modulating agent, an antisense PCIP nucleic acid molecule, a PCIP-specific antibody, or a PCIP-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to 741, uses of novel agents identified by the above-described screening assays for treatments, e.g., treatments of a CNS disorder, as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the PCIP nucleotide sequences, described herein, can be used to map the location of the PCIP genes on a chromosome. The mapping of the PCIP sequences to chromosomes is an important first step in correlating these sequences with genes associated with disease.

Briefly, PCIP genes can be mapped to chromosomes by preparing PCR primers (preferably 15–25 bp in length) from the PCIP nucleotide sequences. Computer analysis of the PCIP sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the PCIP sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the PCIP nucleotide sequences to design oligonucleotide primers, sublocalization can be achieved with panels of fragments from specific chromosomes. Other mapping strategies which can similarly be used to map a PCIP sequence to its chromosome include in situ hybridization (described in Fan, Y. et al. (1990) *Proc. Natl. Acad. Sci. USA,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the PCIP gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The PCIP sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the PCIP nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The PCIP nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. Non-coding sequences can comfortably provide positive individual identification with a panel of perhaps 10 to 1,000 primers which each yield a noncoding amplified sequence of 100 bases. If predicted coding sequences are used, a more appropriate number of primers for positive individual identification would be 500–2,000.

If a panel of reagents from PCIP nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial PCIP Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the PCIP nucleotide sequences or portions thereof, having a length of at least 20 bases, preferably at least 30 bases.

The PCIP nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such PCIP probes can be used to identify tissue by species and/or by organ type.

In a similar fashion, these reagents, e.g., PCIP primers or probes can be used to screen tissue culture for contamination (i.e. screen for the presence of a mixture of different types of cells in a culture).

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining PCIP protein and/or nucleic acid expression as well as PCIP activity, in the context of a biological sample (e.g., blood, serum, cells, tissue) to thereby determine whether an individual is afflicted with a disease or disorder, or is at risk of developing a disorder, associated with aberrant PCIP expression or activity. The invention also provides for prognostic (or predictive) assays for determining whether an individual is at risk of developing a disorder associated with PCIP protein, nucleic acid expression or activity. For example, mutations in a PCIP gene can be assayed in a biological sample. Such assays can be used for prognostic or predictive purpose to thereby phophylactically treat an individual prior to the onset of a disorder characterized by or associated with PCIP protein, nucleic acid expression or activity.

Another aspect of the invention pertains to monitoring the influence of agents (e.g., drugs, compounds) on the expression or activity of PCIP in clinical trials.

These and other agents are described in further detail in the following sections.

1. Diagnostic Assays

An exemplary method for detecting the presence or absence of PCIP protein or nucleic acid in a biological sample involves obtaining a biological sample from a test subject and contacting the biological sample with a compound or an agent capable of detecting PCIP protein or nucleic acid (e.g., mRNA, genomic DNA) that encodes PCIP protein such that the presence of PCIP protein or nucleic acid is detected in the biological sample. A preferred agent for detecting PCIP mRNA or genomic DNA is a labeled nucleic acid probe capable of hybridizing to PCIP mRNA or genomic DNA. The nucleic acid probe can be, for example, a full-length PCIP nucleic acid, such as the nucleic acid of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, or SEQ ID NO:47, or the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion thereof, such as an oligonucleotide of at least 15, 30, 50, 100, 250 or 500 nucleotides in length and sufficient to specifically hybridize under stringent conditions to PCIP mRNA or genomic DNA. Other suitable probes for use in the diagnostic assays of the invention are described herein.

A preferred agent for detecting PCIP protein is an antibody capable of binding to PCIP protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect PCIP mRNA, protein, or genomic DNA in a biological sample in vitro as well as in vivo. For example, in vitro techniques for detection of PCIP mRNA include Northern hybridizations and in situ hybridizations. In vitro techniques for detection of PCIP protein include enzyme linked immunosorbent assays (ELISAs), Western blots, immunoprecipitations and immunofluorescence. In vitro techniques for detection of PCIP genomic DNA include Southern hybridizations. Furthermore, in vivo techniques for detection of PCIP protein include introducing into a subject a labeled anti-PCIP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting PCIP protein, mRNA, or genomic DNA, such that the presence of PCIP protein, mRNA or genomic DNA is detected in the biological sample, and comparing the presence of PCIP protein, mRNA or genomic DNA in the control sample with the presence of PCIP protein, mRNA or genomic DNA in the test sample.

The invention also encompasses kits for detecting the presence of PCIP in a biological sample. For example, the kit can comprise a labeled compound or agent capable of detecting PCIP protein or mRNA in a biological sample; means for determining the amount of PCIP in the sample; and means for comparing the amount of PCIP in the sample with a standard. The compound or agent can be packaged in a suitable container. The kit can further comprise instructions for using the kit to detect PCIP protein or nucleic acid.

2. Prognostic Assays

The diagnostic methods described herein can furthermore be utilized to identify subjects having or at risk of developing a disease or disorder associated with aberrant PCIP expression or activity. For example, the assays described herein, such as the preceding diagnostic assays or the following assays, can be utilized to identify a subject having or at risk of developing a disorder associated with a misregulation in PCIP protein activity or nucleic acid expression, such as a neurodegenerative disorder, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; a psychiatric disorder, e.g., depression, schizophrenic disorders, Korsakoff's psychosis, mania, anxiety disorders, bipolar affective disorders, or phobic disorders; a learning or memory disorder, e.g., amnesia or age-related memory loss; a neurological disorder, e.g., migraine; a pain disorder, e.g., hyperalgesia or pain associated with muscoloskeletal disorders; spinal cord injury; stroke; and head trauma.

Alternatively, the prognostic assays can be utilized to identify a subject having or at risk for developing a disorder associated with a misregulation in PCIP protein activity or nucleic acid expression, such as a potassium channel associated disorder. Thus, the present invention provides a method for identifying a disease or disorder associated with aberrant PCIP expression or activity in which a test sample is obtained from a subject and PCIP protein or nucleic acid (e.g., mRNA or genomic DNA) is detected, wherein the presence of PCIP protein or nucleic acid is diagnostic for a subject having or at risk of developing a disease or disorder associated with aberrant PCIP expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant PCIP expression or activity. For example, such methods can be used to determine whether a subject can be effectively treated with an agent for a CNS disorder. Thus, the present invention provides methods for determining whether a subject can be effectively treated with an agent for a disorder associated with aberrant PCIP expression or activity in which a test sample is obtained and PCIP protein or nucleic acid expression or activity is detected (e.g., wherein the abundance of PCIP protein or nucleic acid expression or activity is diagnostic for a subject that can be administered the agent to treat a disorder associated with aberrant PCIP expression or activity).

The methods of the invention can also be used to detect genetic alterations in a PCIP gene, thereby determining if a subject with the altered gene is at risk for a disorder characterized by misregulation in PCIP protein activity or nucleic acid expression, such as a CNS disorder. In preferred embodiments, the methods include detecting, in a sample of cells from the subject, the presence or absence of a genetic alteration characterized by at least one of an alteration affecting the integrity of a gene encoding a PCIP-protein, or the mis-expression of the PCIP gene. For example, such genetic alterations can be detected by ascertaining the existence of at least one of 1) a deletion of one or more nucleotides from a PCIP gene; 2) an addition of one or more nucleotides to a PCIP gene; 3) a substitution of one or more nucleotides of a PCIP gene, 4) a chromosomal rearrangement of a PCIP gene; 5) an alteration in the level of a messenger RNA transcript of a PCIP gene, 6) aberrant modification of a PCIP gene, such as of the methylation pattern of the genomic DNA, 7) the presence of a non-wild type splicing pattern of a messenger RNA transcript of a PCIP gene, 8) a non-wild type level of a PCIP-protein, 9) allelic loss of a PCIP gene, and 10) inappropriate post-translational modification of a PCIP-protein. As described herein, there are a large number of assays known in the art which can be used for detecting alterations in a PCIP gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the PCIP-gene (see Abravaya et al. (1995) *Nucleic Acids Res* 0.23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a PCIP gene under conditions such that hybridization and amplification of the PCIP-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a PCIP gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in PCIP can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in PCIP can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the PCIP gene and detect mutations by comparing the sequence of the sample PCIP with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the PCIP gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes of formed by hybridizing (labeled) RNA or DNA containing the wild-type PCIP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in PCIP cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a PCIP sequence, e.g., a wild-type PCIP sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in PCIP genes. For example, single strand conformation polymorphism (SSCP) may be used to detect differences in electrophoretic mobility between mutant and wild type nucleic acids (Orita et al. (1989) *Proc Natl. Acad Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control PCIP nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a PCIP gene.

Furthermore, any cell type or tissue in which PCIP is expressed may be utilized in the prognostic assays described herein.

3. Monitoring of Effects During Clinical Trials

Monitoring the influence of agents (e.g., drugs) on the expression or activity of a PCIP protein (e.g., the modulation of membrane excitability or resting potential) can be applied not only in basic drug screening, but also in clinical trials. For example, the effectiveness of an agent determined by a screening assay as described herein to increase PCIP gene expression, protein levels, or upregulate PCIP activity, can be monitored in clinical trials of subjects exhibiting decreased PCIP gene expression, protein levels, or down-regulated PCIP activity. Alternatively, the effectiveness of an agent determined by a screening assay to decrease PCIP gene expression, protein levels, or downregulate PCIP activity, can be monitored in clinical trials of subjects exhibiting increased PCIP gene expression, protein levels, or upregulated PCIP activity. In such clinical trials, the expression or activity of a PCIP gene, and preferably, other genes that have been implicated in, for example, a potassium channel associated disorder can be used as a "read out" or markers of the phenotype of a particular cell.

For example, and not by way of limitation, genes, including PCIP, that are modulated in cells by treatment with an agent (e.g., compound, drug or small molecule) which modulates PCIP activity (e.g., identified in a screening assay as described herein) can be identified. Thus, to study the effect of agents on potassium channel associated disorders, for example, in a clinical trial, cells can be isolated and RNA prepared and analyzed for the levels of expression of PCIP and other genes implicated in the potassium channel associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of PCIP or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a PCIP protein, mRNA, or genomic DNA in the preadministration sample; (iii) obtaining one or more post-administration samples from the subject; (iv) detecting the level of expression or activity of the PCIP protein, mRNA, or genomic DNA in the post-administration samples; (v) comparing the level of expression or activity of the PCIP protein, mRNA, or genomic DNA in the pre-administration sample with the PCIP protein, mRNA, or genomic DNA in the post administration sample or samples; and (vi) altering the administration of the agent to the subject accordingly. For example, increased administration of the agent may be desirable to increase the expression or activity of PCIP to higher levels than detected, i.e., to increase the effectiveness of the agent. Alternatively, decreased administration of the agent may be desirable to decrease expression or activity of PCIP to lower levels than detected, i.e. to decrease the effectiveness of the agent. According to such an embodiment, PCIP expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) a disorder or having a disorder associated with aberrant PCIP expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the PCIP molecules of the present invention or PCIP modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant PCIP expression or activity, by administering to the subject a PCIP or an agent which modulates PCIP expression or at least one PCIP activity. Subjects at risk for a disease which is caused or contributed to by aberrant PCIP expression or activity can be identified by, for example, any or a combination of diagnostic or prognostic assays as described herein. Administration of a prophylactic agent can occur prior to the manifestation of symptoms characteristic of the PCIP aberrancy, such that a disease or disorder is prevented or, alternatively, delayed in its progression. Depending on the type of PCIP aberrancy, for example, a PCIP, PCIP agonist or PCIP antagonist agent can be used for treating the subject. The appropriate agent can be determined based on screening assays described herein.

2. Therapeutic Methods

Another aspect of the invention pertains to methods of modulating PCIP expression or activity for therapeutic purposes. Accordingly, in an exemplary embodiment, the modulatory method of the invention involves contacting a cell with a PCIP or agent that modulates one or more of the activities of PCIP protein activity associated with the cell. An agent that modulates PCIP protein activity can be an agent as described herein, such as a nucleic acid or a protein, a naturally-occurring target molecule of a PCIP protein (e.g., a PCIP substrate), a PCIP antibody, a PCIP agonist or antagonist, a peptidomimetic of a PCIP agonist or antagonist, or other small molecule. In one embodiment, the agent stimulates one or more PCIP activities. Examples of such stimulatory agents include active PCIP protein and a nucleic acid molecule encoding PCIP that has been introduced into the cell. In another embodiment, the agent inhibits one or more PCIP activities. Examples of such inhibitory agents include antisense PCIP nucleic acid molecules, anti-PCIP antibodies, and PCIP inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a PCIP protein or nucleic acid molecule. Examples of such disorders include CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, Korsakoff's psychosis, mania, anxiety disorders, bipolar affective disorders, or phobic disorders; learning or memory disorders, e.g., amnesia or age-related memory loss; neurological disorders, e.g., migraine; pain disorders, e.g., hyperalgesia or pain associated with muscoloskeletal disorders; spinal cord injury; stroke; and head trauma. In one embodiment, the method involves administering an agent (e.g., an agent identified by a screening assay described herein), or combination of agents that modulates (e.g., upregulates or downregulates) PCIP expression or activity. In another embodiment, the method involves administering a PCIP protein or nucleic acid molecule as therapy to compensate for reduced or aberrant PCIP expression or activity.

A preferred embodiment of the present invention involves a method for treatment of a PCIP associated disease or disorder which includes the step of administering a therapeutically effective amount of a PCIP antibody to a subject. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

Stimulation of PCIP activity is desirable in situations in which PCIP is abnormally downregulated and/or in which increased PCIP activity is likely to have a beneficial effect. For example, stimulation of PCIP activity is desirable in situations in which a PCIP is downregulated and/or in which increased PCIP activity is likely to have a beneficial effect. Likewise, inhibition of PCIP activity is desirable in situations in which PCIP is abnormally upregulated and/or in which decreased PCIP activity is likely to have a beneficial effect.

3. Pharmacogenomics

The PCIP molecules of the present invention, as well as agents, or modulators which have a stimulatory or inhibitory effect on PCIP activity (e.g., PCIP gene expression) as identified by a screening assay described herein can be administered to individuals to treat (prophylactically or therapeutically) potassium channel associated disorders associated with aberrant PCIP activity (e.g, CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, Korsakoff's psychosis, mania, anxiety disorders, bipolar affective disorders, or phobic disorders; learning or memory disorders, e.g., amnesia or age-related memory loss; neurological disorders, e.g., migraine; pain disorders, e.g., hyperalgesia or pain associated with muscoloskeletal disorders; spinal cord injury; stroke; and head trauma). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a PCIP molecule or PCIP modulator as well as tailoring the dosage and/or therapeutic regimen of treatment with a PCIP molecule or PCIP modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11):983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a PCIP protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a PCIP molecule or PCIP modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a PCIP molecule or PCIP modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

The following materials and methods were used in the Examples.

Strains, Plasmids, Bait cDNAs, and General Microbiological Techniques

Basic yeast strains (HF7c, Y187,) bait (pGBT9) and fish (pACT2) plasmids used in this work were purchased from Clontech (Palo Alto, Calif.). cDNAs encoding rat Kv4.3, Kv4.2, and Kv 1.1, were provided by Wyeth-Ayerst Research (865 Ridge Rd., Monmouth Junction, N.J. 08852) Standard yeast media including synthetic complete medium lacking L-leucine, L-tryptophan, and L-histidine were prepared and yeast genetic manipulations were performed as described (Sherman (1991) Meth. Enzymol. 194:3–21).

Yeast transformations were performed using standard protocols (Gietz et al. (1992) *Nucleic Acids Res.* 20:1425; Ito et al (1983) *J. Bacteriol.* 153:163–168). Plasmid DNAs were isolated from yeast strains by a standard method (Hoffman and Winston (1987) *Gene* 57:267–272).

Bait and Yeast Strain Construction

The first 180 amino acids of rKv4.3 (described in Serdio P. et al. (1996) *J. Neurophys* 75:2174–2179) were amplified by PCR and cloned in frame into pGBT9 resulting in plasmid pFWA2, (hereinafter "bait"). This bait was transformed into the two-hybrid screening strain HF7c and tested for expression and self-activation. The bait was validated for expression by Western blotting. The rKv4.3 bait did not self-activate in the presence of 10 mM 3-amino-1,2,3-Triazole (3-AT).

Library Construction

Rat mid brain tissue was provided by Wyeth-Ayerst Research (Monmouth Junction, N.J.). Total cellular RNA was extracted from the tissues using standard techniques (Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., (1989)). mRNA was prepared using a Poly-A Spin mRNA Isolation Kit from New England Biolabs (Beverly, Mass.). cDNA from the mRNA sample was synthesized using a cDNA Synthesis Kit from Stratagene (La Jolla, Calif.) and ligated into pACT2's EcoRI and XhoI sites, giving rise to a two-hybrid library.

Two-Hybrid Screening

Two-hybrid screens were carried out essentially as described in Bartel, P. et al. (1993) "Using the Two-Hybrid System to Detect Polypeptide—Polypeptide Interactions" in Cellular Interactions in Development: A Practical Approach, Hartley, D. A. ed. Oxford University Press, Oxford, pp. 153–179, with a bait-library pair of rkv4.3 bait-rat mid brain library. A filter disk beta-galactosidase (beta-gal) assay was performed essentially as previously described (Brill et al. (1994) *Mol. Biol. Cell.* 5:297–312). Clones that were positive for both reporter gene activity (His and beta-galactosidase) were scored and fish, plasmids were isolated from yeast, transformed into *E. coli* strain KC8, DNA plasmids were purified and the resulting plasmids were sequenced by conventional methods (Sanger F. et al. (1977) *PNAS,* 74: 5463–67).

Specificity Test

Positive interactor clones were subjected to a binding specificity test where they were exposed to a panel of related and unrelated baits by a mating scheme previously described (Finley R. L. Jr. et al. (1994) *PNAS,* 91(26):12980–12984). Briefly, positive fish plasmids were transformed into Y187 and the panel of baits were transformed into HF7c. Transformed fish and bait cells were streaked out as stripes on selective medium plates, mated on YPAD plates, and tested for reporter gene activity.

Analysis

PCIP nuleotides were analyzed for nucleic acid hits by the BLASTN 1.4.8 MP program (Altschul et al. (1990) Basic Local Alignment Search Tool. *J. Mol. Biol.* 215: 403–410). PCIP proteins were analyzed for polypeptide hits by the BLASTP 1.4.9 MP program.

Example 1

Identification of Rat PCIP cDNAs

The Kv4.3 gene coding sequence (coding for the first 180 amino acids) was amplified by PCR and cloned into pGBT9 creating a GAL4 DNA-binding domain-Kv4.3(1–180) gene fusion (plasmid pFWA2). HF7c was transformed with this construct. The resulting strain grew on synthetic complete medium lacking L-tryptophan but not on synthetic complete medium lacking L-tryptophan and L-histidine in the presence of 10 mM 3-AT demonstrating that the {GAL4 DNA-binding domain}-{vKv4.3(1–180)} gene fusion does not have intrinsic transcriptional activation activity higher than the threshhold allowed by 10 mM 3-AT.

In this example, a yeast two-hybrid assay was performed in which a plasmid containing a {GAL4 DNA-binding domain}-{rKv4.3(1–180)} gene fusion was introduced into the yeast two-hybrid screening strain HF7c described above. HF7c was then transformed with the rat mid brain two-hybrid library. Approximately six million transformants were obtained and plated in selection medium. Colonies that grew in the selection medium and expressed the beta-galactosidase reporter gene were further characterized and subjected to retransformation and specificity assays. The retransformation and specificity tests yielded three PCIP clones (rat 1 v, 8t, and 9qm) that were able to bind to the Kv4.3 polypeptide.

The full length sequences for the rat 1v gene, and partial sequences for 8t and 9q genes were derived as follows. The partial rat PCIP sequences were used to prepare probes, which were then used to screen, for example, rat mid brain cDNA libraries. Positive clones were identified, amplified and sequenced using standard techniques, to obtain the full length sequence. Additionally, a rapid amplification of the existing rat PCIP cDNA ends (using for example, 5' RACE, by Gibco, BRL) was used to complete the 5' end of the transcript.

Example 2

Identification of Human 1v cDNA

To obtain the human 1v nucleic acid molecule, a cDNA library made from a human hippocampus (Clontech, Palo Alto, Calif.) was screened under low stringency conditions as follows: Prehybridization for 4 hours at 42° C. in Clontech Express Hyb solution, followed by overnight hybridization at 42° C. The probe used was a PCR-generated fragment including nucletides 49–711 of the rat sequence labeled with $^{32}P$ dCTP. The filters were washed 6 times in 2×SSC/0.1% SDS at 55° C. The same conditions were used for secondary screening of the positive isolates. Clones thus obtained were sequenced using an ABI automated DNA Sequencing system, and compared to the rat sequences shown in SEQ ID NO:3 as well as to known sequences from the GenBank database. The largest clone from the library screen was subsequently subcloned into pBS-KS+(Stratagene, La Jolla, Calif.) for sequence verification. The 515 base pair clone was determined to represent the human homolog of the 1v gene, encompassing 211 base pairs of 5' UTR and a 304 base pair coding region. To generate the full-length cDNA, 3' RACE was used according to the manufacturers instructions (Clontech Advantage PCR kit).

Example 3

Isolation and Characterization of 1V Splice Variants

The mouse 1v shown in SEQ ID NO:5 and the rat 1vl splice variant shown in SEQ ID NO:7 was isolated using a two-hybrid assay as described in Example 1. The mouse 1 vl splice variant shown in SEQ ID NO: 7 was isolated by screening a mouse brain cDNA library, and the rat 1 vn splice variant shown in SEQ ID NO:11 was isolated by BLAST searching.

Example 4

Isolation and Identification of 9Q and Other PCIPs

Rat 9ql (SEQ ID NO: 15) was isolated by database mining, rat 9qm (SEQ ID NO: 21) was isolated by a two-hybrid assay, and rat 9qc (SEQ ID NO:27) was identified by database mining. Human 9ql (SEQ ID NO: 13), and human 9qs (SEQ ID NO: 23) were identified as described in Example 2. Mouse 9ql (SEQ ID NO: 17), monkey 9qs (SEQ ID NO:25), human p195 (SEQ ID NO:31), W28559 (SEQ ID NO:37), human p193 (SEQ ID NO:39), rat p19 (SEQ ID NO:33), and mouse p19 (SEQ ID NO:35) were identified by database mining. Rat 8t (SEQ ID NO:29) was identified using a two-hybrid assay.

The human genomic 9q sequence (SEQ ID NOs:46 and 47) was isolated by screening a BAC genomic DNA library (Reasearch Genetics) using primers which were designed based on the sequence of the human 9qm cDNA. Two positive clones were identified (44802 and 721117) and sequenced.

Example 5

Expression of 1V, 8T, and 9Q mRNA in Rat Tissues

Rat multiple tissue Northern blots (Clontech) were probed with a [$^{32}$P]-labeled cDNA probe directed at the 5'-untranslated and 5'-coding region of the rat 1v sequence (nucleotides 35–124; SEQ ID NO:3) (this probe is specific for rat 1v and rat 1vl), the 5' coding region of the 8t sequence (nucleotides 1–88; SEQ ID NO:29) (this probe is specific for 8t), or the 5' end of the rat 9qm sequence (nucleotides 1–195; SEQ ID NO:21) (this probe is specific for all 9q isoforms, besides 8t). Blots were hybridize using standard techniques. Northern blots hybridized with the rat 1v probe revealed a single band at 2.3 kb only in the lane containing brain RNA, suggesting that 1v expression is brain specific. Northern blots probed with the rat 8t probe revealed a major band at 2.4 kb. Although the rat 8t band was most intense in the lane containing heart RNA, there was also a weaker band in the lane containing brain RNA. Northern blots hybridized with the 9q cDNA probe revealed a major band at 2.5 kb and a minor band at over 4 kb with predominant expression in brain and heart. The minor band may represent incompletely spliced or processed 9q mRNA.

Example 6

Expression of 1V, 8T, and 9Q in Brain

Expression of the rat 1v and 8t/9q genes in the brain was examined by in situ hybridization histochemistry (ISHH) using [$^{35}$S]-labeled cRNA probes and a hybridization procedure identical to that described in Rhodes et al. (1996) J. Neurosci., 16:4846–4860. Templates for preparing the cRNA probes were generated by standard PCR methods. Briefly, oligonucleotide primers were designed to amplify a fragment of 3'- or 5'-untranslated region of the target cDNA and in addition, add the promoter recognition sequences for T<u>7</u> and T<u>3</u> polymerase. Thus, to generate a 300 nucleotide probe directed at the 3'-untranslated region of the 1v mRNA, we used the following primers:

5-TAATACGACTCACTATAGGGACTGGCCATCCTGC TCTCAG-3 (T<u>7</u>, forward, sense; SEQ ID NO:42)

5-ATTAACCCTCACTAAAGGGACACTACT-GTTTAAGCTCAAG-3 (T<u>3</u>, reverse, antisense; SEQ ID NO:43). The underlined bases correspond to the T<u>7</u> and T<u>3</u> promoter sequences. To generate a probe directed at a 325 bp region of 3'-untranslated sequence shared by the 8t and 9q mRNAs, the following primers were used:

5-TAATACGACTCACTATAGGGCACCTCCCCTCCGG CTGTTC-3 (T<u>7</u>, forward, sense; SEQ ID NO:44)

5-ATTAACCCTCACTAAAGGGAGAGCAGCAGCATG GCAGGGT-3 (T<u>3</u>, reverse, antisense; SEQ ID NO:45).

Autoradiograms of rat brain tissue sections processed for ISHH localization of 1 v or 8t/9q mRNA expression revealed that 1v mRNA is expressed widely in brain in a pattern consistent with labeling of neurons as opposed to glial or endothelial cells. 1v mRNA is highly expressed in cortical, hippocampal, and striatal interneurons, the reticlar nucleus of the thalamus, the medial habenula, and in cerebellar granule cells. 1v mRNA is expressed at moderate levels in midbrain nuclei including the substantia nigra and superior colliculus, in several other thalamic nuclei, and in the medial septal and diagonal band nuclei of the basal forebrain.

Because the probe used to analyze the expression of 8t and 9q hybridizes to a region of the 3-untranslated region that is identical in the 8t and 9q mRNAs, this probe generates a composite image that reveals that 8t/9q mRNA is expressed widely in brain in a pattern that partly overlaps with that for 1 v as described above. However, 8t/9q mRNA is highly expressed in the striatum, hippocampal formation, cerebellar granule cells, and neocortex. 8t/9q mRNA is expressed at moderate levels in the midbrain, thalamus, and brainstem. In may of these areas, 8t./9q mRNA appears to be concentrated in interneurons in addition to 0 principal cells, and in all regions 8t/9q expression appears to be concentrated in neurons as apposed to glial cells.

Single- and double-label immunohistochemistry revealed that the PCIP and Kv4 polypeptides are precisely colocalized in many of the cell types and brain regions where PCIP and Kv4 mRNAs are coexpressed. For example, 9qm colocalized with Kv4.2 in the somata and dendrites of hippocampal granule and pyramidal cells, neurons in the medial habenular nucleus and in cerebellar basket cells, while 1v colocalized with Kv4.3 in layer II neurons of posterior cingulate cortex, hippocampal interneurons, and in a subset of cerebellar granule cells. Immunoprecipitation analyses indicated that 1v and 9qm are coassociated with Kv4 α-subunits in rat brain membranes.

Example 7

Co-ASSOCIATION 1V and Kv4.3 in COS Cells

COS 1 cells were transiently transfected with rat Kv4.3 alone, rat Kv4.3+rat 1 v, and rat 1v alone using the lipofectamine plus procedure essentially as described by the manufacturer (Boehringer Mannheim). Forty-eight hours after the transfection, cells were washed, fixed, and processed for immunofluorescent visualization as described previously (Bekele-Arcuri et al. (1996) Neuropharmacology, 35:851–865). Affinity-purified rabbit polyclonal or mouse monoclonal antibodies to the Kv4.3 or rat 1 v protein were used for immunofluorescent detection of the target proteins. Cells transfected with 1v alone and stained with 1v-specific revealed that 1v is diffusely distributed throughout the cytoplasm of transiently transfected cells, as expected for a cytoplasmic protein. Cells transiently transfected with Kv4.3 alone and stained with antibodies specific for Kv4.3 revealed that although much of the expressed channel protein is trapped within intracellular organelles, Kv4.3 expression is also concentrated at the outer margins of the cell and is presumed to be associated with the cell membrane. When the 1v protein is coexpressed with Kv4.3 in COS1 cells, the subcellular distribution of Iv is dramatically different than it is in cells transfected with 1v alone. In cells cotransfected with 1v and Kv4.3, 1v protein expression appears to be trapped in intracellular organelles and becomes concentrated at the outer margins of the cell. Double-label immunofluorescence of these co-transfected cells indicates that the pattern of 1v immunofluorecence is identical that for Kv4.3, indicating that these two proteins are extensively colocalized in cotransfected cells. Moreover, the extensive and dramatic change in the subcellular distribution of 1v when it is coexpressed with Kv4.3 suggests that the proteins coassociate when they are coexpressed.

To further demonstrate that 1v and Kv4.3 directly associate in cotransfected cells, COS1 cells were cotransfected with 1v and Kv4.3 cDNAs as described above. The cells were then lysed in buffer containing detergent and protease inhibitors, and prepared for immunoprecipitation reactions essentially as described previously (Nakahira et al. (1996) J. Biol. Chem., 271:7084–7089). Antibodies specific for 1v or Kv4.3 were used to immunoprecipitate the corresponding polypeptide from the transfected cell lysates essentially as described in Nakahira et al. (1996) J. Biol. Chem., 271: 7084–7089 and in Harlow E. and Lane, D., Antibodies:A Laboratory Manual, Cold Spring Harbor Laboratory, c1988. The products resulting from the immunoprecipitation were size fractionated by SDS-PAGE and transferred to nitrocellulose filters using standard procedures. Immunoblots performed using Kv4.3-specific antibodies revealed that 1v co-immunoprecipitates Kv4.3 from lysates prepared from co-transfected cells, indicating that the two proteins are tightly co-associated. Taken together, these data suggest that 1v may promote the transit of the Kv4.3 subunits to the cell surface, and that this chaperone-like effect may underlie the enhancement of Kv4 current density by 1v.

Example 8

Electrophysiological Characterization of PCIPs

Currents flowing through rKv4.2 were measured electrophysiologically after transiently transfecting the channels (with or without rat 1v) in CHO cells or microinjecting in vitro transcribed mRNA into *Xenopus* oocytes. Currents in CHO cells were measured using the patch-clamp technique (Hamill et al. 1981. Pfluegers Arch. 391: 85–100), while currents in oocytes were measured with two-electrode voltage clamp. CHO cells were transiently-transfected with cDNA using the DOTAP lipofection method as described by the manufacturer. (Boehringer Mannheim, Inc.). Transfected cells were identified by cotransfecting enhanced GFP along with the genes of interest and subsequently determining if the cells contained green GFP fluorescence. Alternatively, oocytes were injected with 1–3 ng/oocyte cRNA which was prepared using standard in vitro transcription techniques (Sambrook et al. 1989. Molecular Cloning: a laboratory manual, Cold Spring Harbor Press). When CHO cells were transfected with 1 μg rKv4.2 cDNA, current levels averaged about 539 pA/cell, or 23.1 pA/pF (Table 2). When 1v was coexpressed with rKv4.2, however, the current amplitude increased by 8.5 fold to an average of 3076 pA/cell or 197.2 pA/pF (see below).

TABLE 2

| Parameter | CHO | | Oocytes | | Oocytes | |
| --- | --- | --- | --- | --- | --- | --- |
| | rKv4.2 | rKv4.2 + 1v | hKv4.3 | hKv4.3 + 1v | hKv1.4 | hKv1.4 + 1v |
| Peak Current (pA/cell) | 538.8 | 3076.3 | 7.7 A | 18.1 A | 8.3 A | 6.5 A |
| Peak Current (pA/pF) | 23.1 | 197.2 | — | — | — | — |
| Inactivation time constant (ms, at 40 mV) | 20.4 | 90.9 | 58.5 | 137.0 | 52.3 | 57.8 |
| Recovery from Inactivation time constant (ms, at −80 mV) | 247.3 | 39.7 | 327.0 | 34.5 | 132.6, 666.8 | 210.7, 821.9 |
| Activation $V_{1/2}$(mV) | 13.1 | −15.9 | −19.2 | −45.5 | −21.0 | −13.5 |
| Steady-state Inactivation $V_{1/2}$(mV) | −54.1 | −59.7 | −57.4 | −56.8 | −47.5 | −48.1 |

Coexpression of 1v also caused a number of changes in other kinetic parameters of the rKv4.2 current. The voltage at which half of the channels are activated is a measure of the voltage dependence of the channels. This half activation voltage for rKv4.2 was relatively high at 13 mV. Coexpression of 1v with rKv4.2 shifted the half activation voltage by 29 mV to the more negative potential of −16 mV (Table 2). The voltage at which channels inactivate during a long (1 second) pulse only shifted slightly from −54 to −60 mV with 1v coexpression.

The modulatory effects observed with 1v coexpression were not limited to the rKv4.2 channel or to CHO cells. A similar modulation by 1v of hKv4.3 expressed in *Xenopus* oocytes has also been observed (see Table 2). Co-injection of 1v into oocytes induced an increase in hKv4.3 current, a slowing of inactivation, a speeding of the recovery from inactivation, and a leftward shift in the activation curve. The effects of 1v, however, did not translate to all inactivating channel types, as the inactivating hKv1.4 channel was not effected by coinjection of 1v mRNA into oocytes (Table 2).

Co-expression of 1v or 9qm with Kv4 α-subunits in CHO cells or *Xenopus* oocytes revealed that the corresponding polypeptides co-associate with Kv4 subunits and dramatically modulate the current density, rate of inactivation and rate of recovery from inactivation of Kv4 channels.

Deletion of the N-terminus of the two PCIP proteins 1v and 9qm (the first 31 amino acids were deleted from 1v and the first 67 amino acids were deleted from 9qm) did not alter their modulatory actions on Kv4.2 current amplitude and kinetics when co-expressed in CHO cells. Thus, the variable N-terminus of these genes is not responsible for their modulatory actions on Kv4 channels. Point mutations were then constructed in the EF-hand domains of the 1v gene to remove its putative ability to bind calcium. Two different mutants were created: one has point mutations in the first two EF hands ($D_{199}$ to A, $G_{104}$ to A, $D_{135}$ to A, and $G_{140}$ to A) and the other one has point muations in all three EF hands ($D_{199}$ to A, G104 to A, $D_{135}$ to A, $G_{140}$ to A, $D_{183}$ to A, and $G_{188}$ to A). These mutations had a large effect on the modulatory function of this gene; co-expression with Kv4.2 produced a much smaller increase in current than the wild type 1v and very little effect on the other kinetic parameters of the channel. Thus, the EF-hand, or putative $Ca^{2+}$ binding domains, of 1v appear to have a critical role in the modulatory actions of the PCIP genes.

Example 9

Characterization of the PCIP Proteins

In this example, the amino acid sequences of the PCIP proteins were compared to amino acid sequences of known proteins and various motifs were identified.

The 1v polypeptide, the amino acid sequence of which is shown in SEQ ID NO:3 is a novel polypeptide which includes 216 amino acid residues. Domains that are putatively involved in calcium binding (Linse, S. and Forsen, S. (1995) *Advances in Second Messenger and Phosphoprotein Research* 30, Chapter 3, p89–151, edited by Means, Ariz., Raven Press, Ltd., New York), were identified by sequence alignment (see FIG. 21).

The 8t polypeptide, the amino acid sequence of which is shown in SEQ ID NO:30 is a novel polypeptide which includes 225 amino acid residues. Calcium binding domains that are putatively involved in calcium binding (Linse, S. and Forsen, S. (1995) *Advances in Second Messenger and Phosphoprotein Research* 30, Chapter 3, p89–151, edited by Means, Ariz., Raven Press, Ltd., New York), were identified by sequence alignment (see FIG. 21).

The 9q polypeptide is a novel polypeptide which includes calcium binding domains that are putatively involved in calcium binding (Linse, S. and Forsen, S. (1995) *Advances in Second Messenger and Phosphoprotein Research* 30, Chapter 3, p89–151, edited by Means, Ariz., Raven Press, Ltd., New York (see FIG. 21).

The p19 polypeptide is a novel polypeptide which includes calcium binding domains that are putatively involved in calcium binding (Linse, S. and Forsen, S. (1995) *Advances in Second Messenger and Phosphoprotein Research* 30, Chapter 3, p89–151, edited by Means, Ariz., Raven Press, Ltd., New York (see FIG. 21).

A BLASTN 2.0.7 search (Altschul et al. (1990) *J. Mol. Biol.* 215:403) of the nucleotide sequence of rat 1vl revealed that the rat 1vl is similar to the rat cDNA clone RMUAH89 (Accession Number AA849706). The rat 1 vl nucleic acid molecule is 98% identical to the rat cDNA clone RMUAH89 (Accession Number AA849706) over nucleotides 1063 to 1488.

A BLASTN 2.0.7 search (Altschul et al. (1990) *J. Mol. Biol.* 215:403) of the nucleotide sequence of human 9ql revealed that the human 9ql is similar to the human cDNA clone 1309405 (Accession Number AA757119). The human 9 ql nucleic acid molecule is 98% identical to the human cDNA clone 1309405 (Accession Number AA757119) over nucleotides 937 to 1405.

A BLASTN 2.0.7 search (Altschul et al. (1990) *J. Mol. Biol.* 215:403) of the nucleotide sequence of mouse P19 revealed that the mouse P19 is similar to the *Mus musculus* cDNA clone MNCb-7005 (Accession Number AU035979). The mouse P19 nucleic acid molecule is 98% identical to the *Mus musculus* cDNA clone MNCb-7005 (Accession Number AU035979) over nucleotides 1 to 583.

Example 10

Expression of Recombinant PCIP Proteins in Bacterial Cells

In this example, PCIP is expressed as a recombinant glutathione-5-transferase (GST) fusion polypeptide in *E. coli* and the fusion polypeptide is isolated and characterized. Specifically, PCIP is fused to GST and this fusion polypeptide is expressed in *E. coli*, e.g., strain BI21. Expression of the GST-PCIP fusion protein in BI21 is induced with IPTG. The recombinant fusion polypeptide is purified from crude bacterial lysates of the induced BI21 strain by affinity chromatography on glutathione beads. Using polyacrylamide gel electrophoretic analysis of the polypeptide purified from the bacterial lysates, the molecular weight of the resultant fusion polypeptide is determined.

Rat 1v and 9ql were cloned into pGEX-6p-2 (Pharmacia). The resulting recombinant fusion proteins were expressed in *E. coli* cells and purified following art known methods (described in, for example, *Current Protocols in Molecular Biology*, eds. Ausubel et al. John Wiley & Sons: 1992). The identities of the purified proteins were verified by western blot analysis using antibodies raised against peptide epitopes of rat 1v and 9ql.

Example 11

Expression of Recombinant PCIP Proteins in COS Cells

To express the PCIP gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire PCIP protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the PCIP DNA sequence is amplified by PCR using two primers. The 5' primer contains the restriction site of interest followed by approximately twenty nucleotides of the PCIP coding sequence starting from the initiation codon; the 3' end sequence contains complementary sequences to the other restriction site of interest, a translation stop codon, the HA tag or FLAG tag and the last 20 nucleotides of the PCIP coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the PCIP gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the PCIP-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the PCIP polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the PCIP coding sequence is cloned directly into the polylinker of the pcDNA/Amp vector using the appropriate restriction sites. The resulting plasmid is transfected into COS cells in the manner described above, and the expression of the PCIP polypeptide is detected by radiolabelling and immunoprecipitation using a PCIP specific monoclonal antibody.

Rat 1v was cloned into the mammalian expresssion vector pRBG4. Transfections into COS cells were performed using LipofectAmine Plus (Gibco BRL) following the manufacturer's instructions. The expressed 1v protein was detected by immunocytochemistry and/or western blot analysis using antibodies raised against 1v in rabbits or mice.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polypeptide comprising an amino acid sequence which is at least 90% identical to the amino acid sequence of SEQ ID NO: 32, wherein said identity is over the entire length of SEQ ID NO: 32, and wherein said polypeptide binds to a potassium channel.

2. The isolated polypeptide of claim 1, wherein said amino acid sequence is at least 95% identical to the amino acid sequence of SEQ ID NO:32, and wherein said identity is over the entire length of SEQ ID NO:32.

3. The isolated polypeptide of claim 1 comprising the amino acid sequence of SEQ ID NO:32.

4. The isolated polypeptide of claim 1 consisting of the amino acid sequence of SEQ ID NO:32.

5. An isolated polypeptide which is encoded by a nucleic acid molecule comprising a nucleotide sequence which is at least 90% identical to the nucleotide sequence of SEQ ID NO: 31, wherein said identity is over the entire length of SEQ ID NO: 31, and wherein said polypeptide binds to a potassium channel.

6. The isolated polypeptide of claim 1, wherein said nucleotide sequence is at least 95% identical to the nucleotide sequence of SEQ ID NO:31, and wherein said identity is over the entire length of SEQ ID NO:31.

7. The isolated polypeptide of claim 5 which is encoded by a nucleic acid molecule comprising the nucleotide sequence of SEQ ID NO:31.

8. The isolated polypeptide of claim 5 which is encoded by a nucleic acid molecule consisting of the nucleotide sequence of SEQ ID NO:31.

9. An isolated polypeptide comprising an amino acid sequence encoded by the DNA plasmid insert of the plasmid deposited with ATCC as Accession Number 98938.

10. The isolated polypeptide of claim 9 consisting of an amino acid sequence encoded by the DNA insert of the plasmid deposited with ATCC as Accession Number 98938.

11. An isolated polypeptide which is encoded by a nucleic acid molecule which hybridizes to the complement of SEQ ID NO: 31 in 6×SSC at 45° C., followed by one or more washes in 0.2×SSC, 0.1% SDS at 50–65° C., wherein said polypeptide binds to a potassium channel.

12. An isolated polypeptide comprising about 125–200 contiguous amino acid residues of the amino acid sequence of SEQ ID NO: 32, wherein said polypeptide binds to a potassium channel.

13. The polypeptide of any one of claims 1, 5, 9 or 11 further comprising heterologous amino acid sequences.

* * * * *